US008329432B2

(12) United States Patent
Kobilka et al.

(10) Patent No.: US 8,329,432 B2
(45) Date of Patent: Dec. 11, 2012

(54) METHOD AND COMPOSITION FOR CRYSTALLIZING G PROTEIN-COUPLED RECEPTORS

(75) Inventors: Brian Kobilka, Palo Alto, CA (US); Daniel Rosenbaum, Burlingame, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 64 days.

(21) Appl. No.: 12/932,100

(22) Filed: Feb. 16, 2011

(65) Prior Publication Data

US 2012/0136137 A1    May 31, 2012

Related U.S. Application Data

(63) Continuation of application No. 12/803,328, filed on Jun. 23, 2010, now Pat. No. 8,260,596, which is a continuation of application No. 12/288,097, filed on Oct. 15, 2008, now Pat. No. 7,790,850.

(60) Provisional application No. 61/000,176, filed on Oct. 17, 2007.

(51) Int. Cl.
*C07K 14/705* (2006.01)
*C12N 15/62* (2006.01)

(52) U.S. Cl. ................. 435/69.7; 530/350; 536/23.4

(58) Field of Classification Search .................. None
See application file for complete search history.

(56) References Cited

U.S. PATENT DOCUMENTS

| 2003/0198976 A1 | 10/2003 | Feder et al. |
| 2006/0188964 A1 | 8/2006 | Mancia et al. |
| 2007/0031832 A1 | 2/2007 | Watt et al. |
| 2007/0122881 A1 | 5/2007 | Surber |
| 2011/0031438 A1 | 2/2011 | Stevens et al. |
| 2011/0130543 A1 | 6/2011 | Stevens et al. |

FOREIGN PATENT DOCUMENTS

| WO | 03/000855 | 1/2003 |
| WO | 2008/068534 | 6/2008 |
| WO | 2009/055509 | 4/2009 |
| WO | 2009/055512 | 4/2009 |

OTHER PUBLICATIONS

Bell; et al., "Comparison of the Crystal Structure of Bacteriophase T4 Lysozyme at Low, Medium, and High Ionic Strengths", Proteins: Structure, Function, and Genetics (1991), 10:10-21.
Cheng; et al., "Kinetics and Equilibria of Lysozyme Precipitation and Crystallization in Concentrated Ammonium Sulfate Solutions", Biotechnology and Bioengineering (2006), 94(1):177-188.
Cherezov; et al., "High-Resolution Crystal Structure of an Engineered Human beta2-Adrenergic G Protein Coupled Receptor", Science (2007), 318(5854):1258-65.
Engel; et al., "Insertion of carrier proteins into hydrophilic loops of the *Escherichia coli* lactose permease", Biochemica et Biphysica Acta (2002), 1564:38-46.
Espitalier; et al., "Mechanism of formation of lysozyme crystals in concentrated ammonium sulfate solution from concentration profiles and equilibria: Influence of the 2nd osmotic virial coefficient", Powder Technology (2009), 190:112-117.
Evrard; et al., "Crystal Structure of the Lysozyme from Bacteriophage Lambda and its Relationship with V and C-type Lysozymes", J. Mol. Biol. (1998), 276:151-164.
Forsythe; et al., "Crystallization of chicken egg-white lysozyme from ammonium sulfate", Acta Cryst. (1997), D53:795-797.
Harada; et al., "Preliminary X-ray Crystallographic Study of Lysozyme Produced by Streptomyces globisporus", J. Mol. Biol. (1989), 207:851-852.
Hoffman; et al., "A FLAsH-based FRET approach to determine G protein-coupled receptor activation in living cells", Nature Methods (2005), 2(3):171-6.
Lapinsh; et al., "Classification of G-protein coupled receptors by alignment-independent extraction of principal chemical properties of primary amino acid sequences", Protein Science (2002), 11:795-805.
Lyne; et al., "Preliminary Crystallographic Examination of a Novel Fungal Lysozyme from Chalaropsis", The Journal of Biological Chemistry (1990), 265(12):6928-6930.
Marana; et al., "Crystallization, data collection and phasing of two digestive lysozymes from Musca domestica", Acta Cryst. (2006), F62:750-752.
Prive, "Fusion Proteins as Tools for Crystallization: the Lactose Permease from *Escherichia coli*", Acta Cryst. (1994), D50:375-379.
Prive; et al., "Engineering the Lac Permease for Purification and Crystallization", Journal of Bioenergetics and Biomembranes (1996), 28(1):29-34.
Rasmussen; et al., "Crystal structure of the human beta2 adrenergic G-protein-coupled receptor", Nature (2007), 450(7168):383-7.
Remington; et al., "Structure of the Lysozyme from Bacteriophage T4: An Electron Density Map at 2 4 A Resolution", J. Mol. Biol. (1978), 118:81-98.
Ries-Kautt; et al., "Crystallization of Previously Desalted Lysozyme in the Presence of Sulfate Ions", Acta Cryst. (1994), D50:366-369.
Ries-Kautt; et al., "Relative Effectiveness of Various Ions on the Solubility and Crystal Growth of Lysozyme", The Journal of Biological Chemistry (1989), 264(2):745-748.
Rosenbaum; et al., "GPCR Engineering Yields High-Resolution Structural Insights into beta2-Adrenergic Receptor Function", Science (2007), 318:(5854):1266-73.
Strynadka; et al., "Lysozyme: A model enzyme in protein crystallography", EXS. (1996), 75:185-222.
Vilardaga; et al., "Differential Conformational Requirements for Activation of G Proteins and the Regulatory Proteins Arrestin and G Protein-coupled Receptor Kinase in the G Protein-coupled Receptor for Parathyroid Hormone (PTH)/PTH-related Protein", The Journal of Biological Chemistry (2001), 276(36):33435-33443.

(Continued)

*Primary Examiner* — John Ulm
(74) *Attorney, Agent, or Firm* — Bozicevic, Field & Francis LLP; James S. Keddie

(57) ABSTRACT

Certain embodiments provide a method for crystallizing a GPCR. The method may employ a fusion protein comprising: a) a first portion of a G-protein coupled receptor (GPCR), where the first portion comprises the TM1, TM2, TM3, TM4 and TM5 regions of the GPCR; b) a stable, folded protein insertion; and c) a second portion of the GPCR, where the second portion comprises the TM6 and TM7 regions of the GPCR.

20 Claims, 28 Drawing Sheets
(7 of 28 Drawing Sheet(s) Filed in Color)

OTHER PUBLICATIONS

Vilardaga; et al., "Measurement of the millisecond activation switch of G protein-coupled receptors in living cells", Nature Biotechnology (2003), 21(7):807-812.

Yao; et al., "Crystallization and Preliminary X-Ray Structure Analysis of Pigeon Egg-White Lysozyme", J. Biochem. (1992), 111:1-3.

Geiser et ai, "Bacteriorhodops in chimeras containing the third cytoplasmic loop of bovine rhodopsin activate transducin for GTP/GDP exchange Protein", Science (2006), 15:1679-90.

Jaakola et al., "The 2.6 angstrom crystal structure of a human A2A adenosine receptor bound to an antagonist", Science (2008), 322:1211-1217.

Kim et al., Light-driven activation of beta 2-adrenergic receptor signaling by a chimeric rhodopsin containing the beta 2-adrenergic receptor cytoplasmic loops, Biochemistry (2005), 44:2284-92.

Tumova et al., "Insight into the mechanism of dopamine D1-like receptor activation. Evidence for a molecular interplay between the third extracellular loop and the cytoplasmic tail", J. Biol. Chem. (2003),278:8146-53.

Wess et al., "Identification of a small intracellular region of the muscarinic m3 receptor as a determinant of selective coupling to PI turnover", FEBS Lett. (1989), 258:133-6.

Wong et al., "Chimeric muscarinic cholinergic: beta-adrenergic receptors that activate Gs in response to muscarinic agonists", J. Biol. Chem. (1990), 265:6219-24.

Yamashita et al., "Distinct roles of the second and third cytoplasmic loops of bovine rhodopsin in G protein activation", J. Biol. Chem. (2000), 275:34272-9.

Byrne; et al., "Fusion protein approach to improve the crystal quality of cytochrome b03 ubiquinol oxidase from *Esscherichia coli*", Bioenergetics (2000), 1459(2-3):449-455.

Kobilka; et al., "Conformational complexity of G-protein-coupled receptors", Trends in Pharmacological Sciences (2007),28(8):397-406.

Topiol; et al., "X-ray structure breakthroughs in the GPCR transmembrane region", Biochemical Pharmacology (2009),78(1):11-20.

Wang; et al., "Identification of a domain in the angiotensin II type 1 receptor determining G-q coupling by the use of receptor chimeras", Journal of Biological Chemistry (1995),270(28):16677-16682.

Yu; et al., "Global chimeric exchanges within the intracellular face of the bradykinin B2 receptor with corresponding angiotensin II type Ia receptor regions: Generation of fully functional hybrids showing characteristic signaling of the ATIa receptor", Journal of Cellular Biochemistry (2002),85(4):809-819.

U.S. Appl. No. 60/999,951, filed Oct. 22, 2007, 79pgs.
U.S. Appl. No. 61/000,325, filed Oct. 24, 2007, 89pgs.
U.S. Appl. No. 61/060,107, filed Jun. 9, 2008, 108pgs.
U.S. Appl. No. 61/194,961, filed Oct. 1, 2008, 173pgs.

beta2AR-T4L
Length 501 aa
MW 56764

Amino acid sequence (T4 lysozyme is in CAPS) (SEQ ID NO:1):

dykddddamgqapgngsaflllapnrshapdhdvtqqrdevwvvgmgivmslivlaivgnvlvitaiakferlqtvtnyfitslacadlvmg
lavvpfgaahilmkmwtfgnfwcefwtsidvlcvtasietlcviavdryfaitspfkyqsiltknkarvillmvwivsgltsflpiqmhwyrath
qeaincyaeetccdfftnqayaiassivsfyvplvimvfvysrvfqeakrqlNIFEMLRIDEGLRLKIYKDTEGYYTIGIGHL
LTKSPSLNAAKSELDKAIGRNTNGVITKDEAEKLFNQDVDAAVRGILRNAKLKPVYDSLDAVRRA
ALINMVFQMGETGVAGFTNSLRMLQQKRWDEAAVNLAKSRWYNQTPNRAKRVITTFRTGTWD
AYkfclkehkalktlgiimgtlrtlcwlpffivnivhviqdnlirkevyillnwigyvnsgfnpliycrspdfriatqellclrrsslkayqnqyssnqn
tgeqsg Note: the full translation product of the gene below also contains the signal peptide sequence
mktiialsyifclvfa at the N-terminus, which gets cleaved by signal peptidase during expression.

Fig. 9A

DNA sequence for beta2AR-T4L (SEQ ID NO:2):

ATGAAGACGATCATCGCCCTGAGCTACATCTTCTGCCTGGTGTTCGCCGACTACAAGGAGGATGATGACGCCA
TGGGGCAACCCGGGAACGGCAGCGCCTTCTTGCTGGCACCCAATAGAAGCCATGCGCCGGACCACGACGTCA
CGCAGCAAAGGACGAGGTGTGGTGGTGATGGGCATGGCCTTCATGTCTCTCATCGTCCTGGCCATCGTGT
TTGGCAATGTGCTGGTCATCACAGCCATTGCCAAGTTCGAGCGTCTGCAGACGGTCACCAACTACTTCATCACT
TCACTGGCCTGTGTGCTGATCTGGTCATGGGCCTGGCAGTGGTCCCTTTGGGCGCCGCCATATTCTTATGAAAA
TGTGGACTTTTGCGAACTTCTGGTGCGAGTTTGGACTTCCATTGATGTGCTGTGCGTCACGGCCAGCATTGAG
ACCCTGTGCGTGATCGCAGTGGATCGCTACTTTGCCATTACTTCACCTTTCAAGTACCAGAGCCTGCTGACCAA
GAATAAGGCCCGGGTGATCATTCTGATGGTGTGGATTGTGTCAGGCCTTACTCCTTTGCCATTCAGATGC
ACTGGTACCGGGCCACCCACCAGGAAGCCATCAACTGCTATGCTAGCGAGACCTGCTGTGACTTCTTCACGAA
CCAAGCCTATGCCATTGCCTTCAGGAGGCCAAAAGGCAGCTCAACATCTTCGAGATGCTGCGCATCGACGAGAA
GGGTCTTTCAGGAGGACACCGAAGGTCTGAACTGGACAAAGATGTAGATGCCGCGTCCGATCGGCACACCAACG
GATTTACAAGGACTCTGAACTGGACAAAGATGTAGATGCCGCGTCCGATCGGCACACCAACG
GTGCCAAGTCTGAACTGGACAAAGATGTAGATGCCGCGTCCGATCGGCACACCAACGGTTCATTACAAGGACGAGGCGGAGA
AACTCTTCAACCAAGATGTCTTCGCCGTGCAGCCTGCAGCCTGACATCAACATGGTTTCCAAATGGGCGAGCGGCAGTGAATTGGCTAAATCTCGCT
CTCCCTTGATGCTGTTCGCCGTGCAGCCTGCAGCCTGACATCAACATGGTTTCCAAATGGGCGAGCGGCAGTGAATTGGCTAAATCTCGCT
TTTACGAACTCCTGCGCATGCTCCAGAGAAGCGCTGCCAAGCCTGTCATCACTACCTTCCGTACTACCTTGGGACGCTTACAA
GGTACAATCAGACACTAACCGTGCCAAAGCCCTCAAGACGTTAGCATCATGGCATCATCATCGTAAGGAAGTTTACATCCTCCTAAAT
GTTCTGCTTGAAGGAGCACAAAGCCCTCAAGACGTTAGCATCATGGCACTTCACCCTCTGCTG
CCCTTCTTCATCGTTAACATTGTCATTCTGGTTTCAATTGCATTATCCCCTATCTACTACCGGGAGCCCAGATTTCAGGATTTGCCTTCCA
TGGATAGGCTATGTGCCTGCGCAGGTCTCTTTGAAGGCCTATGGGAATGGCTACTCCAGCAACGGCAACACAGGG
GAGCAGAGTGGA

Fig. 9B beta1AR-T4L
Length 527 aa
MW 58419

Amino acid sequence (T4 lysozyme is in CAPS) (SEQ ID NO:3):

dykddddagagalgasepcnlssaaplpdgaataarllvlaspaslpasegsaplsqqwtagmgllvalivlilivvgnvlvivaiaktprlqtltnlfim
slasadlvmgllvvpfgativwgrweygsffcelwtsvdvlcvtasietlcvialdrylaitspfryqslltraralvctvwaisalvsflplmhwwraesde
arrcyndpkccdfvtnrayaiassvvsfyvplcimafvylrvfreaqkqvNIFEMLRIDEGLRLKIYKDTEGYYTIGIGHLLTKSPSLN
AAKSELDKAIGRNTNGVITKDEAEKLFNQDVDAAVRGILRNAKLKPVYDSLDAVRRAALINMVFQMGETGVA
GFTNSLRMLQQKRWDEAAVNLAKSRWYNQTPNRAKRVITTFRTGTWDAYlvalreqkalktlgiimgvflcwlpfflanvv
kafhrdlvpdrlyfnwlgyansafnpiiycrspdfrkafqrllccarraacrraahgdlprasgclara CXCR4-T4L
Length 486 aa
MW 55313

Amino acid sequence (T4 lysozyme is in CAPS) (SEQ ID NO:4):

dykddddamegisiytsdnyteemgsgdydsmkepcfreenanfnkifliptlyslifltgivgnglvilvmgyqkklrsmtdkyrlhlsvadllfvitlpfwa
vdavanwyfgnflckavhviytvnlyssvllafislldrylalvhatnsqrprlkllaekvvygwvgwipallltipdflfanvseaddryicdrfypndlwvvfqfq
himvgllpgivilscyciliskNIFEMLRIDEGLRLKIYKDTEGYYTIGIGHLLTKSPSLNAAKSELDKAIGRNTNGVITKD
EAEKLFNQDVDAAVRGILRNAKLKPVYDSLDAVRRAALINMVFQMGETGVAGFTNSLRMLQQKRWDEAA
VNLAKSRWYNQTPNRAKRVITTFRTGTWDAYshskghqkrkalkttvillaffacwlpyyigisidsfillelikqgcefentvhkwisite
alatfhccinpilyaflgakfktsaqhalt

Fig. 9C

α1A Adrenergic receptor-T4 lysozyme fusion (SEQ ID NO:5)
dykdddamvflsgnasdssnctqppapvniskaillgviggllifgvlgnilvilsvachrlhsvthyyivnlavadlllstvlpfsaifevlgywafgrvfcni
waavdvlcctasimglcilsidryigvsyplryptivtqrrglmallcvwalsivisigplfgwrqpapedeticqineepgyvlfsalgsfylplailivmycrvy
vvakresNIFEMLRIDEGLRLKIYKDTEGYYTIGIGHLLTKSPSLNAAKSELDKAIGRNTNGVITKDEAEKLFNQD
VDAAVRGILRNAKLKPVYDSLDAVRRAALINMVFQMGETGVAGFTNSLRMLQQKRWDEAAVNLAKSRWY
NQTPNRAKRVITTFRTGTWDAYlkfsrekkaaktigivvgcfvlcwlpfflvmpigsffpdfkpsetvfkifvfwlgylnscinpiiypcssqefkk
afqnvlriqclcrkqsskhalgytlhppsqaveqqhkdmvripvgsretfyriskdgvcewkfssmprgsaritvskdqsscttarvrsksflqvcccvg
pstpsldknhqvptikvhtislsengeev α2A Adrenergic receptor-T4 lysozyme fusion (SEQ ID NO:6)
dykdddamgslqpdagnaswngteapgggaratpyslqvtltlvclagllmlltvfgnvlviiavftsralkapqnlflvslasadilvativipfslanevmg
ywyfgkawceiylaldvlfctssivhlcaislidrywsitqaieynlkrtpprrikailivwvisavisfpplisiekkgggggpqpaeprceindqkwyvisscig
sffapclimilvyvriyqiakrtNIFEMLRIDEGLRLRLKIYKDTEGYYTIGIGHLLLTKSPSLNAAKSELDKAIGRNTNGVITK
DEAEKLFNQDVDAAVRGILRNAKLKPVYDSLDAVRRAALINMVFQMGETGVAGFTNSLRMLQQKRWDEA
AVNLAKSRWYNQTPNRAKRVITTFRTGTWDAYgrqnrekrftfvlavigvfvvcwfpfffylltltavgcsvprtlfkffwfgycnsslnp
viytifnhdfrrafkkilcrgdrkriv D1 Dopamine receptor-T4 lysozyme fusion (SEQ ID NO:7)
dykdddamrtlntsamdgtglvverdfsvriltacflsllilstllgntlvcaavirfrhlrskvtnffvislavsdlllavivmpwkavaeiagfwpfgsfcniwva
fdimcstasinlcvisvdrywaisspfryerkmtpkaafililisvawtlsvlisfipvqlswhkakptspsdgnatslaetidncdssIsrtyaissvsIstyipv
aimivtytriyriaqkqiNIFEMLRIDEGLRLRLKIYKDTEGYYTIGIGHLLLTKSPSLNAAKSELDKAIGRNTNGVITKDEAE
KLFNQDVDAAVRGILRNAKLKPVYDSLDAVRRAALINMVFQMGETGVAGFTNSLRMLQQKRWDEAAVNLA
KSRWYNQTPNRAKRVITTFRTGTWDAYmsfkretkviktlsivimgvfvccwlpfflnclilpfcgsgetqpfcidsntfdvfvwfgwanssl
npiiyafnadfrkafstllgcyrlcpatnnaietvsinnngaamfsshheprgsiskecnlvliphavgssedlkkeeaagiarpleklspalsvildydtdv
slekiqpitqnqhpt

Fig. 9D

D2 Dopamine receptor-T4 lysozyme fusion (SEQ ID NO:8)
dykdddamdpInIswyddddlerqnwsrpfngsdgkadrphynyyatlltlliavifgnvlvcmavsrekalqtttnylivsla
vadllvatlvmpwvvylevvgewkfsrihcdifvtldvmmctasilnlcaisidrytavampmlyntryssskrrvtvmisivw
IsftiscpIlfglnnadqneclianpafvvyssivsfyvpfivtllvyikiyivlrrrNIFEMLRIDEGLRLKIYKDTEGY
YTIGIGHLLTKSPSLNAAKSELDKAIGRNTNGVITKDEAEKLFNQDVDAAVRGILRNAKL
KPVYDSLDAVRRAALINMVFQMGETGVAGFTNSLRMLQQKRWDEAAVNLAKSRWYN
QTPNRAKRVITTFRTGTWDAYlsqqkekkatqmlaivlgvfiicwlpffithilnihcdcnippvlysaftwlgyvn
savnpiiyttfniefrkafIkilhc M3 Muscarinic acetylcholine receptor-T4 lysozyme fusion (SEQ ID NO:9)
dykdddamtlhnnsttspIfpnIssswihspsdaglppgtvthfgsynvsraagnfsspdgtddplgghtvwqvvflaflg
lalvtignilvivsfkvnkqIktvnnyfllslacadliigvismnIftyiilmrwalgnlacdlwlaidyvasnasvmnllvisfdry
fsitrpltyrakrttkragvmiglawvisfvlwapailfwqyfvgkrtvppgecfiqflsepiitfgtaiaafympvtimtilywriyke
tekrtNIFEMLRIDEGLRLKIYKDTEGYYTIGIGHLLTKSPSLNAAKSELDKAIGRNTNGVIT
KDEAEKLFNQDVDAAVRGILRNAKLKPVYDSLDAVRRAALINMVFQMGETGVAGFTNS
LRMLQQKRWDEAAVNLAKSRWYNQTPNRAKRVITTFRTGTWDAYmslvkekkaaqtlsaill
afiitwtpynimvIvntfcdscipktfwnlgywlcyinstvnpvcyalcnktfrttfkmIllcqcdkkkrrkqqyqqrqpsvifhkra
peqal A1a Adenosine receptor-T4 lysosyzme fusion (SEQ ID NO:10)
dykdddampssisatfqaayigievIialsvpgnvIviwavkvnqalrdatfcfivslavadvavgalviplailinigpqtyfht
cImvacpviltqssilalIaiavdryIrvkiplryIkmvvtpraavalagcwilsfvvgitpmfgwnnIsaverawaangsmg
epviikcefekvismeymvyfnffvwvippillmvilyIevryfIirkqINIFEMLRIDEGLRLKIYKDTEGYYTIGI
GHLLTKSPSLNAAKSELDKAIGRNTNGVITKDEAEKLFNQDVDAAVRGILRNAKLKPVY
DSLDAVRRAALINMVFQMGETGVAGFTNSLRMLQQKRWDEAAVNLAKSRWYNQTPN
RAKRVITTFRTGTWDAYkyygkelkiakslaliIifialswIpIhilncitifqpschkpsilyiafifithgnsamnpivya
friqkfrvtflkiwndhfrcqpappidedlpeerpdd

Fig. 9E

H1 Histamine receptor-T4 lysosyzme fusion (SEQ ID NO:11)
Yykdddamslpnssclledkmcegnkttmaspqlmplvvvlsticlvtvgnllvlyavrserklhtvgnlyivslsvadlivgavvmpmnilylm
skwslgrplclfwlsmdyvastasifsvflicidryrsvqqplrylkyrktkrasatilgawflsflwvipilgwnhfmqqtsvrredkcetfydvtwfkv
mtaiinfylptllmwfyakiyakavrqhcNIFEMLRIDEGLRLKIYKDTEGYYTIGIGHLLLTKSPSLNAAKSELDKAIGR
NTNGVITKDEAEKLFNQDVDAAVRGILRNAKLKPVYDSLDAVRRAALINMVFQMGETGVAGFTNSLR
MLQQKRWDEAAVNLAKSRWYNQTPNRAKRVITTFRTGTWDAYlhmnrerkaakqlgfimaafilcwipyfifmviaf
cknccnehlhmftiwlgyinstinplryplcnenfkktfkrilhirs H2 Histamine receptor-T4 lysosyzme fusion (SEQ ID NO:12)
dykdddamapngtassfcldstackititvvlavllitvagnvvvclavglnrrlrnltncfivslaitdlllgilvlpfsaiyqlsckwsfgkvfcniytsldv
mlctaslinlfmisldrycavmdplrypvlvtpvrvaislvliwvistlsflsihgwnsmetskgnhttsckvqnevygivdgivtfylpllimcityy
rifkvardqaNIFEMLRIDEGLRLKIYKDTEGYYTIGIGHLLLTKSPSLNAAKSELDKAIGRNTNGVITKDEAEK
LFNQDVDAAVRGILRNAKLKPVYDSLDAVRRAALINMVFQMGETGVAGFTNSLRMLQQKRWDEAAV
NLAKSRWYNQTPNRAKRVITTFRTGTWDAYaatirehkatvtlaavmgafilcwfpyftafryrglrgddaineyleaivlwlgy
ansalnpilyaalndfrtgyqqlfccrlanmshktlsrnsasqlsrtqsrepraqeekpklqvwsgtevtapqgatdr 5HT1A Serotonin receptor-T4 lysosyzme fusion (SEQ ID NO:13)
dykdddamdvlspgqgnnttsppapfetggntlgisdvtvsyqvitslllgtlifcavlgnacvvaaialerslqnvanyligslavtdlmvsvlvpm
aalyqvlnkwtlgqytcdlfialdvlcctssilhlcaialdrywaitdpidynkrtprraaalisltwlgflsippmigwrtpedrsdpdactiskdhgyti
ystfgafyiplllmlvlygrifraarfrlNIFEMLRIDEGLRLKIYKDTEGYYTIGIGHLLLTKSPSLNAAKSELDKAIGRNTN
GVITKDEAEKLFNQDVDAAVRGILRNAKLKPVYDSLDAVRRAALINMVFQMGETGVAGFTNSLRMLQ
QKRWDEAAVNLAKSRWYNQTPNRAKRVITTFRTGTWDAYmalarerktvktiglimgtflicwlpffivalvlpfcessch
mptllgaiinwlgysnsllnpviyayfnkdfqnafkklikckfcrq

Fig. 9F

5HT1D Serotonin receptor-T4 lysosyzme fusion (SEQ ID NO:14)
YykdddamsplnqsaeglpqeasnrsInatetseawdprtlqalkislavvIsvitlatvIsnafvItItIItlrkIhtpanyligslattdIIvsiI
vmpislaytlthwnfgqilcdlwlssditcctasIIhlcvialdrywaitdaleyskrrtaghaatmiaiwvaisicisppIfwrqakaqee
msdclvntsqisytlystcgafyipsvIIlilygriyraamriNIFEMLRIDEGLRLKIYKDTEGYYTIGIGHLLTKSPSL
NAAKSELDKAIGRNTNGVITKDEAEKLFNQDVDAAVRGILRNAKLKPVYDSLDAVRRAALINM
VFQMGETGVAGFTNSLRMLQQKRWDEAAVNLAKSRWYNQTPNRAKRVITTFRTGTWDAYis
aarekatkilgiligafiicwlpffvvsIvlpicrdscwihpaltdfftfwlgylnslinpliytvfneefrqatqkivpfrkas 5HT2A Serotonin receptor -T4 lysosyzme fusion (SEQ ID NO:15)
dykdddamdilceentsIssttnsImqinddtrlysndfrnsgeantsdafnwtvdsenrtnIscegclspscIsIIhlqeknwsalltav
viiltiagnilvimavslekkIqnatnyfImsIaiadmIIgftvmpvsmlItilygyrwplpskIcavwiyldvlfstasimhIcaisIdryvaiq
npihhsrfnsrtkafIkiiavwtisvgismpipvfgiqpddskvfkegscIIaddnfvligsfvsffipltimvityfItiksIqkeaNIFEMLRI
DEGLRLKIYKDTEGYYTIGIGHLLTKSPSLNAAKSELDKAIGRNTNGVITKDEAEKLFNQDVDA
AVRGILRNAKLKPVYDSLDAVRRAALINMVFQMGETGVAGFTNSLRMLQQKRWDEAAVNLA
KSRWYNQTPNRAKRVITTFRTGTWDAYqsisneqkackvigivififvvmwcpfifinimavickescnedvigalin
vfvwigyIssavnplvytIfnktyrsafsryiqcqykenkkpIqlivntipalayksslqmgqkknskqdaktitdndcsmvalgkqh
seeaskdnsdgvnekvscv Prostacyclin receptor (SEQ ID NO:16)
dykdddamadscrnltyvrgsvgpatstlmfvagvvgnglalgilsarrparpsafaviivtglaatdilgtsfIspavfvayarnssIIgia
rggpalcdafatamtfrglasmlifamaverclaIshpyIyaqldgprcarIapaiyafcvIfcaIplIgqhqqycpgswcfIrmwa
qpggaafslayaglvaiIvaaifIcngsvtIsIcrmNIFEMLRIDEGLRLKIYKDTEGYYTIGIGHLLTKSPSLNAA
KSELDKAIGRNTNGVITKDEAEKLFNQDVDAAVRGILRNAKLKPVYDSLDAVRRAALINMVFQ
MGETGVAGFTNSLRMLQQKRWDEAAVNLAKSRWYNQTPNRAKRVITTFRTGTWDAYrtgede
vdhIiIIaImtvvmavcsIpIitircftgavapdsssemgdIIafrfyafnplIdpwvfiIrkavfqrikwvcclcgpahgdsqtplsqlas
grrdprapsapvgkegscvplsawgegqveplpptqssgsavgtsskaeasvacsIc

Fig. 9G

Prostaglandin F2α receptor-T4 lysozyme fusion (SEQ ID NO:17)
dykdddamsmnnskalvspaaalisnttcatenrlsvffsvifmtvgilisnslaialimkayarfrqkskasflllasqlvltdffqhlingaiavfvasd
kewirfdqasnylcsifqicmvfsqlcpllIgasvmaiercigvrtkoifhstkitsIkhvkmmIsqvclfavfialipilqIhrdvkiqasrtwcfvntedIkdwe
drfylilfsflqllaIqvsIlcnaltgitIllrvNIFEMLRIDEGLRLKIYKDTEGYYTIGIGHLLTKSPSLNAAKSELDKAIGRNTN
GVITKDEAEKLFNQDVDAAVRGILRNAKLPVYDSLDAVRRAALINMFQMGETGVAGFTNSLRMLQQ
KRWDEAAVNLAKSRWYNQTPNRAKRVITTFRTGTWDAYggrshhlemviglaimcvscicwspfivtmanigingnhsl
etcettIfaIrmatwnqlildpwvyiIfkavlikniykiasqccqvhvislhiwelssiknsIlkvaaIsespvaeksast Prostaglandin E2 EP1 receptor-T4 lysozyme fusion (SEQ ID NO:18)
dykdddamspocapInIslageattcaapwvpntsavppsqaspalpifsmtIgavsnllaIaIlaqaaagrlrrrsaatflIfvasIlatdIaghvipgal
vIrIvtagrapaggachflggcmvffgIqIcpllIgacmaverqcvqvtrplIhaarvsvaralaavaavavaIalavallpIarvarvelqvpatwcfiqIapp
ggwrqallagilfasidIvalvacntlsqllaIlIraNIFEMLRIDEGLRLKIYKDTEGYYTIGIGHLLTKSPSLNAAKSELDKAI
GRNTNGVITKDEAEKLFNQDVDAAVRGILRNAKLPVYDSLDAVRRAALINMFQMGETGVAGFTNSL
RMLQQKRWDEAAVNLAKSRWYNQTPNRAKRVITTFRTGTWDAYrarahdvemvgalvgaImvvscicwspmIvIva
IavgqwsstsIqrpItfIavrIaswnqiIidpwvyllIrqavIrqIIrlIppragakgpapadlgItpsaweasstrssrhsqlshf CNR1 Cannabinoid receptor-T4 lysozyme fusion (SEQ ID NO:19)
dykdddamksildqIadttfrtittdllvgsndiqyedikqdmasklqyfpqkfrpItsfrgspfgekmtagdnpqIvpadqvnitefynksIssfken
eeniqcgenfmdiecfmvInpsqqIaIaiavsItIgattvIenIvIcvilhsrslrcrpsyhfigsIavadlIgsvifvysfidfhvfhrkdsImvflfkIgavtas
ftasvvsIffIaldryisihrpIavkrIvtrpkavvafcImwtIaiviavipIIgwnceklqsvcsdifphideltvImfwigvtsvIlIifvvaymvlIwkahsh
NIFEMLRIDEGLRLKIYKDTEGYYTIGIGHLLTKSPSLNAAKSELDKAIGRNTNGVITKDEAEKLFNQDVDA
AVRGILRNAKLPVYDSLDAVRRAALINMFQMGETGVAGFTNSLRMLQQKRWDEAAVNLAKSRWYN
QTPNRAKRVITTFRTGTWDAYdqarmdirIaktivIlIvwgpllaimvydfqkmniklIktvfafcsmIcInstvnpIjivaIrskdIrh
afrsmfpsceqtaqpIdhnsmqdsdcIhkhannaasvhraaescikstvkiakvtmsvstdtsaeal

Fig. 9H

Endothelin-1 receptor-T4 lysozyme fusion (SEQ ID NO:20)

dykdddadnperystnlsnhvddtfttrngtelsflvtthaptnlvlpsngsmhnycpqqtkitsafkyintvlscitifivgmvgnatllrilyqnkcmrng pnallaslalgdllyvvidlpinvfkllagrwpfdhndfgvfcklfpflqkssvgitvlnlcalsvdryravaswsrvqgigiplvtaleivsiwilsfllaipea igfvmvpfeyrgeqhktcmlnatskfmefyqdvkdwwlfgfyfcmplvctaifytlmtceminrrNIFEMLRIDEGLRLKIYKDTEGY YTIGIGHLLTKSPSLNAAKSELDKAIGRNTNGVITKDEAEKLFNQDVDAAVRGILRNAKLKPVYDSLDAV RRAALINMVFQMGETGVAGFTNSLRMLQQKRWDEAAVNLAKSRWYNQTPNRAKRVITTFRTGTWDA YehlkqrrevaktvfclvvifalcwfplhlsrilkktvynemdknrcellsflllmdyiginlatmnscimplalyfvskkfkncfqsclcccyqsksImt svpmngtsiqwknhdqnnhntdrsshkdsmn Gonadotropin-releasing hormone receptor-T4 lysozyme fusion (SEQ ID NO:21)

Fykdddamansaspeqnqhcsainnsiplmgqniptltlsgkirvtvtfflllsatfnasfllkiqlkwtqkkekgkkisrmkllikhltlanlletlivm pldgmwnitvqwyagelickvlsylklfsmyapafmmwislaitrplakvsnskvgasmvglawillssvfagpqlyifrmihladssgqtkv NIFEMLRIDEGLRLKIYKDTEGYYTIGIGHLLTKSPSLNAAKSELDKAIGRNTNGVITKDEAEKLFNQDVD AAVRGILRNAKLKPVYDSLDAVRRAALINMVFQMGETGVAGFTNSLRMLQQKRWDEAAVNLAKSRW YNQTPNRAKRVITTFRTGTWDAYniprariktikmtvafatstrvcwtpyyvlgiwywfdpeminrisdpvnhfffifalinpcfdpliyg yfsl Oxytocin receptor-lysozyme fusion (SEQ ID NO:22)

dykdddamegalaanwsaeaanasaappgaegnrtagpprrnealarvevavlcllilialsgnacvllalrttrgkhsriffmkhlsiadlvvavf qvlpqllwdltfrygpdllcrlvkylqvvgmfastylllimsldrclaicqplrslrrtdrlavlatwlgclvasapqvhlfslrevadgvfdcwavfiqpwg pkayitwitlavylvpvilaacygllsfkiwqnlNIFEMLRIDEGLRLKIYKDTEGYYTIGIGHLLTKSPSLNAAKSELDKA IGRNTNGVITKDEAEKLFNQDVDAAVRGILRNAKLKPVYDSLDAVRRAALINMVFQMGETGVAGFTNS LRMLQQKRWDEAAVNLAKSRWYNQTPNRAKRVITTFRTGTWDAYliskakirtvkmtfiivlafivcwtpffvqmwsv wdanapkeasafiivmllaslnsccnpwiymlftghlfhelvqrflccsasylkgrrlgetsaskksnsssfvlshsrsssqpscsqpsta

Fig. 9I

MC4R Melanocortin receptor-T4 lysozyme fusion (SEQ ID NO:23)
dykdddamvnsthrgmhtslhlwnrssyrlhsnaseslgkgysdggcyeqlfvspevfvtlgvisllenilvivaiaknknlhspmyfficslavadmlvs
vsngsetivitilnstdtdaqsftvnidnvidsvicssllasicsllsiavdnryftifyalqyhnimtvkrvrgiiiisciwaactvsgilfiiysdssaviiclitmfftmlal
maslyvhmflmarlhiNIFEMLRIDEGLRLKIYKDTEGYYTIGIGHLLTKSPSLNAAKSELDKAIGRNTNGVITKDEA
EKLFNQDVDAAVRGILRNAKLKPVYDSLDAVRRAALINMVFQMGETGVAGFTNSLRMLQQKRWDEAAVNL
AKSRWYNQTPNRAKRVITTFRTGTWDAYirqganmkgaitltliligvfvvcwapffihlifyiscpqnpycvcfmshfnlyllimcnsiidp
liyalrsqelrktfkeiiccyplggglicdlssry NPY1 Neuropeptide Y receptor-T4 lysosyzme fusion (SEQ ID NO:24)
dykdddamnstlifsqvenhsvhsnfseknaqllafenddchlplamiftlalaygaviilgvsgnlaliiilkqkemrnvtnliivnlsfsdllvaimclptftvy
tlmdhwvfgeamcklnpfvgcvsitvsifslvlliaverhqliinprgwrpnnrhayvrgiaviwvlavasslptfliyqvmtdepfqnvtldaykdkyvcfdqtp
sdshrlsyttlllvlqyfgplctificyfkiyirlkrnNIFEMLRIDEGLRLKIYKDTEGYYTIGIGHLLTKSPSLNAAKSELDKAIGR
NTNGVITKDEAEKLFNQDVDAAVRGILRNAKLKPVYDSLDAVRRAALINMVFQMGETGVAGFTNSLRMLQ
QKRWDEAAVNLAKSRWYNQTPNRAKRVITTFRTGTWDAYrssetkrinimllsivvafavcwlpltfntvfdwnhqiiatcnhn
lllflchltamistcvnpifygflnknfqrdlqffnfcdfrsrdddyetiamstmhtdvsktslkqaspvafkkinnnddneki μ-Opioid receptor-T4 lysozyme fusion (SEQ ID NO:25)
dykdddamdssaaptnasnctdalaysscspapsgswvnlshldgnlsdpcgpnrtdlgrdslcpptgspsmitaitimalysivcvvglfgnflv
myvivrytkmktatniyifnlaladalstlpfqsvnylmgtwpfgtilckivisidynmftsiftlctmsvdryiavchpvkaldfrtpmakiinvcnwilssa
iglpvmfmattkyrqgsidctlfshptwywenllkicvfifafimpvlilltvcyglmilrlksvrNIFEMLRIDEGLRLKIYKDTEGYYTIGIGHL
LTKSPSLNAAKSELDKAIGRNTNGVITKDEAEKLFNQDVDAAVRGILRNAKLKPVYDSLDAVRRAALINMVF
QMGETGVAGFTNSLRMLQQKRWDEAAVNLAKSRWYNQTPNRAKRVITTFRTGTWDAYekdrnlrritrmvivvv
avfivcwtpihiyvikalvtipettfqtvswhfcialgytnsclnpvlyaftldenfkrcfrefciptssnieqqnstrirqntrdhpstantvdrtnhqlenleaeta
plp

Fig. 9J

κ-opioid receptor-T4 lysosyzme fusion (SEQ ID NO:26)

dykdddamdspiqifrgepgptcapsaclppnssawfpgwaepdsngsagsedaqlepahispaipviitavysvvfvvglvgnslvmfviirytkmktatni yifnlaladalvttmpfqstvylmnswpfgdvlckivisidyynmftsifltlmmsvdlryiavchpvkaldfrtplkakiinciwllssssvgisaiviggtkvredvdvie cslqfpdddyswwdlfmkicvfifafvipvliiivcytlmirlksvrINIFEMLRIDEGLRLKIYKDTEGYYTIGIGHLLTKSPSLNAAKSELD KAIGRNTNGVITKDEAEKLFNQDVDAAVRGILRNAKLPVYDSLDAVRRAALINMFQMGETGVAGFTNSLRMLQ QKRWDEAAVNLAKSRWYNQTPNRAKRVITTFRTGTWDAYekdnlrritrlvlvvavfvvcwtpihifilvealgstshstaalssyyfcial gytmsslnpilyafldenfkrcfrdfcfplkmrmerqstsrvmtvqdpaylrdidgmnkpv δ-opioid receptor-T4 lysosyzme fusion (SEQ ID NO:27)

dykdddamepapsagaelqpplfanasdayspsfpsaganasgppgarsasslalaiatalysavcavgllgnvlvmfgivrytkmktatniyifnlaladala tstlpfqsakylmetwpfgellckavisidyynmftsifltlmmsvdlryiavchpvkaldfrtpakakliniciwlasgvgvpimvmavtrprdgavvcmlqfpsp swyrwdhvtkicvfifafvvpliliitvcygimlirlrsvrNIFEMLRIDEGLRLKIYKDTEGYYTIGIGHLLTKSPSLNAAKSELDKAIGRNT NGVITKDEAEKLFNQDVDAAVRGILRNAKLPVYDSLDAVRRAALINMFQMGETGVAGFTNSLRMLQQKRWD EAAVNLAKSRWYNQTPNRAKRVITTFRTGTWDAYekdrslrritmvlvvvgafvvcwapihifviwvtlvdidrdplvvaalhlcialgyans slnpvlyafldenfkrcfrqlcrkpcgrpdpssfsrareatarervtactpsdgpggggaa SSR2 Somatostatin receptor-T4 lysosyzme fusion (SEQ ID NO:28)

dykdddamdmadepIngshtwlsipfdlngsvvstntsnqtepyydlitsnavltfifyfvvcliglcgntlviylvilryakmktitniyllnlaiadelfmlglpflamqval vlhwpfgkalcrvmtvdglnaftslfcltvmsidrylavhpiksakwrrprtakmitmavwgvsllvlipimiyaglrsnqwgrssctinwpgesgawytgfilytfi lgflvplticlcyfflliillkvkssgNIFEMLRIDEGLRLKIYKDTEGYYTIGIGHLLTKSPSLNAAKSELDKAIGRNTNGVITKDEAEK LFNQDVDAAVRGILRNAKLPVYDSLDAVRRAALINMFQMGETGVAGFTNSLRMLQQKRWDEAAVNLAKSRW YNQTPNRAKRVITTFRTGTWDAYkrkksekkvtrmvsivvavfifcwlpfyifnvssvsmaisptpalkgmfdfvvvityanscanpilyaflsdnfk ksfqnvlclvkvsgtddgersdskqdksrlnettetqrtlngdlqtsi

Fig. 9K

Somatostatin receptor-T4 lysosyzme fusion (SEQ ID NO:29)
dykdddameplfpastpswnasspgaasgggdnrtlvgpapsagaravlvpvlyllvcaaglggntilvivyvlrfakmktvtnlylnla
vadvlymlglpflatqnaasfwpfgpvlcrlvmtldgvnqftsvfcltvmsvdrylavvhplssarwrrprvaklasaaawvlslcmslpll
vfadvqeggtcnaswpepvglwgavfilytavlgftapllvlclcyllivvkvraagNIFEMLRIDEGLRLKIYKDTEGYYTIG
IGHLLTKSPSLNAAKSELDKAIGRNTNGVITKDEAEKLFNQDVDAAVRGILRNAKLKPVYDSLDA
VRRAALINMVFQMGETGVAGFTNSLRMLQQKRWDEAAVNLAKSRWYNQTPNRAKRVITTFRT
GTWDAYvrrrserkvtrmlvvvlvfagcwlpftvnivnlavalpqepasaglyftvvilsyanscanpvlygflsdnlrqsfqkvlclrk
gsgakdadateprpdrirqqeatppahraaanglmqtskl AGTR1 Angiotensin receptor-T4 lysosyzme fusion (SEQ ID NO:30)
dykdddaminsstedgikriqddcpkagrhnylfvmiptlysiifvvglfgnslvivlyfymklktvrasvflinlaladlcflltiplwavyta
meyrwpfgnylckiasasvsfnlyasfllttclsidrylalivhpmksllrtrmlvakvtclilwllaglaslpalihrnvflientnitvcafhyesq
nstlplgllgltkniIgflitpflillltsytlllwkalkkayNIFEMLRIDEGLRLKIYKDTEGYYTIGIGHLLTKSPSLNAAKSE
LDKAIGRNTNGVITKDEAEKLFNQDVDAAVRGILRNAKLKPVYDSLDAVRRAALINMVFQMGET
GVAGFTNSLRMLQQKRWDEAAVNLAKSRWYNQTPNRAKRVITTFRTGTWDAYknkprnddifkiim
aivlfffswiphqiftfldvliqlglijrdcriadivdtampiticiayfnnclnplfygflgkkfkryflqllkylppkakshsnlskmstlsyrpsdn
vssstkkpapcfeve LT4R1 Leukotriene B4 receptor-T4 lysosyzme fusion (SEQ ID NO:31)
dykdddamnttssaappslgvefisllallllsvalavglpgnsfvvwsilkmqkrsvtalmvlnlaladlavlltapfflhflaggtwsfgla
gcrichyvcgvsmyasvllltamsldrslavarpfvsqklrtkamarrvlagiwvlsfllatpvlayrtvpwktnmslcfprypseghrafh
lifeavtgfllpflawasysdigrrlqarrNIFEMLRIDEGLRLKIYKDTEGYYTIGIGHLLTKSPSLNAAKSELDK
AIGRNTNGVITKDEAEKLFNQDVDAAVRGILRNAKLKPVYDSLDAVRRAALINMVFQMGETGVA
GFTNSLRMLQQKRWDEAAVNLAKSRWYNQTPNRAKRVITTFRTGTWDAYfrrsrrtgrivvliiltfaafwl
pyhvvnlaeagralagaaglgvgkrlslarnvliialalslsssvnplvyacagggllrsagvgfvakllegtgseasstrrggslgqtarsg
paalepgpseslltasspIklneIn

Fig. 9L

PAR1 Proteinase-activated receptor-T4 lysosyzme fusion (SEQ ID NO:38)

dykdddarrpeskatnatldprsfllrnpndkyepfwedeeknesglteyrlvsinksspIqkqIpafisedasgyltsswltifvpsvytgvfvvslpIni
maivvfillkmkvkpavvymlhatadvlfvslpfkisyyfsgsdwqfgselcrfvtaafycnmyaslllmtvisidrflavvypmqslswrtlgrasftcl
aiwalaiagvvplllkeqtiqvpglnittchdvlnetllegyayyfsafsavffvpllistvcyvsiircIsssaNIFEMLRIDEGLRLKIYKDTEG
YYTIGIGHLLTKSPSLNAAKSELDKAIGRNTNGVITKDEAEKLFNQDVDAAVRGILRNAKLKPVYDSLDAVR
RAALINMVFQMGETGVAGFTNSLRMLQQKRWDEAAVNLAKSRWYNQTPNRAKRVITTFRTGTWDAYanr
skksralflsaavfcifilcfgptmvlliahysflshtstteaayfayllcvcvssisccidpliyyassecqryvysilcckessdpssynssgqlmaskmdt
cssnlnnslykkllt mGluR4 Metabotropic glutamate receptor-T4 lysosyzme fusion (SEQ ID NO:32)

dykdddakpkghphmnsiridgdltlgglfpvhgrgsegkpcgelkkekgihrleamlfaldrinnqpdllpnltgarildtcsrdthaleqsltifvqaliek
dgtevrcgsgppplitkpervvgvigasgssvsimvanilrIfkipqisyastapdlsdnsrydffsrvvpsdtyqaqamdivralkwnyvstvasegs
ygesgveafiqksredggvciaqsvkiprepkagefdkiirrlletsnaravlifaneddirvleaarranqtghffwmgsdswgskiapvlhleevaeg
avtllpkrmsvrgfdryfssrtIdnrnrnwfaefwednfhcklsrhalkkgshvkkctnrerigqdsayeqegkvqfvidavyamghalhamhrdlcp
grvglcprmdpvdgtqllkyirnvnfsgiagnpvtfnengdapgrydyqlmdsaeykvigswtdhlhriermhwpgsgqlprslcslpcapge
rkktvkgmpccwhcepctgyaqyqvdrytcktcpydmrptenrtgcrpipilklewgspwavipllflavvgiaatlfvvitfvrryndtpivkasgrelsyvll
agiflcyattflmiaepdIgtcsIrritflglgmsisyaallltktnriyriteqgkrsvsaprispasqlaitfslisIqllgicvwfvvdpshsvvdfqdqrtIdprfar
gvlkcdisdsIsIlclgysmllmvctcvyaiktrgvpeNIFEMLRIDEGLRLKIYKDTEGYYTIGIHLLTKSPSLNAAKSELDKA
IGRNTNGVITKDEAEKLFNQDVDAAVRGILRNAKLKPVYDSLDAVRRAALINMVFQMGETGVAGFTNSLR
MLQQKRWDEAAVNLAKSRWYNQTPNRAKRVITTFRTGTWDAYtfneakplgfmyttciwviafipifgtsqsadklyiqtttl
tvsvslsasvslgmlympkvyilifhpeqnvpkrkrslkavvtaatmsnkftqkgnfrpngeakselcenleapalatkqtytytnhai

Fig. 9M

Bovine Pancreatic Trypsin Inhibitor (SEQ ID NO:33)
RPDFCLEPPYTGPCKARIIRYFYNAKAGLCQTFVYGGCRAKRNNFKSAEDCMRTCGGA Bovine Calbindin D9K (SEQ ID NO:34)
MKSPEELKGIFEKYAAKEGDPNQLSKEELKLLLQTEFPSLLKGPSTLDELFEELDKNGDGEVSFEEFQV
LVKKISQ Barnase (SEQ ID NO:35)
MAQVINTFDGVADYLQTYHKLPDNYITKSEAQALGWVASKGNLADVAPGKSIGGDIFSNREGKLPGKS
GRTWREADINYTSGFRNSDRILYSSDWLIYKTTDHYQTFTKIR Xylanase II from Trichoderma reesei (SEQ ID NO:36)
ETIQPGTGYNNGYFYSYWNDGHGGVTYTNGPGGQFSVNWSNSGNFVGGKGWQPGTKNKVINFSGS
YNPNGNSYLSVYGWSRNPLIEYYIVENFGTYNPSTGATKLGEVTSDGSVYDIYRTQRVNQPSIIGTATF
YQYWSVRRNHRSSGSVNTANHFNAWAQQGLTLGTMDYQIVAVEGYFSSSGSASITVS Thermostable Glucokinase from Pyrococcus furiosus (SEQ ID NO:37)
MPTWEELYKNAIEKAIKSVPKVKGVLLGYNTNIDAIKYLDSKDLEERIIKAGKEEVIKYSEELPDKINTVSQ
LLGSILWSIRRGKAAELFVESCPVRFYMKRWGWNELRMGGQAGIMANLLGGVGVPVIVHVPQLSRL
QANLFLDGPIYVPTLENGEVKLIHPKEFSGDEENCIHYIYEFPRGFRVFEFEAPRENRFIGSADDYNTTLF
IREEFRESFSEVIKNVQLAILSGLQALTKENYKEPFEIVKSNLEVLNEREIPVHLEFAFTPDEKVREEILNV
LGMFYSVGLNEVELASIMEILGEKKLAKELLAHDPVDPIAVTEAMLKLAKKTGVKRIHFHTYGYYLATEY
KGEHVRDALLFAALAAAAKAMKGNITSLEEIREATSVPVNEKATQVEEKLRAEYGIKEGIGEVEGYQIAFI
PTKIVAKPKSTVGIGDTISSSAFIGEFSFTL

Fig. 16

METHOD AND COMPOSITION FOR CRYSTALLIZING G PROTEIN-COUPLED RECEPTORS

GOVERNMENT RIGHTS

This invention was made with Government support under contracts NS028471 & GM075811 awarded by the National Institutes of Health. The Government has certain rights in this invention.

BACKGROUND

G protein-coupled receptor (GPCR) signaling plays a vital role in a number of physiological contexts including, but not limited to, metabolism, inflammation, neuronal function, and cardiovascular function. For instance, GPCRs include receptors for biogenic amines, e.g., dopamine, epinephrine, histamine, glutamate, acetylcholine, and serotonin; for purines such as ADP and ATP; for the vitamin niacin; for lipid mediators of inflammation such as prostaglandins, lipoxins, platelet activating factor, and leukotrienes; for peptide hormones such as calcitonin, follicle stimulating hormone, gonadotropin releasing hormone, ghrelin, motilin, neurokinin, and oxytocin; for non-hormone peptides such as beta-endorphin, dynorphin A, Leu-enkephalin, and Met-enkephalin; for the non-peptide hormone melatonin; for polypeptides such as C5a anaphylatoxin and chemokines; for proteases such as thrombin, trypsin, and factor Xa; and for sensory signal mediators, e.g., retinal photopigments and olfactory stimulatory molecules.

GPCRs are of immense interest for drug development.

SUMMARY OF THE INVENTION

A fusion protein is provided. In certain embodiments, the fusion protein comprises: a) a first portion of a G-protein coupled receptor (GPCR), where the first portion comprises the TM1, TM2, TM3, TM4 and TM5 regions of the GPCR; b) a stable, folded protein insertion, e.g., the amino acid sequence of lysozyme; and c) a second portion of the GPCR, where the second portion comprises the TM6 and TM7 regions of the GPCR. The polypeptide may be employed in crystallization methods, for example.

In certain embodiments, the stable, folded protein insertion is a polypeptide than can fold autonomously in a variety of cellular expression hosts, and is resistant to chemical and thermal denaturation. In particular embodiments, the stable folded protein insertion may be a protein that is known to be highly crystallizable, in a variety of space groups and crystal packing arrangements. In certain cases, the stable, folded protein insertion may also shield the fusion protein from proteolysis between the TM5 and TM6 domains, and may itself be protease resistant. Lysozyme is one such polypeptide, however many others are known.

Also provided is a nucleic acid encoding the above described fusion protein, and a cell comprising the same. The fusion protein may be disposed on the plasma membrane of the cell.

Also provided are crystals comprising the above described fusion protein, folded into an active form.

The above-described cell may be employed in a method comprising: culturing the cell to produce the fusion protein; and isolating said fusion protein from the cell. The method may further comprise crystallizing the fusion protein to make crystals which, in certain embodiments, may involve combining the fusion protein with lipid prior to crystallization. In certain embodiments, the fusion protein is crystallized using a bicelle crystallization method or a lipidic cubic phase crystallization method. The method may further comprise obtaining atomic coordinates of the fusion protein from the crystal.

Also provided is a method of determining a crystal structure. This method may comprise receiving an above described fusion protein, crystallizing the fusion protein to produce a crystal; and obtaining atomic coordinates of the fusion protein from said crystals. In other embodiments, the method may comprise forwarding a fusion protein to a remote location where the protein may be crystallized and analyzed, and receiving the atomic coordinates of the fusion protein.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 9A-9M shows the amino acid and nucleotide sequences of exemplary lysozyme fusion proteins.

FIG. 16 shows exemplary sequences that may be employed in place of the lysozyme sequences of FIG. 9.

DEFINITIONS

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with general dictionaries of many of the terms used in this disclosure. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole. Accordingly, the terms defined immediately below are more fully defined by reference to the specification as a whole.

Figure 1:
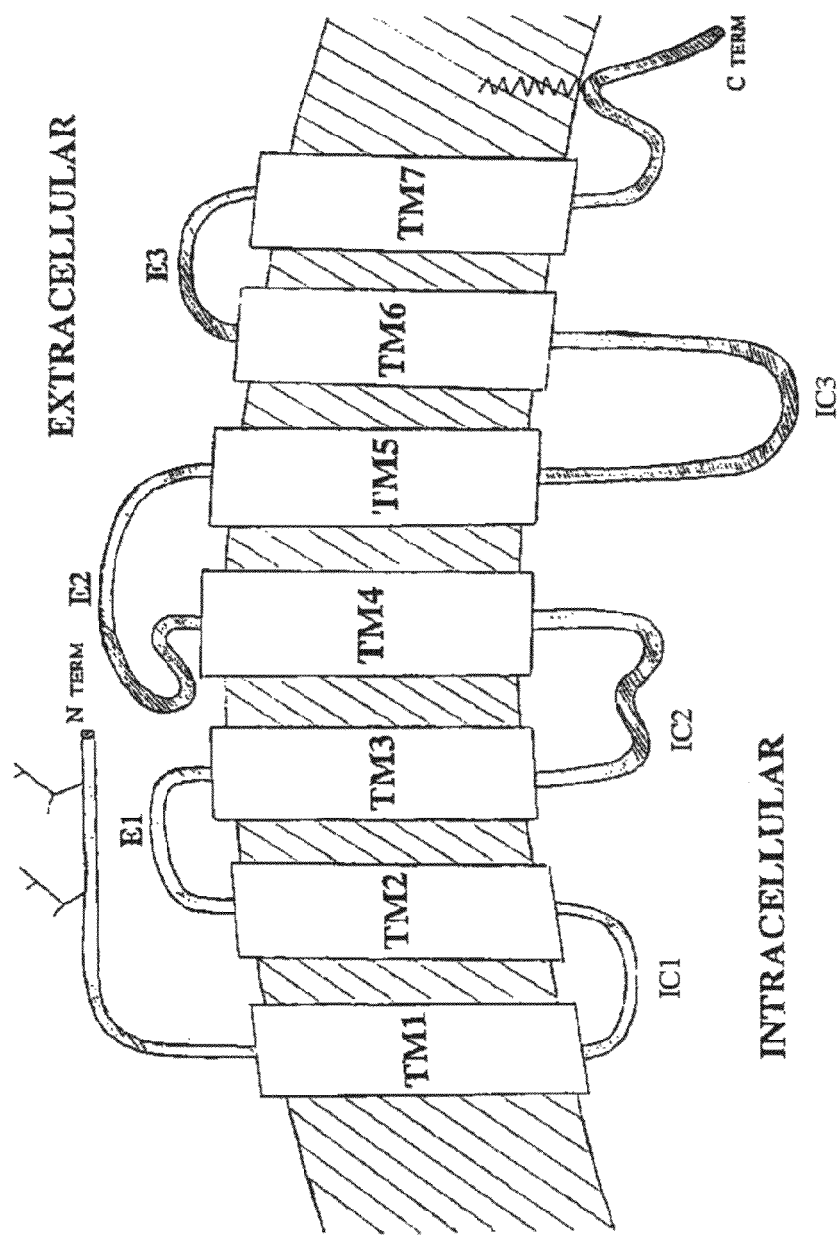
FIG. 1 is a schematic illustration of a GPCR, showing the canonical transmembrane regions (TM1, TM2, TM3, TM4, TM5, TM6, and TM7), intracellular regions (IC1, IC2, and IC3), and extracellular regions (EC1, EC2, and EC3).

"G-protein coupled receptors", or "GPCRs" are polypeptides that share a common structural motif, having seven regions of between 22 to 24 hydrophobic amino acids that form seven alpha helices, each of which spans a membrane. As illustrated in FIG. 1, each span is identified by number, i.e., transmembrane-1 (TM1), transmembrane-2 (TM2), etc. The transmembrane helices are joined by regions of amino acids between transmembrane-2 and transmembrane-3, transmembrane-4 and transmembrane-5, and transmembrane-6 and transmembrane-7 on the exterior, or "extracellular" side, of the cell membrane, referred to as "extracellular" regions 1, 2 and 3 (EC1, EC2 and EC3), respectively. The transmembrane helices are also joined by regions of amino acids between transmembrane-1 and transmembrane-2, transmembrane-3 and transmembrane-4, and transmembrane-5 and transmembrane-6 on the interior, or "intracellular" side, of the cell membrane, referred to as "intracellular" regions 1, 2 and 3 (IC1, IC2 and IC3), respectively. The "carboxy" ("C") terminus of the receptor lies in the intracellular space within the cell, and the "amino" ("N") terminus of the receptor lies in the extracellular space outside of the cell. GPCR structure and classification is generally well known in the art, and further discussion of GPCRs may be found in Probst, DNA Cell Biol. 1992 11:1-20; Marchese et al Genomics 23: 609-618, 1994; and the following books: Jürgen Wess (Ed) Structure-Function Analysis of G Protein-Coupled Receptors published by Wiley-Liss (1st edition; Oct. 15, 1999); Kevin R. Lynch (Ed) Identification and Expression of G Protein-Coupled Receptors published by John Wiley & Sons (March 1998) and Tatsuya Haga (Ed), G Protein-Coupled Receptors, published by CRC Press (Sep. 24, 1999); and Steve Watson (Ed) G-Protein Linked Receptor Factsbook, published by Academic Press (1st edition; 1994). A schematic representation of a typical GPCR is shown in FIG. 1.

The term "naturally-occurring" in reference to a GPCR means a GPCR that is naturally produced (for example and not limitation, by a mammal or by a human). Such GPCRs are found in nature. The term "non-naturally occurring" in reference to a GPCR means a GPCR that is not naturally-occurring. Wild-type GPCRs that have been made constitutively active through mutation, and variants of naturally-occurring GPCRs, e.g., epitope-tagged GPCR and GPCRs lacking their native N-terminus are examples of non-naturally occurring GPCRs.

The term "ligand" means a molecule that specifically binds to a GPCR. A ligand may be, for example a polypeptide, a lipid, a small molecule, an antibody. A "native ligand" is a ligand that is an endogenous, natural ligand for a native GPCR. A ligand may be a GPCR "antagonist", "agonist", "partial agonist" or "inverse agonist", or the like.

A "modulator" is a ligand that increases or decreases a GPCR intracellular response when it is in contact with, e.g., binds, to a GPCR that is expressed in a cell. This term includes agonists, including partial agonists and inverse agonists, and antagonists.

A "deletion" is defined as a change in either amino acid or nucleotide sequence in which one or more amino acid or nucleotide residues, respectively, are absent as compared to an amino acid sequence or nucleotide sequence of a parental GPCR polypeptide or nucleic acid. In the context of a GPCR or a fragment thereof, a deletion can involve deletion of about 2, about 5, about 10, up to about 20, up to about 30 or up to about 50 or more amino acids. A GPCR or a fragment thereof may contain more than one deletion.

An "insertion" or "addition" is that change in an amino acid or nucleotide sequence which has resulted in the addition of one or more amino acid or nucleotide residues, respectively, as compared to an amino acid sequence or nucleotide sequence of a parental GPCR. "Insertion" generally refers to addition to one or more amino acid residues within an amino acid sequence of a polypeptide, while "addition" can be an insertion or refer to amino acid, residues added at an N- or C-terminus, or both termini. In the context of a GPCR or fragment thereof, an insertion or addition is usually of about 1, about 3, about 5, about 10, up to about 20, up to about 30 or up to about 50 or more amino acids. A GPCR or fragment thereof may contain more than one insertion. Reference to particular GPCR or group of GPCRs by name, e.g., reference to the serotonin or histamine receptor, is intended to refer to the wild type receptor as well as active variants of that receptor that can bind to the same ligand as the wild type receptor and/or transduce a signal in the same way as the wild type receptor.

A "substitution" results from the replacement of one or more amino acids or nucleotides by different amino acids or nucleotides, respectively as compared to an amino acid sequence or nucleotide sequence of a parental GPCR or a fragment thereof. It is understood that a GPCR or a fragment thereof may have conservative amino acid substitutions which have substantially no effect on GPCR activity. By conservative substitutions is intended combinations such as gly, ala; val, ile, leu; asp, glu; asn, gln; ser, thr; lys, arg; and phe, tyr.

The term "biologically active", with respect to a GPCR, refers to a GPCR having a biochemical function (e.g., a binding function, a signal transduction function, or an ability to change conformation as a result of ligand binding) of a naturally occurring GPCR.

As used herein, the terms "determining," "measuring," "assessing," and "assaying" are used interchangeably and include both quantitative and qualitative determinations. Reference to an "amount" of a GPCR in these contexts is not intended to require quantitative assessment, and may be either qualitative or quantitative, unless specifically indicated otherwise.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones.

The term "fusion protein" or grammatical equivalents thereof is meant a protein composed of a plurality of polypeptide components, that while typically unjoined in their native state, are joined by their respective amino and carboxyl termini through a peptide linkage to form a single continuous polypeptide. Fusion proteins may be a combination of two, three or even four or more different proteins. The term polypeptide includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

As used herein the term "isolated," when used in the context of an isolated compound, refers to a compound of interest that is in an environment different from that in which the compound naturally occurs. "Isolated" is meant to include compounds that are within samples that are substantially enriched for the compound of interest and/or in which the compound of interest is partially or substantially purified. As used herein, the term "substantially pure" refers to a compound that is removed from its natural environment and is at least 60% free, at least 75% free, or at least 90% free from other components with which it is naturally associated.

A "coding sequence" or a sequence that "encodes" a selected polypeptide, is a nucleic acid molecule which can be transcribed (in the case of DNA) and translated (in the case of mRNA) into a polypeptide, for example, in a host cell when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence.

"Operably linked" refers to an arrangement of elements wherein the components so described are configured so as to perform their usual function. In the case of a promoter, a promoter that is operably linked to a coding sequence will effect the expression of a coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

By "nucleic acid construct" it is meant a nucleic acid sequence that has been constructed to comprise one or more functional units not found together in nature. Examples include circular, linear, double-stranded, extrachromosomal DNA molecules (plasmids), cosmids (plasmids containing COS sequences from lambda phage), viral genomes comprising non-native nucleic acid sequences, and the like.

A "vector" is capable of transferring gene sequences to a host cell. Typically, "vector construct," "expression vector," and "gene transfer vector," mean any nucleic acid construct capable of directing the expression of a gene of interest and which can transfer gene sequences to host cells, which can be accomplished by genomic integration of all or a portion of the vector, or transient or inheritable maintenance of the vector as an extrachromosomal element. Thus, the term includes cloning, and expression vehicles, as well as integrating vectors.

An "expression cassette" comprises any nucleic acid construct capable of directing the expression of a gene/coding sequence of interest, which is operably linked to a promoter of the expression cassette. Such cassettes can be constructed into a "vector," "vector construct," "expression vector," or "gene transfer vector," in order to transfer the expression cassette into a host cell. Thus, the term includes cloning and expression vehicles, as well as viral vectors.

A first polynucleotide is "derived from" or "corresponds to" a second polynucleotide if it has the same or substantially the same nucleotide sequence as a region of the second polynucleotide, its cDNA, complements thereof, or if it displays sequence identity as described above.

A first polypeptide is "derived from" or "corresponds to" a second polypeptide if it is (i) encoded by a first polynucleotide derived from a second polynucleotide, or (ii) displays sequence identity to the second polypeptides as described above.

The term "stable, folded protein insertion" refers to a folded region of polypeptide that is inserted between two neighboring domains (e.g., the TM5 and TM6 domains of a GPCR), such that the domains are spaced relative to each other at a distance that allows them to interact as in the wild-type protein. The term "stable, folded protein insertion" excludes an amino acid sequence of a fluoresecent protein (e.g., GFP, CFP or YFP), and excludes amino acid sequences that are at least 90% identical to the entire IC3 loop of a GPCR. In general, the IC3 loops of wild type GPCRs do not contain stable, folded protein domains.

The term "active form" or "native state" of a protein is a protein that is folded in a way so as to be active. A GPCR is in its active form if it can bind ligand, alter conformation in response to ligand binding, and/or transduce a signal which may or may not be induced by ligand binding. An active or native protein is not denatured.

The term "stable domain" is a polypeptide domain that, when folded in its active form, is stable, i.e., does not readily become inactive or denatured.

The term "folds autonomously" indicates a protein that folds into its active form in a cell, without biochemical denaturation and renaturation of the protein, and without chaperones.

The term "naturally-occurring" refers to an object that is found in nature. The term "non-naturally-occurring" refers to an object that is not found in nature.

DETAILED DESCRIPTION OF EXEMPLARY EMBODIMENTS

As noted above, a fusion protein is provided. In certain embodiments, the fusion protein comprises: a) a first portion of a G-protein coupled receptor (GPCR), where the first portion comprises the TM1, TM2, TM3, TM4 and TM5 regions of the GPCR; b) a stable, folded protein insertion c) a second portion of the GPCR, where the second portion comprises the TM6 and TM7 regions of the GPCR. In particular embodiments, the stable, folded protein insertion spaces the ends of the TM5 region and the TM6 region of the GPCR at a distance in the range of 7 Å to 15 Å. The stable, folded protein insertion may also provide polar surface area for crystal lattice contacts.

In the following description, the fusion protein is described first, followed by a discussion of the crystallization method in which the fusion protein may be employed.

Fusion Proteins

As noted above, a subject fusion proteins comprises: a) a first portion of a G-protein coupled receptor (GPCR), where the first portion comprises the TM1, TM2, TM3, TM4 and TM5 regions of the GPCR; b) a stable, folded protein insertion c) a second portion of the GPCR, where the second portion comprises the TM6 and TM7 regions of the GPCR. In particular embodiments, the stable, folded protein insertion spaces the ends of the TM5 region and the TM6 region of the GPCR at a distance in the range of 7 Å to 15 Å. The stable, folded protein insertion may also provide polar surface for crystal lattice contacts.

In very general terms, such a protein may be made by substituting the IC3 region of the GPCR with a stable, folded protein that holds the two remaining portions of the GPCR (i.e. the portion that lies N-terminal to the IC3 region and the portion that lies C-terminal to the IC3 region) together at a distance that is compatible with a functional GPCR in terms of pharmacologic and dynamic properties.

GPCRs

Any known GPCR is suitable for use in the subject methods, as long as it has TM5 and TM6 regions that are identifiable in the sequence of the GPCR. A disclosure of the sequences and phylogenetic relationships between 277 GPCRs is provided in Joost et al. (Genome Biol. 2002 3:RESEARCH0063, the entire contents of which is incorporated by reference) and, as such, at least 277 GPCRs are suitable for the subject methods. A more recent disclosure of the sequences and phylogenetic relationships between 367 human and 392 mouse GPCRs is provided in Vassilatis et al. (Proc Natl Acad Sci 2003 100:4903-8 which is hereby incorporated by reference in its entirely) and, as such, at least 367 human and at least 392 mouse GPCRs are suitable for the subject methods. GPCR families are also described in Fredriksson et al (Mol. Pharmacol. 2003 63, 1256-72).

The methods may be used, by way of exemplification, for purinergic receptors, vitamin receptors, lipid receptors, peptide hormone receptors, non-hormone peptide receptors, nonpeptide hormone receptors, polypeptide receptors, protease receptors, receptors for sensory signal mediator, and biogenic amine receptors not including (β2-adrenergic receptor. In certain embodiments, said biogenic amine receptor does not include an adrenoreceptor. α-type adrenoreceptors (e.g. $\alpha_{1A}$, $\alpha_{1B}$ or $\alpha_{1c}$ adrenoreceptors), and β-type adrenoreceptors (e.g. $\beta_1$, $\beta_2$, or $\beta_3$ adrenoreceptors) are discussed in Singh et al., J. Cell Phys. 189:257-265, 2001.

It is recognized that both native (naturally occurring) and altered native (non-naturally occurring) GPCRs may be used in the subject methods. In certain embodiments, therefore, an altered native GPCR (e.g. a native GPCR that is altered by an amino acid substitution, deletion and/or insertion) such that it binds the same ligand as a corresponding native GPCR, and/ or couples to a G-protein as a result of the binding. In certain cases, a GPCR employed herein may be at least 80% identical to, e.g., at least 90% identical, at least 85% identical, at least 90% identical, at least 95% identical, or at least 98% identical, to a naturally occurring GPCR.

As such, the following GPCRs (native or altered) find particular use as parental GPCRs in the subject methods: cholinergic receptor, muscarinic 3; melanin-concentrating hormone receptor 2; cholinergic receptor, muscarinic 4; niacin receptor; histamine 4 receptor; ghrelin receptor; CXCR3 chemokine receptor; motilin receptor; 5-s hydroxytryptamine (serotonin) receptor 2A; 5-hydroxytryptamine (serotonin) receptor 2B; 5-hydroxytryptamine (serotonin) receptor 2C; dopamine receptor D3; dopamine receptor D4; dopamine receptor D1; histamine receptor H2; histamine receptor H3; galanin receptor 1; neuropeptide Y receptor Y1; angiotensin II receptor 1; neurotensin receptor 1; melanocortin 4 receptor; glucagon-like peptide 1 receptor; adenosine A1 receptor; cannabinoid receptor 1; and melanin-concentrating hormone receptor 1.

In particular embodiments, the GPCR may belong to one of the following GPCR families: amine, peptide, glycoprotein hormone, opsin, olfactory, prostanoid, nucleotide-like, cannabinoid, platelet activating factor, gonadotropin-releasing hormone, thyrotropin-releasing hormone or melatonin families, as defined by Lapinsh et al (Classification of G-protein coupled receptors by alignment-independent extraction of principle chemical properties of primary amino acid sequences. Prot. Sci. 2002 11:795-805) or family B (which includes the PTH and glucagon receptors) or family C (which includes the GABA and glutamate receptors).

Figure 2:
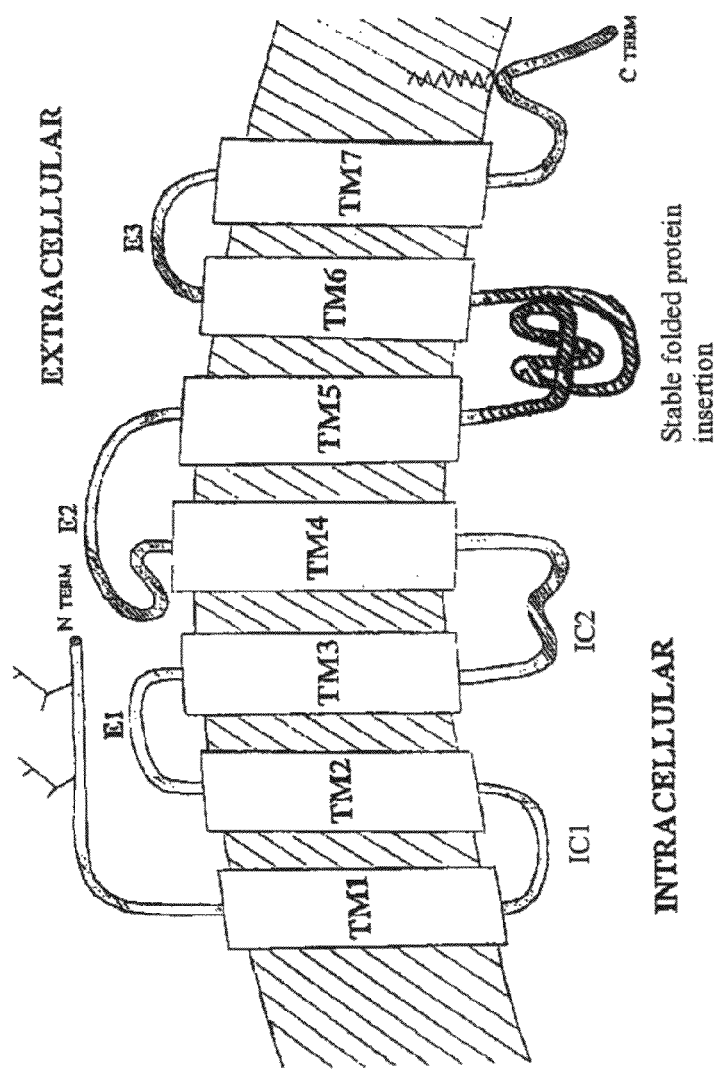
FIG. 2 is a schematic illustration of a subject fusion protein, showing a stable, folded protein insertion between the TM5 and TM6 regions of a GPCR.

In the subject methods, the region between the TM5 and TM6 regions of a GPCR (i.e., the IC3 region) is usually identified, and replaced with a stable, folded protein insertion to form a fusion protein. The stable, folded protein insertion spaces the TM5 and TM6 regions relative to one another. A schematic representation of the prototypical structure of a GPCR is provided in FIG. 1, where these regions, in the context of the entire structure of a GPCR, may be seen. A schematic representation of a subject fusion protein is shown in FIG. 2. In one embodiment, the IC3 loop of the GPCR is replaced with a stable, folded protein insertion.

The IC3 region of a GPCR lies in between transmembrane regions TM5 and TM6 and, may be about 12 amino acids (CXCR3 and GPR40) to about 235 amino acids (cholinergic receptor, muscarinic 3) in length, for example. The TM5, IC3, and TM6 regions are readily discernable by one of skill in the art using, for example, a program for identifying transmembrane regions; once transmembrane regions TM5 and TM6 regions are identified, the IC3 region will be apparent. The TM5, IC3, and TM6 regions may also be identified using such methods as pairwise or multiple sequence alignment (e.g. using the GAP or BESTFIT of the University of Wisconsin's GCG program, or CLUSTAL alignment programs, Higgins et al., Gene. 1988 73:237-44), using a target GPCR and, for example, GPCRs of known structure.

Suitable programs for identifying transmembrane regions include those described by Moller et al., (Bioinformatics, 17:646-653, 2001). A particularly suitable program is called "TMHMM" Krogh et al., (Journal of Molecular Biology, 305:567-580, 2001). To use these programs via a user interface, a sequence corresponding to a GPCR or a fragment thereof is entered into the user interface and the program run. Such programs are currently available over the world wide web, for example at the website of the Center for Biological Sequence Analysis. The output of these programs may be variable in terms its format, however they usually indicate transmembrane regions of a GPCR using amino acid coordinates of a GPCR.

When TM regions of a GPCR polypeptide are determined using TMHMM, the prototypical GPCR profile is usually obtained: an N-terminus that is extracellular, followed by a segment comprising seven TM regions, and further followed by a C-terminus that is intracellular. TM numbering for this prototypical GPCR profile begins with the most N-terminally disposed TM region (TM1) and concludes with the most C-terminally disposed TM region (TM7).

Accordingly, in certain embodiments, the amino acid coordinates of the TM5, IC-3, and TM6 regions of a GPCR are identified by a suitable method such as TMHMM.

In certain cases, once the TM5-IC3-TM6 segment is identified for a GPCR, a suitable region of amino acids is chosen for substitution with the amino acid sequence of the a stable, folded protein insertion. In certain embodiments, the substituted region may be identified using conserved or semi-conserved amino acids in the TM5 and TM6 transmembrane regions. In certain embodiments, the N-terminus of the a stable, folded protein insertion is linked to the amino acid that is 15 to 25 (e.g., 15, 16, 17, 18, 19, 20, 21, 22, 23, 24 or 25; e.g., 18-20) residues C-terminal to a conserved proline in the TM5 of the GPCR, although linkages outside of this region are envisioned. In certain embodiments, the C-terminus of the stable, folded protein insertion may be linked to the amino acid that is 20-30 (e.g., 20, 21, 22, 23, 24, 25, 26, 27, 28, 29 or 30; e.g., 23-27) residues N-terminal a conserved proline in the TM6 region of the GPCR, although linkages outside of this region are envisioned.

For GPCRs that contain no conserved proline residues in TM5 and TM6, positions for inserting an a stable, folded protein insertion can be determined based on two considerations: a) alignment of the sequence of the GPCR with receptor members of the same subfamily (which contained conserved proline residues in TM5 or TM6; b) by identifying the juxtaposition to the TM5/TM6 regions by hydrophobicity analysis.

In addition to substituting IC3 region of a GPCR with a stable, folded protein insertion, as described above, in certain cases, the C-terminal region of the GPCR (which is C-terminal to the cysteine palmitoylation site that is approximately 10 to 25 amino acid residues downstream of a conserved NPXXY motif), may be deleted. In certain cases, the 20-30 amino acids immediately C-terminal to the cysteine palmitoylation site are not deleted.

Stable, Folded Protein Insertions

In certain embodiments, a stable, folded protein insertion of a subject fusion protein may be a soluble, stable protein (e.g., a protein displaying resistance to thermal and chemical denaturation) that folds autonomously of the GPCR portion of the fusion protein, in a cell. In certain cases, the stable, folded protein insertion may have no cysteine residues (or may be engineered to have no cysteine residues) in order to avoid potential disulphide bonds between the stable, folded protein insertion and a GPCR portion of the fusion protein, or internal disulphide bonds. Stable, folded protein insertions are conformationally restrained, and are resistant to protease cleavage.

In certain cases, stable, folded protein insertions may contain most or all of the amino acid sequence of a polypeptide that is readily crystallized. Such proteins may be characterized by a large number of deposits in the protein data bank (www.rcsb.org) in a variety of space groups and crystal packing arrangements. While examples that employ lysozyme as stable, folded protein insertion are discussed below, the general principles may be used to employ any of a number of polypeptides that have the characteristics discussed above. Suitable stable, folded protein insertion candidates include those containing the amino acid sequence of proteins that are readily crystallized including, but not limited to: lysozyme, glucose isomerase, xylanase, trypsin inhibitor, crambin, ribonuclease. Other suitable polypeptides may be found at the BMCD database (Gilliland et al 1994. The Biological Macromolecule Crystallization Database, Version 3.0: New Features, Data, and the NASA Archive for Protein Crystal Growth Data. Acta Crystallogr. D50 408-413), as published to the world wide web.

In certain embodiments, the stable, folded protein insertion used may be at least 80% identical (e.g., at least 85% identical, at least 90% identical, at least 95% identical or at least 98% identical to a wild type protein. Many suitable wild type proteins, including non-naturally occurring variants thereof, are readily crystallizable.

As noted above, one such stable, folded protein insertion that may be employed in a subject fusion protein is lysozyme. Lysozyme is a highly crystallizable protein (see, e.g., Strynadka et al Lysozyme: a model enzyme in protein crystallography EXS 1996 75: 185-222) and at present over 200 atomic coordinates for various lysozymes, including many wild-type lysozymes and variants thereof, including lysozymes from phage T4, human, swan, rainbow trout, guinea fowl, soft-shelled turtle, tapes japonica, nurse shark, mouse sperm, dog and phage P1, as well as man-made variants thereof, have been deposited in NCBI's structure database. A subject fusion protein may contain any of a wide variety of lysozyme sequences.

The length of the stable, folded protein insertion may be between 80-500 amino acids, e.g., 100-200 amino acids in length, although stable, folded protein insertions having lengths outside of this range are also envisioned.

As noted above, the stable, folded protein insertion is not fluorescent or light-emitting. As such, the stable, folded protein insertion is not CFP, GFP, YFP, luciferase, or other light emitting, fluorescent variants thereof. In certain cases, a stable, folded protein insertion region does not contain a flexible polyglycine linker or other such conformationally unrestrained regions. In certain cases, the stable, folded protein insertion contains a sequence of amino acids from a protein that has a crystal structure that has been solved. In certain cases, the stable, folded protein insertion should not have highly flexible loop region characterized by high crystallographic temperature factors (i.e., high B-factors).

In general terms, once a suitable polypeptide is identified, a stable, folded protein insertion may be designed by deleting amino acid residues from the N-terminus, the C-terminus or both termini of the polypeptide such that the closest alpha carbon atoms in the backbone at the termini of the polypeptide are spaced by a distance of in the range of 6 Å to 16 Å, e.g., 7 Å to 15 Å, 7 Å to 10 Å, 12 Å to 15 Å, 10 Å to 13 Å, or about 11 Å (i.e. 10 Å to 12 Å). The stable, folded protein insertion, disposed between the TM5 and TM6 regions of a GPCR, spaces those regions by that distance. The distance may be modified by adding or removing amino acids to or from the stable, folded protein insertion.

Amino acid sequence for exemplary lysozyme fusion proteins are set forth in FIG. 9, and the amino acid sequences of exemplary alternative insertions (which may be substituted into any of the sequences of FIG. 9 in place of the lysozyme sequence) are shown in FIG. 16. These sequences include the sequences of trypsin inhibitor, calbindin, barnase, xylanase and glucokinase although other sequences can be readily used.

Nucleic Acids

A nucleic acid comprising a nucleotide sequence encoding a subject fusion protein is also provided. A subject nucleic acid may be produced by any method. Since the genetic code and recombinant techniques for manipulating nucleic acid are known, the design and production of nucleic acids encoding a subject fusion protein is well within the skill of an artisan. In certain embodiments, standard recombinant DNA technology (Ausubel, et al, Short Protocols in Molecular Biology, 3rd ed., Wiley & Sons, 1995; Sambrook, et al., Molecular Cloning: A Laboratory Manual, Second Edition, (1989) Cold Spring Harbor, N.Y.) methods are used.

For example, site directed mutagenesis and subcloning may be used to introduce/delete/substitute nucleic acid residues in a polynucleotide encoding GPCR. In other embodiments, PCR may be used. Nucleic acids encoding a polypeptide of interest may also be made by chemical synthesis entirely from oligonucleotides (e.g., Cello et al., Science (2002) 297:1016-8).

In certain embodiments, the codons of the nucleic acids encoding polypeptides of interest are optimized for expression in cells of a particular species, particularly a mammalian, e.g., human, species. Vectors comprising a subject nucleic acid are also provided. A vector may contain a subject nucleic acid, operably linked to a promoter.

A host cell (e.g., a host bacterial, mammalian, insect, plant or yeast cell) comprising a subject nucleic acid is also provided as well a culture of subject cells. The culture of cells may contain growth medium, as well as a population of the cells. The cells may be employed to make the subject fusion protein in a method that includes culturing the cells to provide for production of the fusion protein. In many embodiments, the fusion protein is directed to the plasma membrane of the cell, and is folded into its active form by the cell.

The native form of a subject fusion protein may be isolated from a subject cell by conventional technology, e.g., by precipitation, centrifugation, affinity, filtration or any other method known in the art. For example, affinity chromatography (Tilbeurgh et al., (1984)

FEBS Lett. 16:215); ion-exchange chromatographic methods (Goyal et al., (1991) Biores. Technol. 36:37; Fliess et al., (1983) Eur. J. Appl. Microbiol. Biotechnol. 17:314; Bhikhabhai et al., (1984) J. Appl. Biochem. 6:336; and Ellouz et al., (1987) Chromatography 396:307), including ion-exchange using materials with high resolution power (Medve et al., (1998) J. Chromatography A 808:153; hydrophobic interaction chromatography (Tomaz and Queiroz, (1999) J. Chromatography A 865:123; two-phase partitioning (Brumbauer, et al., (1999) Bioseparation 7:287); ethanol precipitation; reverse phase HPLC; chromatography on silica or on a cation-exchange resin such as DEAE; chromatofocusing; SDS-PAGE; ammonium sulfate precipitation; or size exclusion chromatography using, e.g., Sephadex G-75, may be employed.

In particular embodiments, the GPCR, e.g., the N- or C-terminus of the GPCR or an external loop of the GPCR, may be tagged with an affinity moiety, e.g., a his tag, GST, MBP, flag tag, or other antibody binding site, in order to facilitate purification of the GPCR fusion protein by affinity methods.

Before crystallization, a subject fusion protein may be assayed to determine if the fusion protein is active, e.g., can bind ligand and change in conformation upon ligand binding, and if the fusion protein is resistant to protease cleavage. Such assays are well known in the art.

In certain cases the subject fusion protein may be combined with a ligand for the GPCR of the fusion protein prior to crystallization.

Crystallization Methods

A subject fusion protein may be crystallized using any of a variety of crystallization methods, many of which are reviewed in Caffrey *Membrane protein crystallization*. J. Struct. Biol. 2003 142:108-32. In general terms, the methods are lipid-based methods that include adding lipid to the fusion protein prior to crystallization. Such methods have previously been used to crystallize other membrane proteins. Many of these methods, including the lipidic cubic phase crystallization method and the bicelle crystallization method, exploit the spontaneous self-assembling properties of lipids and detergent as vesicles (vesicle-fusion method), discoidal micelles (bicelle method), and liquid crystals or mesophases (in meso or cubic-phase method). Lipidic cubic phases crystallization methods are described in, for example: Landau et al, *Lipidic cubic phases: a novel concept for the crystallization of membrane proteins*. Proc. Natl. Acad. Sci. 1996 93:14532-5; Gouaux, It's not just a phase: crystallization and X-ray structure determination of bacteriorhodopsin in lipidic cubic phases. Structure. 1998 6:5-10; Rummel et al, *Lipidic Cubic Phases: New Matrices for the Three-Dimensional Crystallization of Membrane Proteins*. J. Struct. Biol. 1998 121:82-91; and Nollert et al *Lipidic cubic phases as matrices for membrane protein crystallization* Methods. 2004 34:348-53, which publications are incorporated by reference for disclosure of those methods. Bicelle crystallization methods are described in, for example: Faham et al *Crystallization of bacteriorhodopsin from bicelle formulations at room temperature*. Protein Sci. 2005 14:836-40. 2005 and Faham et al, *Bicelle crystallization: a new method for crystallizing membrane proteins yields a monomeric bacteriorhodopsin structure*. J Mol Biol. 2002 Feb. 8; 316(1):1-6, which publications are incorporated by reference for disclosure of those methods.

Also provided is a method of determining a crystal structure. This method may comprise receiving an above described fusion protein, crystallizing the fusion protein to produce a crystal; and obtaining atomic coordinates of the fusion protein from the crystal. The fusion protein may be received from a remote location (e.g., a different laboratory in the same building or campus, or from a different campus or city), and, in certain embodiments, the method may also comprise transmitting the atomic coordinates, e.g., by mail, e-mail or using the internet, to the remote location or to a third party.

In other embodiments, the method may comprise forwarding a fusion protein to a remote location where the protein may be crystallized and analyzed, and receiving the atomic coordinates of the fusion protein.

In order to further illustrate the present invention, the following specific examples are given with the understanding that they are being offered to illustrate the present invention and should not be construed in any way as limiting its scope.

Methods

Molecular Biology for Generation of Mammalian and Sf9 Expression Constructs.

The insect cell expression plasmid that was used as a template for modification of the human $\beta_2AR$ gene has been described previously (X. Yao et al., Nat Chem Biol 2, 417 (2006)): the wild-type coding sequence of the human $\beta_2AR$ (starting at Gly2) was cloned into the pFastbac 1 Sf-9 expression vector (Invitrogen) with the HA signal sequence followed by the Flag epitope tag at the amino terminus and the third glycosylation site mutated as N187E. Using this template, a TAA stop codon was placed between Gly365 and Tyr366, terminating translation without the 48 C-terminal residues of the wild-type $\beta_2AR$ ("$\beta_2AR365$"). A synthetic DNA cassette encoding the T4 Lysozyme (WT*-C54T, C97A) protein was made by overlapping extension PCR of 50-base oligonucleotides. This cassette was amplified and inserted into the $\beta_2AR365$ construct between Ile$233^{5.72}$ and Arg$260^{6.22}$ ("E1" in FIG. 3A), using the Quickchange Multi protocol (Stratagene). The corresponding mammalian cell expression plasmid was made by amplifying the entire fusion gene and cloning it into pCDNA3 (Invitrogen). Further deletions in the Sf9 and mammalian cell constructs were made using appropriate synthetic oligonucleotides in the Quickchange Multi protocol (Stratagene). All constructs were confirmed by sequencing.

HEK293 Cell Staining and Immunofluorescence Staining.

HEK293 cells were cultured on plastic dishes at 37° C. with 5% $CO_2$ in Dulbecco's modified Eagle's medium (Cellgro) with 5% fetal bovine serum. For an individual expression experiment, cells at confluency were split, and approximately 100,000 cells were used to seed glass cover slips in the same medium. After 2 d, cells were transfected with the addition of 1 µg of a given pcDNA3-receptor plasmid and 3 µl of Fugene 6 reagent (Roche). 48 h after transfection, cells were washed with PBS, fixed with 4% paraformaldehyde, blocked with PBS+2% goat serum, permeabilized with PBS+2% goat serum+0.5% Nonidet P-40 (Sigma), stained with Alexa488-conjugated M1 anti-FLAG antibody (for receptor) plus DAPI (nuclear) in blocking buffer, and washed with blocking buffer. Cover slips were mounted on microscope slides with Vectashield (Vector Labs) and dried overnight. Staining was visualized with an Axioplan 2 fluorescence imaging system, using a 63× objective and either green (Alexa488/FITC) or blue (DAPI/Hoechst) filter sets. A plasmid pcDNA3-$\beta_1$AR, expressing an N-terminal FLAG-tagged $\beta_1$ adrenergic receptor, was used as a positive control for cell-surface staining. Empty pcDNA3 was used as a negative control to assess background staining.

Expression and Purification of $\beta_2$AR-T4L from Baculovirus-Infected Sf9 Cells.

Recombinant baculovirus was made from pFastbac1-$\beta_2$AR-T4L using the Bac-to-Bac system (Invitrogen), as described previously (X. Yao et al., Nat Chem Biol 2, 417 (2006)). The $\beta_2$AR-T4L protein was expressed in Sf9 insect cells infected with this baculovirus, and solubilized according to previously described methods (B. K. Kobilka, Anal Biochem 231, 269 (1995)). Dodecylmaltoside-solubilized receptor with the N-terminal FLAG epitope (DYKDDDA) was purified by M1 antibody affinity chromatography (Sigma), treated with TCEP/iodoacetamide, and further purified by alprenolol-Sepharose chromatography (2) to isolate only functional GPCR. Eluted alprenolol-bound receptor was re-bound to M1 FLAG resin, and ligand exchange with 30 µM carazolol was performed on the column. $\beta_2$AR-T4L was eluted from this final column with 0.2 mg/ml FLAG peptide in HLS buffer (0.1% dodecylmaltoside, 20 mM Hepes, 100 mM NaCl, pH 7.5) plus 30 µM carazolol and 5 mM EDTA. N-linked glycolsylations were removed by treatment with PNGaseF (NEB). Protein was concentrated from ~5 mg/ml to 50 mg/ml with a 100 kDa molecular weight cut-off Vivaspin concentrator (Vivascience), and dialyzed against HLS buffer plus 10 µM carazolol.

Binding Measurements on Wild-type $\beta_2$AR and $\beta_2$Ar-T4L from Membranes.

Figure 10:
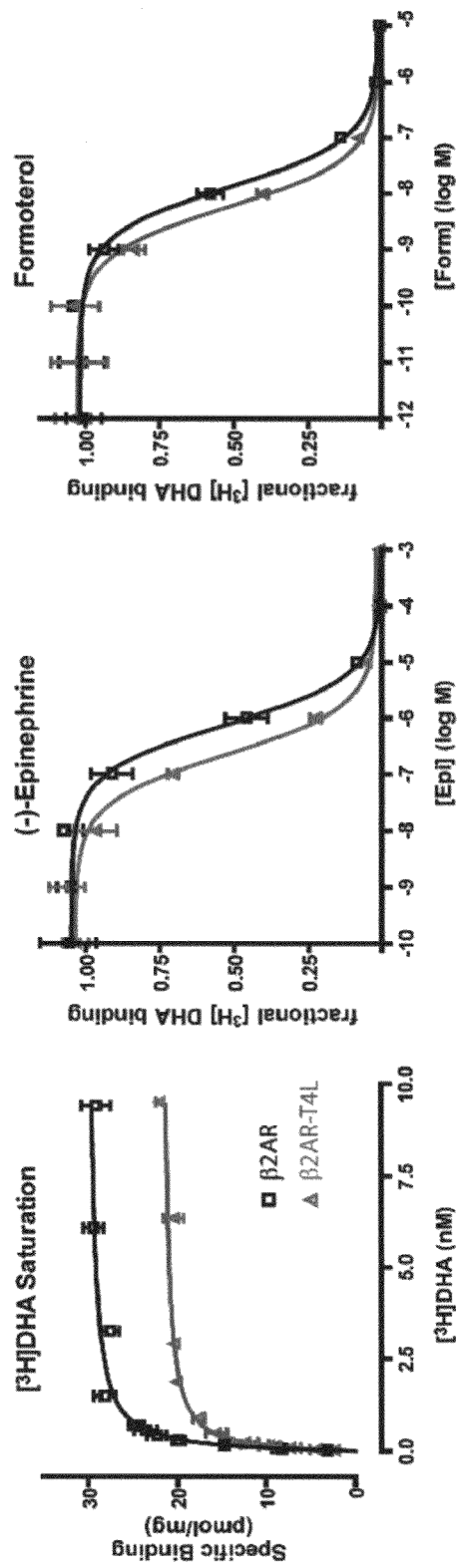
FIG. 10. Affinity curves for adrenergic ligands binding to $\beta_2$AR-T4L and wild-type $\beta_2$AR. Saturation curves for the antagonist [$^3$H]DHA is shown at left, next to competition binding curves for the natural ligand (−)-Epinephrine and the high-affinity synthetic agonist Formoterol. Binding experiments on membranes isolated from Sf9 insect cells expressing the receptors were performed as described above.

Membrane preparation from baculovirus-infected Sf9 cells was performed as described previously (G. Swaminath, J. Steenhuis, B. Kobilka, T. W. Lee, Mol Pharmacol 61, 65 (2002)). For each binding reaction, membranes containing 0.7 µg total membrane protein were used. Saturation binding of [$^3$H]-dihydroalprenolol (DHA) was measured by incubating membranes resuspended in 500 ml binding buffer (75 mM Tris, 12.5 mM MgCl$_2$, 1 mM EDTA, pH 7.4, supplemented with 0.4 mg/ml BSA) with 12 different concentrations of [$^3$H]DHA (Perkin Elmer) between 20 µM and 10 nM. After 1 h incubation with shaking at 230 rpm, membranes were filtered from the binding reactions with a Brandel harvester, washed with binding buffer, and measured for bound [$^3$H] DHA with a Beckman LS6000 scintillation counter. Non-specific binding was assessed by performing identical reactions in the presence of 1 µM alprenolol. For competition binding, membranes resuspended in 500 ml binding buffer were incubated with 0.5 nM [$^3$H]DHA plus increasing concentrations of the competing ligand (all compounds were purchased from Sigma). For (−)-isoproterenol and (−)-epinephrine, concentrations were 100 µM-1 mM, each increasing by a factor of 10. For salbutamol, concentrations were 1 nM-10 mM. For ICI-118,551 and formoterol, concentrations were 1 µM-10 µM. Non-specific binding was measured by using 1 mM unlabeled alprenolol as competing ligand. Each data point in the curves in FIGS. 4A and 10 represents the mean of three separate experiments, each done in triplicate. Binding data were analyzed by nonlinear regression analysis using Graphpad Prism. The values for K$_d$ of [$^3$H]DHA and K$_i$ of other ligands are shown in Table S1.

Bimane Fluorescence Experiments on Purified, Detergent-Solubilized Receptors $\beta_2$AR-T4L and $\beta_2$AR365 were purified as described above, with two differences. First, prior to iodoacetamide treatment, FLAG-pure receptor at 2.5 µM (measured by soluble [$^3$H]DHA binding) was incubated with 5 µM mono-bromobimane for 1 h at 4° C. Second, after binding the bimane-labeled alprenolol-Sepharose-purified receptor to M1 antibody resin, the column was washed extensively with ligand-free buffer before elution. Based on previous precedent, this protocol is expected to target primarily Cys265$^{6.27}$ for fluorophore derivitization. Fluorescence spectroscopy was performed on a Spex FluoroMax-3 spectrofluorometer (JobinYvon Inc.) with photon-counting mode, using an excitation and emission bandpass of 5 nm. All experiments were done at 25° C. For emission scans, we set excitation at 350 nm and measured emission from 417 to 530 nm with an integration time of 1.0 s nm$^{-1}$. To determine the effect of ligands, spectra were measured after 15 min incubation with different compounds (at saturating concentrations−[(−)-isoproterenol]= 100 µM, [ICI-118,551]=10 µM [salbutamol]=500 µM). Fluorescence intensity was corrected for background fluorescence from buffer and ligands in all experiments. The curves shown in FIG. 4B are each the average of triplicate experiments performed in parallel. $\lambda_{max}$ values and intensity changes for $\beta_2$AR-T4L and $\beta_2$AR365, each incubated with different ligands, are tabulated in Table S2.

Comparing the Proteolytic Stability of Unliganded $\beta_2$AR and $\beta_2$AR-T4L.

Figure 11:
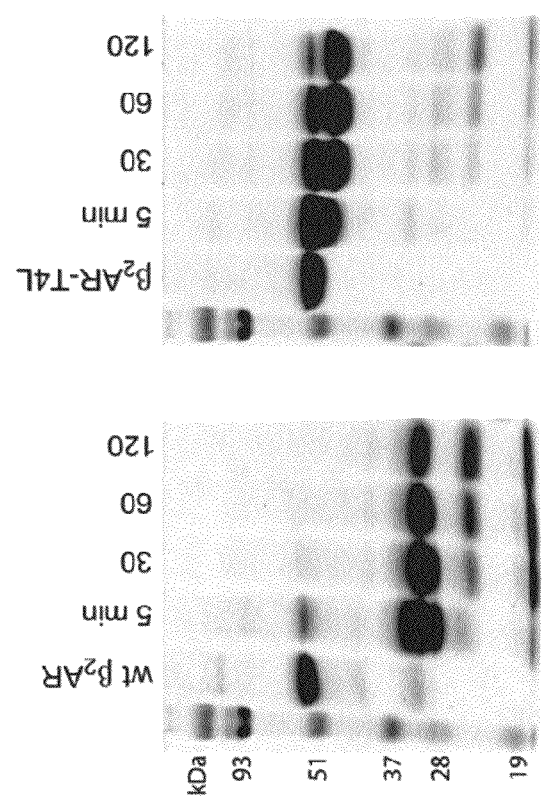
FIG. 11. Comparison of the proteolytic stability between the wild-type $\beta_2$AR and NAR-T4L in a limited trypsin proteolysis assay. TPCK-trypsin was added to carazolol-bound, purified, dodecylmaltoside-solubilized receptor at a 1:1000 ratio (wt:wt), and samples were analyzed by SDS-PAGE. Intact $\beta_2$AR-T4L (56.7 kD) and FLAG-tagged wild-type $\beta_2$AR (47.4 kD) migrate similarly as ~55 kD bands. Markers are Biorad low-range SDS-PAGE protein standards.

The limited trypsin proteolysis protocol was adapted from Jiang et al. (Z. G. Jiang, M. Carraway, C. J. McKnight, Biochemistry 44, 1163 (2005)). Carazolol-bound $\beta_2$AR-T4L or wild-type $\beta_2$AR (each at 30 mg/ml) were diluted 10-fold into HLS buffer (see above) and TPCK-trypsin was added at a 1:1000 ratio (wt:wt). The digests were incubated at room temperature. At various time points, aliquots were removed and flash frozen on dry ice/ethanol. After the last aliquot was removed, all samples were thawed, and an equal volume of 10% SDS/PAGE loading buffer was added to each. Samples were then analyzed by electrophoresis on 12% polyacrilamide gels, followed by staining with Coomassie blue. See FIG. 11.

Comparing the Stability of Unliganded $\beta_2$AR and $\beta_2$AR-T4L

Unliganded $\beta_2$AR365 and $\beta_2$AR-T4L were each purified as described above for the bimane experiments. 200 µA 0.02 mg/ml receptor in HLS buffer was incubated at 37° C. on a heating block. At the time points indicated in FIG. 12, samples were briefly spun and gently vortexed and 16.5 µl was removed and diluted 18.2-fold in HLS (300 µl total). Then 4×5 µl was removed for determination of total binding and 2×5 µl was removed for nonspecific binding. To measure soluble binding, 5 µl diluted receptor was added to 105 µl HLS (400-fold final dilution of receptor) containing 10 nM [$^3$H]DHA±10 µM cold alprenolol. Reactions were incubated 30 min at RT, then on ice until processing. 100 µl of each reaction was applied to a 1 ml G50 column to separate protein from residual unbound [$^3$H]DHA, and receptor was eluted using 1.1 ml ice-cold HLS. Bound [$^3$H]DHA was quantified on a Beckman LS6000 scintillation counter.

Carazolol Dissociation from the "Wild-type" Receptor $\beta_2$AR365

$\beta_2$AR365 was purified with carazolol bound, according to the protocol described above for $\beta_2$AR-T4L. Carazolol-bound receptor (at approximately 50 µM concentration) was dialyzed in the dark against 1 L dialysis buffer (20 mM HEPES pH7.5, 100 mM NaCl, 0.1% dodecylmaltoside, 300 micromolar alprenolol) at room temperature with stirring. At indicated time points, two samples were removed from the parafilm-sealed open-ended dialysis chamber, diluted into fresh dialysis buffer, and carazolol emission spectra were obtained on a Spex FluoroMax spectrofluorometer (using excitation at 330 nm and emission from 335 to 400 nm). As internal standards for every time point, samples were removed for determination of protein concentration using the Bio-Rad Protein DC kit. See FIG. 14.

CAM and UCM Mutants

Figure 8:
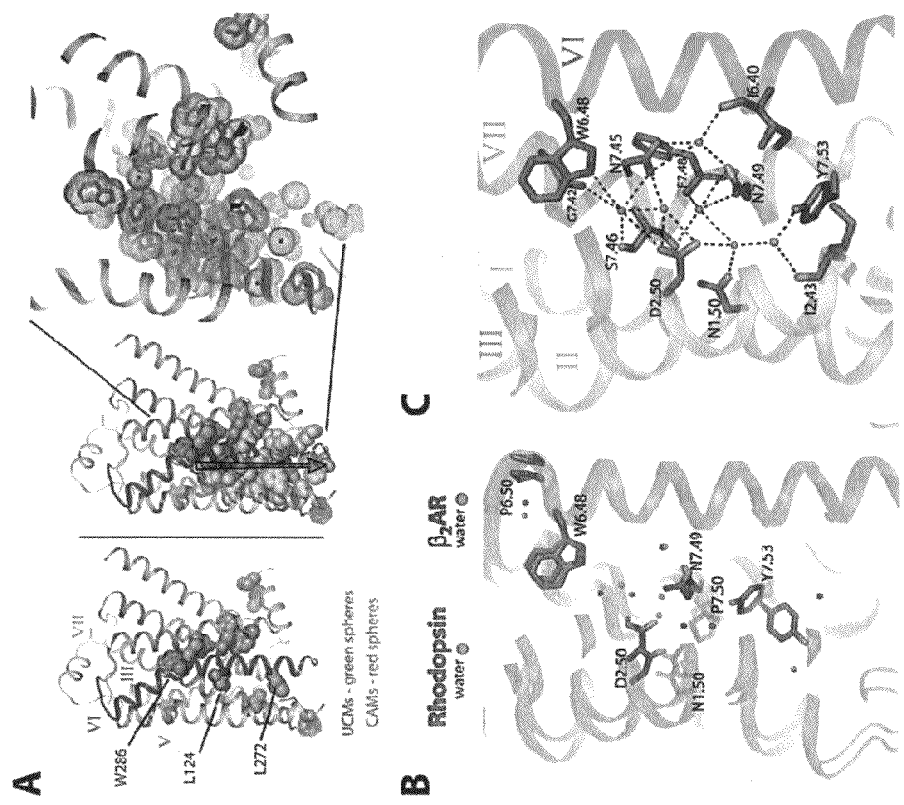
FIG. 8. Packing interactions in the NAR that are likely to be modulated during the activation process. A. On the left, residues previously demonstrated to be CAMs or UCMs are shown as van der Waals spheres mapped onto a backbone cartoon of the $\beta_2$AR-T4L structure. On the right, residues that are found within 4 Å of the CAMs Leu124$^{3.43}$ and Leu272$^{6.34}$ are shown as yellow spheres or dot surfaces. A vertical cross-section through the structure illustrates that these surrounding residues connect the CAMs on helices III and VI with the UCMs on helix VII through packing interactions. B. In both $\beta_2$AR-T4L (blue) and rhodopsin (purple), a network of ordered water molecules is found at the interface between the transmembrane helices at their cytoplasmic ends. C. Network of hydrogen bonding interactions between water molecules and $\beta_2$AR-T4L residues (sidechains as blue sticks), notably the UCMs on helix VII (orange cartoon).

The CAMs (constitutively active mutants) described in the literature that are the basis for FIG. 8A and the associated discussion are: L124A, C116F, D130A, L272C, and C285T. The UCMs (uncoupling mutations) from the literature that were used are: D79N, F139A, T1641, N318K, N322A, P323A, Y326A, L339A, and L340A.

TABLE S1

Binding affinities of different ligands for the wild-type $\beta_2$AR and the fusion protein $\beta_2$AR-T4L.

Saturation Binding

| [$^3$H]DHA | $K_d$ ± SE (nM) | Bmax (pmol/mg) |
| --- | --- | --- |
| $\beta_2$AR | 0.161 ± 0.012 | 30.0 ± 0.5 |
| $\beta_2$AR-T4L | 0.180 ± 0.016 | 21.6 ± 0.5 |

Competition Binding

| Ligand | $K_i$ [S.E. interval] for $\beta_2$AR (nM) | $K_i$ [S.E. interval] for $\beta_2$AR-T4L (nM) |
| --- | --- | --- |
| (−)-isoproteronol | 50.6 [48.9-52.3] | 15.7 [15.2-16.2] |
| (−)-epinephrine | 175 [163-188] | 56.0 [52.8-59.4] |
| salbutamol | 728 [708-750] | 307 [291-323] |
| ICI-118,551 | 0.617 [0.570-0.668] | 0.626 [0.591-0.662] |
| formoterol | 3.60 [3.39-3.83] | 1.68 [1.55-1.81] |

Figure 4:
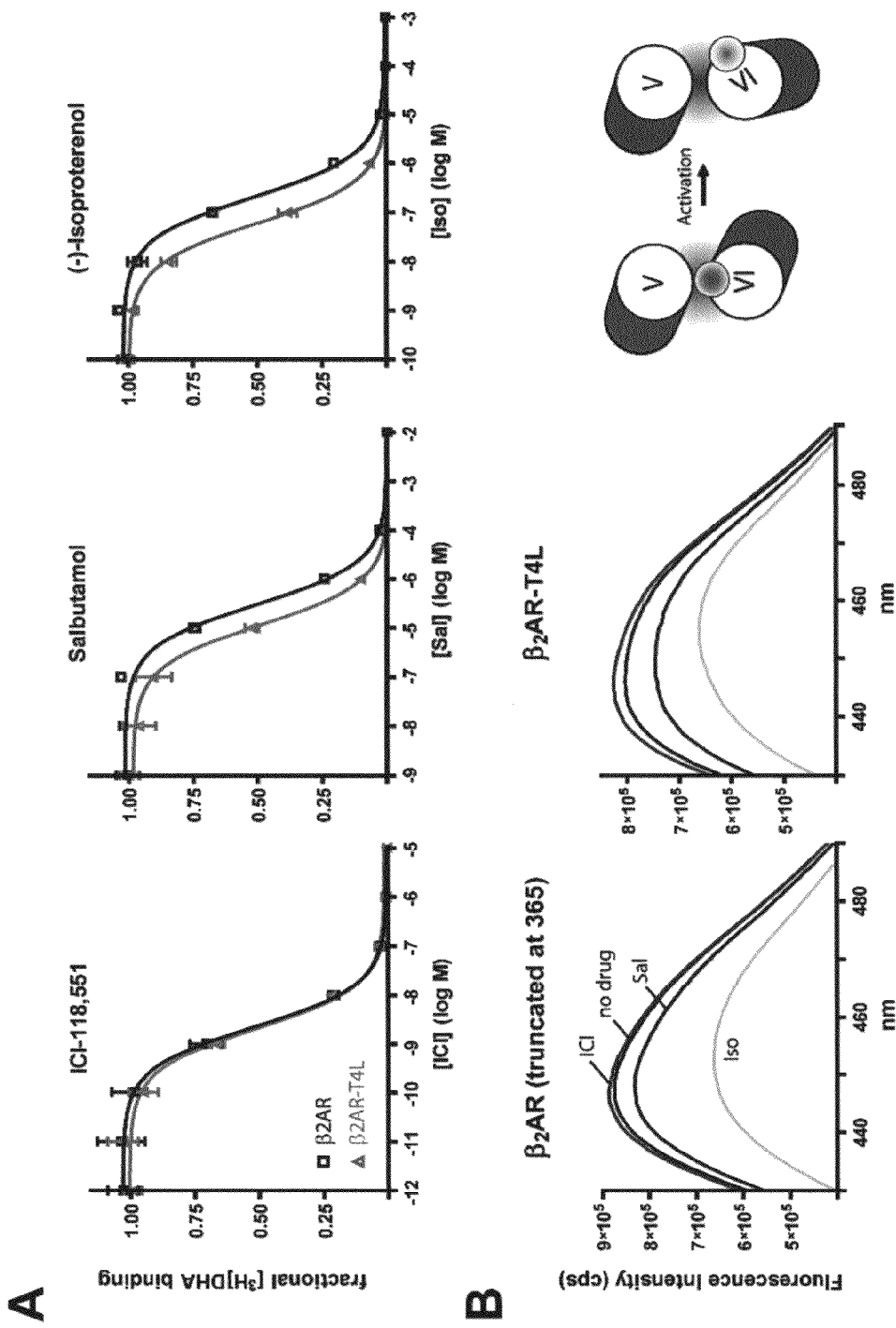
FIG. 4 Functional characterization of $\beta_2$AR-T4L. A. Affinity competition curves for adrenergic ligands binding to $\beta_2$AR-T4L and wild-type $\beta_2$AR. Binding experiments on membranes isolated from Sf9 insect cells expressing the receptors were performed as described below. B. $\beta_2$AR-T4L is still able to undergo ligand-induced conformational changes. Bimane fluorescence spectra (excitation at 350 nm) of detergent-solubilized $\beta_2$AR-T4L and wild-type $\beta_2$AR truncated at 365, labeled under conditions that selectively modify Cys265$^{6.27}$, were measured after incubating unliganded receptor with compounds for 15 min at room temperature. The cartoon illustrates that the observed changes in fluorescence can be interpreted as a movement of the bimane probe from a more buried, hydrophobic environment to a more polar, solvent-exposed position.

The saturation and competition binding curves shown in FIG. 4 were fit to theoretical saturation and one-site competition binding models, using the program Graphpad Prism. $K_i$ values were calculated using the Cheng-Prusoff equation: $K_i = IC_{50}/(1 + [ligand]/K_d)$

TABLE S2

Bimane fluorescence responses for unliganded $\beta_2$AR365 and $\beta_2$AR-T4L, incubated for 15 min with different ligands.

| Ligand | $\lambda$max ± SD for $\beta_2$AR365 (nm) | $\lambda$max ± SD for $\beta_2$AR-T4L (nm) |
| --- | --- | --- |
| none | 448 ± 2 | 447 ± 2 |
| (−)-isoproteronol | 453 ± 2 | 455 ± 2 |
| ICI-118,551 | 447 ± 1 | 446 ± 1 |
| salbutamol | 449 ± 1 | 449 ± 1 |

Intensity at $\lambda$max$_{Ligand}$/Intensity at $\lambda$max$_{none}$

| Ligand | $\beta_2$AR365 | $\beta_2$AR-T4L |
| --- | --- | --- |
| (−)-isoproteronol | 0.758 ± 0.007 | 0.824 ± 0.006 |
| ICI-118,551 | 1.013 ± 0.008 | 1.028 ± 0.008 |
| salbutamol | 0.950 ± 0.013 | 0.928 ± 0.009 |

Top panel shows the $\lambda_{max}$ for fluorescence emission spectra (excitation at 350 nm and emission from 417 to 530 nm) collected after 15 min incubation with ligand. Each value is mean ± standard deviation for triplicate experiments performed in parallel. Bottom panel shows the change in fluorescence intensity after incubation with ligand, represented as the ratio of Intensity at $\lambda$max of the ligand to Intensity at $\lambda_{max}$ of the control no ligand ("none") response.

TABLE S3

Buried surface area contributions at the $\beta_2$AR-T4L/carazolol interface.

| $\beta_2$AR residue | Surface area buried (Å$^2$) |
| --- | --- |
| Trp109$^{3.28}$ | 21.4 |
| Thr110$^{3.29}$ | 5.7 |
| Asp113$^{3.32}$ | 19.3 |
| Val114$^{3.33}$ | 25.5 |
| Val117$^{3.36}$ | 8.5 |
| Thr118$^{3.37}$ | 1.9 |
| Phe193$^{5.32}$ | 51.2 |
| Thr195$^{5.34}$ | 7.4 |
| Tyr199$^{5.38}$ | 7.6 |
| Ala200$^{5.39}$ | 10.0 |
| Ser203$^{5.42}$ | 9.0 |
| Ser204$^{5.43}$ | 4.6 |
| Ser207$^{5.46}$ | 6.3 |
| Trp286$^{6.48}$ | 3.1 |
| Phe289$^{6.51}$ | 20.0 |
| Phe290$^{6.52}$ | 19.0 |
| Phe293$^{6.55}$ | 18.7 |
| Tyr308$^{7.35}$ | 14.4 |
| Asn312$^{7.39}$ | 22.5 |
| Tyr316$^{7.43}$ | 6.5 |

Solvent accessible surface area calculations were done with the CNS software package, using a probe radius of 1.4 Å. Buried surface area contributions of individual residues were determined by calculating solvent-accessible surface area per residue for the full $\beta_2$AR-T4L/carazolol model, and subtracting these numbers from the calculated values for the receptor model without carazolol.

Lipidic Cubic Phase Crystallization

For lipidic cubic phase (LCP) crystallization trials, robotic trials were performed using an in meso crystallization robot. 96-well glass sandwich plates (S1, S2) were filled with 25 or 50 mL protein-laden LCP drops overlaid by 0.8 μL of precipitant solution in each well and sealed with a glass coverslip. All operations starting from mixing lipid and protein were performed at room temperature (~21-23° C.). Crystals were obtained in 30-35% (v/v) PEG 400, 0.1-0.2 M sodium sulfate, 0.1 M Bis-tris propane pH 6.5-7.0 and 5-7% (v/v) 1,4-butanediol using 8-10% (w/w) cholesterol in monoolein as the host lipid. PEG 400 and sulfate ion were used for crystallization, and the addition of cholesterol and 1,4-butanediol improved crystals size and shape enabling high-resolution diffraction. Additions of phospholipids (dioleoylphosphatidylcholine, dioleoylphosphatidylethanolamine, asolectin) alone and in combinations with cholesterol to the main host LCP lipid monoolein were tried, however, none of them improved crystal quality.

Crystal Harvesting

The average size of the harvested crystals was 30×15×5 μm (largest crystal was 40×20×7 μm). Crystals were harvested directly from the glass sandwich plates, even though these plates have been specifically designed for screening and optimization (S1, S2). Crystals were scooped directly from the LCP using 30 or 50 μm aperture MiTeGen MicroMounts and plunged into liquid nitrogen. Care was taken to drag as little as possible lipid around the crystal to decrease unwanted background scattering. Attempts to dissolve the lipids, either by increasing concentration of PEG 400 or using a mineral oil, typically resulted in a decrease in diffraction power of the crystals.

Data Collection

X-ray data were collected on the 23ID-B beamline (GM/CA CAT) at the Advanced Photon Source, Argonne, Ill. using a 10 μm minibeam (wavelength 1.0332 Å) and a MarMosaic 300 CCD detector. Several complete datasets were collected from single crystals at resolution between 2.8 and 3.5 Å using 5× attenuated beam, 5 s exposure and 1° oscillation per frame.

However, some crystals diffracted to a maximum of 2.2 Å resolution upon 5 s exposure with 1× attenuated beam. Therefore, we collected 10-20° wedges of high-resolution data from more than 40 crystals (some of the crystals were large enough to allow 2-3 translations) and combined 31 of the best datasets together from 27 independent crystals, scaling them against the lower resolution full dataset to obtain complete 2.4 Å data.

One of the challenges during data collection was visualization of colorless microcrystals within an opaque frozen lipid phase and aligning them with the 10 µm minibeam. Without being able to visualize the crystals adequately through the inline optics at the beamline, we resorted to alignment by diffraction. After numerous trial-and-error attempts, an optimized crystal search algorithm was designed to locate the crystals without the minibeam. First, the area of the loop containing lipid was scanned in the vertical direction with a highly attenuated and slitted 100×25 µm beam. When diffraction was found, the crystal location was further confined by two additional exposures to an area of ~50×25 µm. This area was further coarse-scanned with the collimated and 10× attenuated minibeam using 15 µm steps, following by fine-tuning the position using 5 and 2 µm steps. After locating the crystal in one orientation the loop was rotated 90° and the procedure was repeated. Typically during alignment the crystal was exposed ~10 times using 10× attenuated beam and 2 s exposures. Work is in progress to develop a fully automated scanning procedure to align invisible microcrystals with the minibeam in place.

Data Processing

A 90% complete, 2-fold redundant monoclinic dataset was processed from one crystal diffracting to 2.8 Å resolution. Initial indexing of lattice parameters in spacegroup C2 and crystal orientation were performed using HKL2000. The refined lattice parameters and space group were implemented in the data processing program XDS for spot integration which models error explicitly for radiation decay, absorption, and rotation. The 2.8 Å data was used as a scaling reference for incorporation of additional wedges of data collected at a much higher exposure. Each new dataset was indexed in XDS using the original unit cell parameters as constants which were then refined along with the crystal orientation, beam geometry, and mosaicity parameters. The refinement was generally stable, resulting in very similar unit cell constants which enabled subsequent scaling. All of the integrated wedges of data were then tested individually against the scaling reference set and included in the final scaled dataset if the merging statistics remained acceptable upon incorporation of the data. In total, 31 wedges of data from 27 crystals were combined with the scaling reference dataset, 22 of which diffracted to a resolution of 2.4 Å or better. Each of the higher resolution datasets were exposed to a much larger dose of radiation resulting in a rapid decay in intensity. Typically 10°-20° wedges were collected from each crystal or translation, 5°-7° of which had diffraction data to 2.4 Å. Based on the mean $F/\sigma(F)$ of reflections near the three crystallographic axes, we estimate the effective resolution to be 2.4 Å along b* and c* and 2.7 Å along a*. The anisotropy results in the high merging R factors in the last few resolution shells despite the significant $1/\sigma(I)$ values. The anisotropy is either an inherent property of the crystals or the result of a preferential orientation of the crystals within the mounting loop. Thus, the higher resolution shells were filled in anisotropically by incorporation of the additional data at high exposure levels, while the lower resolution shells have a very high redundancy and low anisotropy.

EXAMPLE 1

Summary of Results

In order to obtain high-resolution structural information on the $\beta_2AR$, most of the third intracellular loop (ICL3) was replaced by the protein T4 lysozyme (T4L). The C-terminal tail was also eliminated. The optimized $\beta_2AR$-T4L protein was crystallized in lipidic cubic phase, and the resulting 2.4 Å resolution crystal structure reveals the interface between the receptor and the ligand carazolol, a partial inverse agonist. Analysis of mutagenesis data in light of the structure clarifies the roles of different amino acids in inverse agonist binding, and implies that rearrangement of the binding pocket accompanies agonist binding. In addition, the structure reveals how mutations known to cause constitutive activity or uncoupling of agonist binding and G-protein activation are distributed between the ligand-binding pocket and the cytoplasmic surface of the protein, such that changes in side chains due to interaction with the ligand can be transmitted through the structure to the site of G protein interaction.

EXAMPLE 2

$\beta_2AR$-T4L: A Crystallizable GPCR Fusion Protein $\beta_2AR$ crystallization was done by replacing the ICL3 of that protein with a well-structured, soluble domain that aids in the formation of lattice contacts. The initial criteria for choosing the inserted soluble protein were that the amino and carboxyl termini would approximate the predicted distance between the cytoplasmic ends of helix V and helix VI, and that the protein would crystallize under a variety of conditions. T4L is a small, stable protein that fulfills these criteria. The amino and carboxyl termini of wild-type T4L are 10.7 Å apart in PDB 2LZM, compared to a distance of 15.9 Å between the carbonyl carbon of residue $228^{5.63}$ and the amide nitrogen of residue $241^{6.24}$ in the high-resolution structure of rhodopsin (PDB 1U19).

Figure 3:
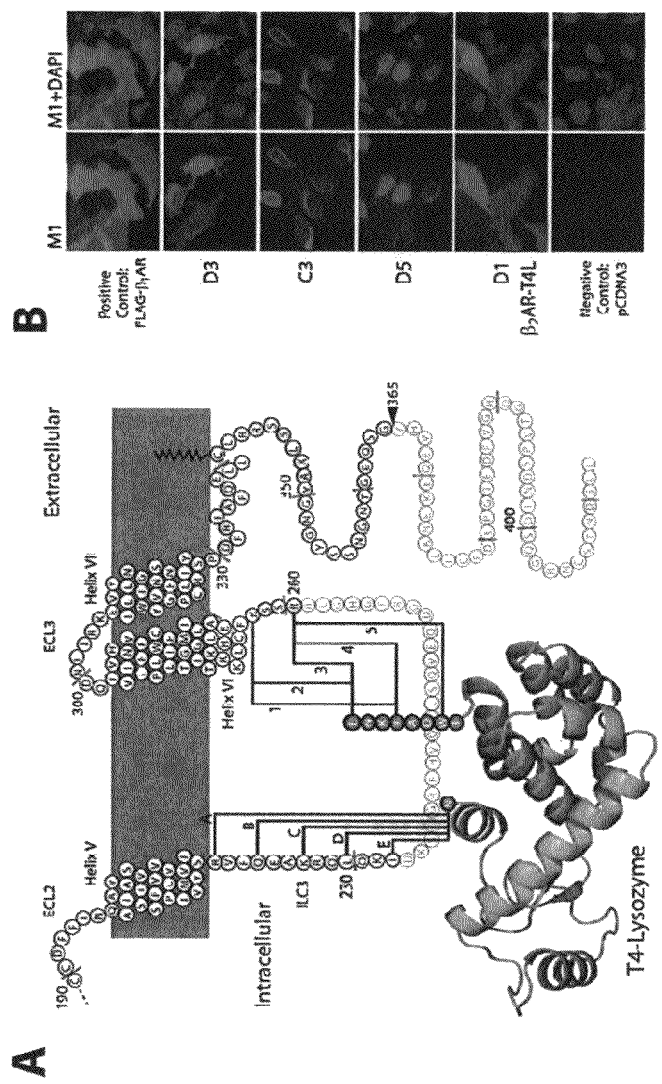
FIG. 3 Design and optimization of the $\beta_2$AR-T4L ($\beta_2$-adrenergic receptor T4 lysozyme) fusion protein. A. The sequence of the region of the $\beta_2$AR ($\beta_2$-adrenergic receptor) targeted for insertion of a crystallizable domain is shown, and the positions of the junctions between the receptor and T4L (T4 lysozyme; in red) for various constructs are indicated. The sequences that were initially replaced or removed are faded. Red lines are shown after every tenth residue. B. Immunofluorescence images of HEK293 cells expressing selected fusion constructs. Panels on the left shows M1 anti-FLAG signal corresponding to antibody bound to the N-terminus of the receptor. Panels on the right show the same signal merged with blue emission from DAPI (nuclear staining for all cells). Plasma membrane staining is observed in the positive control, D3 and D1, while C3 and D5 are retained in the endoplasmic reticulum.

DNA encoding the T4L protein (C54T, C97A) (M. Matsumura, W. J. Becktel, M. Levitt, B. W. Matthews, Proc Natl Acad Sci USA 86, 6562 (1989)) was initially cloned into the human $\beta_2AR$ gene, guided by comparison of ICL3 length and sequence among class A GPCRs (F. Horn et al., Nucleic Acids Res 31, 294 (2003)): residues $234^{5.73}$-$259^{6.21}$ of the $\beta_2AR$ were replaced by residues 2-164 of T4L (construct "E3" in FIG. 3A). In addition, the receptor was truncated at position 365, which aligns approximately with the position of the rhodopsin carboxyl terminus. Although these modifications resulted in a receptor that was expressed efficiently in Sf9 cells, further optimization was carried out to reduce the length of the junction between the receptor and the T4L termini. Several candidate constructs are illustrated in FIG. 3A, and selected immunofluorescence images of transfected, permeabilized HEK293 cells are shown in FIG. 3B. Relative to the initial construct, we could remove three residues from the cytoplasmic end of helix V, three residues from the C-terminal end of T4L, and three residues from the N terminus of helix VI, all without losing significant cell-surface expression. The final construct used for crystallization trials ("$\beta_2AR$-T4L") has residues $231^{5.70}$-$262^{6.24}$ of the $\beta_2AR$ replaced by amino acids 2-161 of T4L ("1D" in FIG. 3A).

EXAMPLE 3

Functional Properties of $\beta_2AR$-T4L

Figure 12:
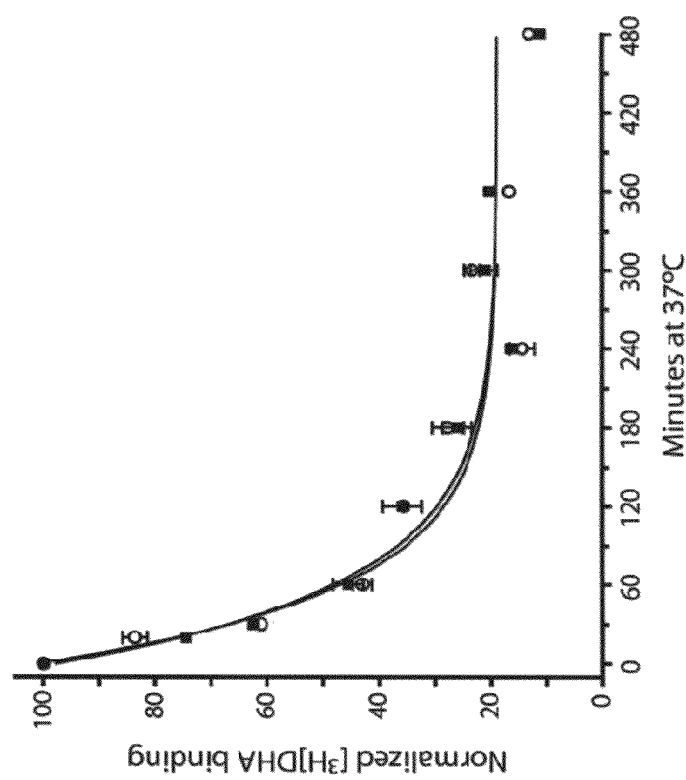
FIG. 12. Stability comparison of unliganded $\beta_2$AR365 and $\beta_2$AR-T4L. For dodecylmaltoside-solubilized receptor preparations, maintenance of the ability to specifically bind [$^3$H]DHA after incubation at 37° C. is taken as a measure of stability.

Saturation binding of [$^3$H]DHA to the $\beta_2AR$-T4L was measured, as well as competition binding of the inverse agonist ICI-118,551 and several agonists (FIGS. 4A and 10 and Table S1). The results show that β$_2$AR-T4L has wild-type affinity for the antagonist [$^3$H]DHA and the inverse agonist ICI-118,551, whereas the affinity for both agonists (isoproterenol, epinephrine, formoterol) and a partial agonist (salbutamol) is two to three-fold higher relative to wild-type β$_2$AR. Higher agonist binding affinity is a property associated with constitutively active mutants (CAMs) of GPCRs. CAMs of the β$_2$AR also exhibit elevated basal, agonist-independent activation of Gs, and typically have lower expression levels and reduced stability. β$_2$AR-T4L exhibits binding properties of a CAM, but it expresses at levels exceeding 1 mg per liter of Sf9 cell culture, is more resistant to trypsin proteolysis than the wild-type β$_2$AR (FIG. 11), and retains binding activity in detergent at 37° C. as well as the wild-type receptor (FIG. 12).

β$_2$AR-T4L did not couple to G$_s$, as expected due to the replacement of ICL3 by T4L. To assess whether the fused protein alters receptor function at the level of its ability to undergo conformational changes, we used a covalently attached fluorescent probe as a reporter for ligand-induced structural changes. Fluorophores attached at Cys265$^{6.27}$, at the cytoplasmic end of helix VI, detect agonist-induced conformational changes that correlate with the efficacy of the agonist towards G protein activation. Detergent-solubilized β$_2$AR365 (wild-type receptor truncated at 365) and β$_2$AR-T4L were each labeled with monobromobimane, which has been used previously to monitor conformational changes of the β$_2$AR. Addition of the agonist isoproterenol to purified β$_2$AR365 induces a decrease in fluorescence intensity and a shift in $\lambda_{max}$ for the attached bimane probe (FIG. 4B and Table S2). These changes in intensity and $\lambda_{max}$ are consistent with an agonist-induced increase in polarity around bimane. A smaller change is observed with the partial agonist salbutamol, while the inverse agonist ICI-118,551 had little effect. For the β$_2$AR-T4L, there are subtle differences in the baseline spectrum of the bimane-labeled fusion protein, as might be expected if the environment around Cys265$^{6.27}$ is altered by T4L. However, the full agonist isoproterenol induces a qualitatively similar decrease in intensity and rightward shift in $\lambda_{max}$. Thus the presence of the fused T4L does not prevent agonist-induced conformational changes. The partial agonist salbutamol induced larger responses in β$_2$AR-T4L than were observed in wild-type β$_2$AR, and there was a small increase in fluorescence in response to the inverse agonist ICI-118,551. These are properties observed in CAMs and are consistent with the higher affinities for agonists and partial agonists exhibited by β$_2$AR-T4L. Therefore, we conclude that the T4L fusion induces a partial constitutively active phenotype in the β$_2$AR, likely caused by changes at the cytoplasmic ends of helices V and VI.

EXAMPLE 4

Comparison Between β$_2$AR-T4L and AR-Fab Structures

Figure 5:
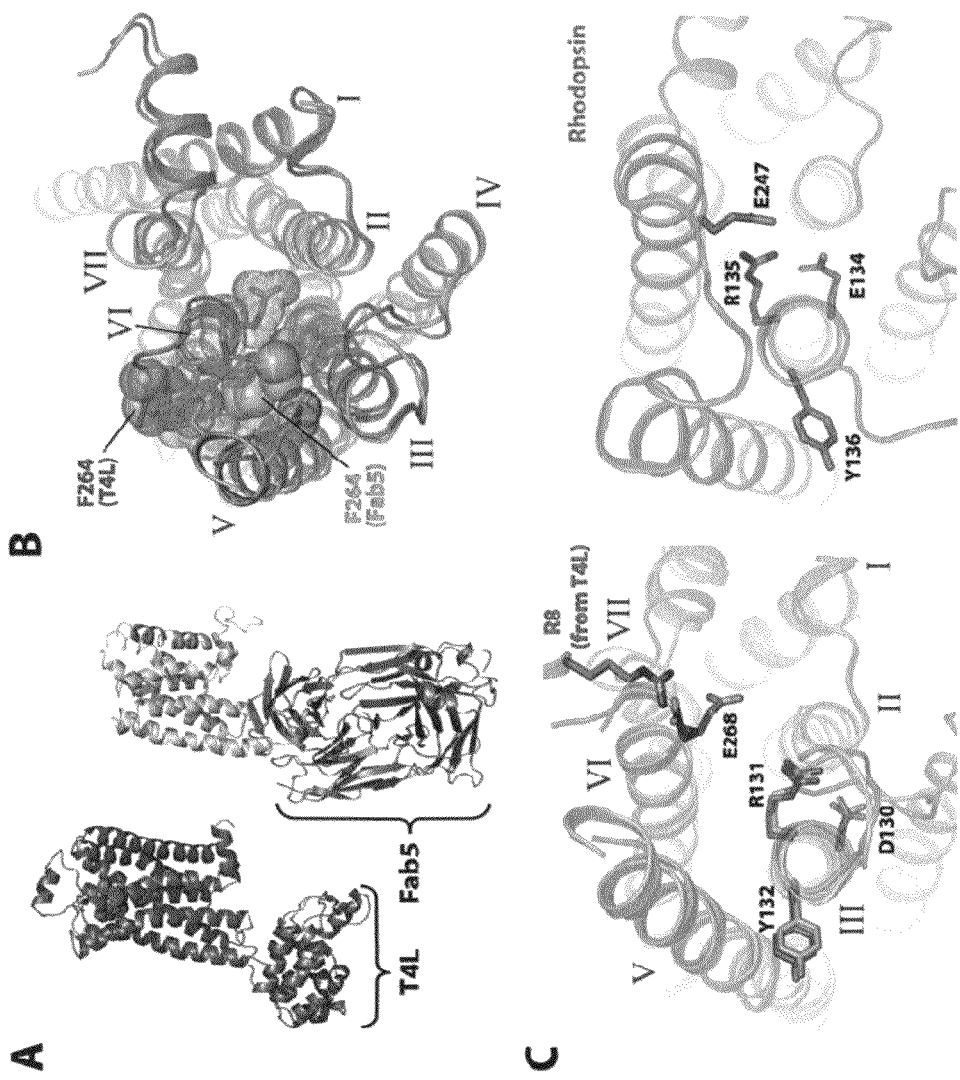
FIG. 5. A. Side-by-side comparison of the crystal structures of the $\beta_2$AR-T4L fusion protein and the complex between $\beta_2$AR365 and a Fab fragment. The receptor component of the fusion protein is shown as a blue cartoon (with modeled carazolol as red spheres), while the receptor bound to Fab5 is in yellow. B. Differences in the environment surrounding Phe264$^{6.26}$ (shown as spheres) for the two proteins. C. The analogous interactions to the "ionic lock" between the E(D)RY motif and Glu247$^{6.30}$ seen in rhodopsin (right panel, purple) are broken in both structures of the $\beta_2$AR (left panel, colored blue and yellow as above). Pymol was used for the preparation of all figures.
Figure 13:
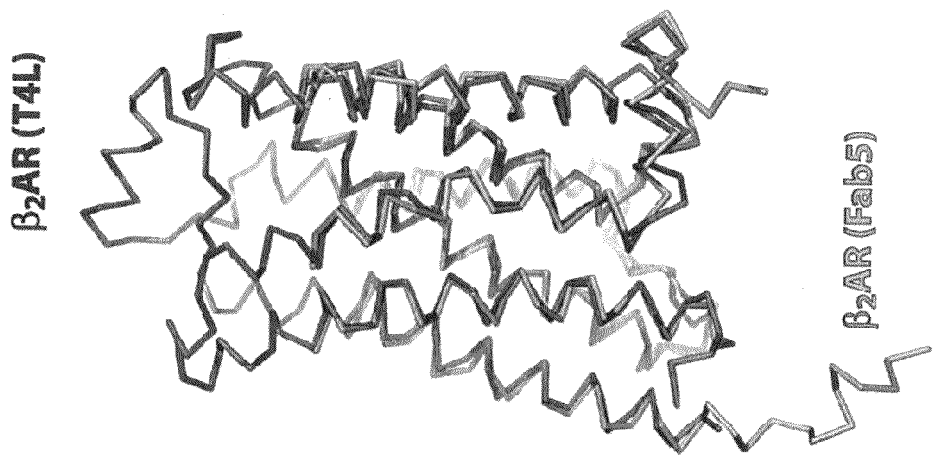
FIG. 13. Superimposed Cα traces of the receptor component of $\beta_2$AR-T4L (in blue) and $\beta_2$AR365 (in yellow). Common modeled transmembrane helix regions 41-58, 67-87, 108-137, 147-164, 204-230, 267-291, 312-326, 332-339 were used in the superposition by the program Lsqkab (RMSD=0.8 Å).

The β$_2$AR-T4L fusion strategy is validated by comparison of its structure to the structure of wild-type β$_2$AR complexed with a Fab that recognizes a three dimensional epitope consisting of the amino and carboxyl-terminal ends of ICL3, determined at an anisotropic resolution of 3.4 Å/3.7 Å. FIG. 5A illustrates the similarity between the fusion and antibody complex approaches to β$_2$AR crystallization, in that both strategies rely on attachment (covalent or non-covalent, respectively) of a soluble protein partner between helices V and VI. A major difference between the two structures is that the extracellular loops and the carazolol ligand could not be modeled in the β$_2$AR-Fab complex, whereas these regions are resolved in the structure of β$_2$AR-T4L. Nonetheless, it is clear that the T4L insertion does not significantly alter the receptor. Superposition of the two structures (FIG. 13) illustrates that the transmembrane helices of the receptor components are very similar (RMSD=0.8 Å for 154 common modeled transmembrane Cα positions, versus 2.3 Å between β$_2$AR-T4L and the 154 equivalent residues in rhodopsin), especially when the modest resolution of the Fab complex is taken into account.

There is one significant difference between the Fab-complex and chimeric receptor structures that can be attributed to the presence of T4L. The cytoplasmic end of helix VI is pulled outward as a result of the fusion to the carboxyl terminus of T4L, which alters the packing of Phe264$^{6.26}$ at the end of helix VI (FIG. 5B). In the Fab-complex β$_2$AR, interactions between Phe264$^{6.26}$ and residues in helix V, helix VI, and ICL2 may be important in maintaining the β$_2$AR in the basal state. The loss of these packing interactions in β$_2$AR-T4L could contribute to the higher agonist binding affinity characteristic of a CAM.

An unexpected difference between the structure of rhodopsin and the β$_2$AR-T4L involves the sequence E/DRY found at the cytoplasmic end of helix III in 71% of class A GPCRs. In rhodopsin, Glu134$^{3.49}$ and Arg135$^{3.50}$ form a network of hydrogen bond and ionic interactions with Glu247$^{6.30}$ at the cytoplasmic end of helix VI. These interactions have been referred to as an "ionic lock" that stabilizes the inactive state of rhodopsin and other class A members. However, the arrangement of the homologous residues is significantly different in β$_2$AR-T4L: Arg131$^{3.50}$ interacts primarily with Asp130$^{3.49}$ and a sulfate ion rather than with Glu268$^{6.30}$, and the distance between helix III and helix VI is greater than in rhodopsin (FIG. 5C). This difference might be explained by the interaction between Glu268$^{6.30}$ and Arg8 of T4L; however, the arrangement of Asp 130$^{3.49}$ and Arg131$^{3.50}$ and the distance between helix III and helix VI is very similar to that observed in the β$_2$AR-Fab structure. While the presence of an antibody or T4L at the ICL3 region could potentially affect the arrangement of these residues, the fact that similar ionic lock structures were obtained using two different approaches suggests that a broken ionic lock may be a genuine feature of the carazolol-bound state of the receptor.

EXAMPLE 5

Ligand Binding to the β$_2$AR

Figure 6:
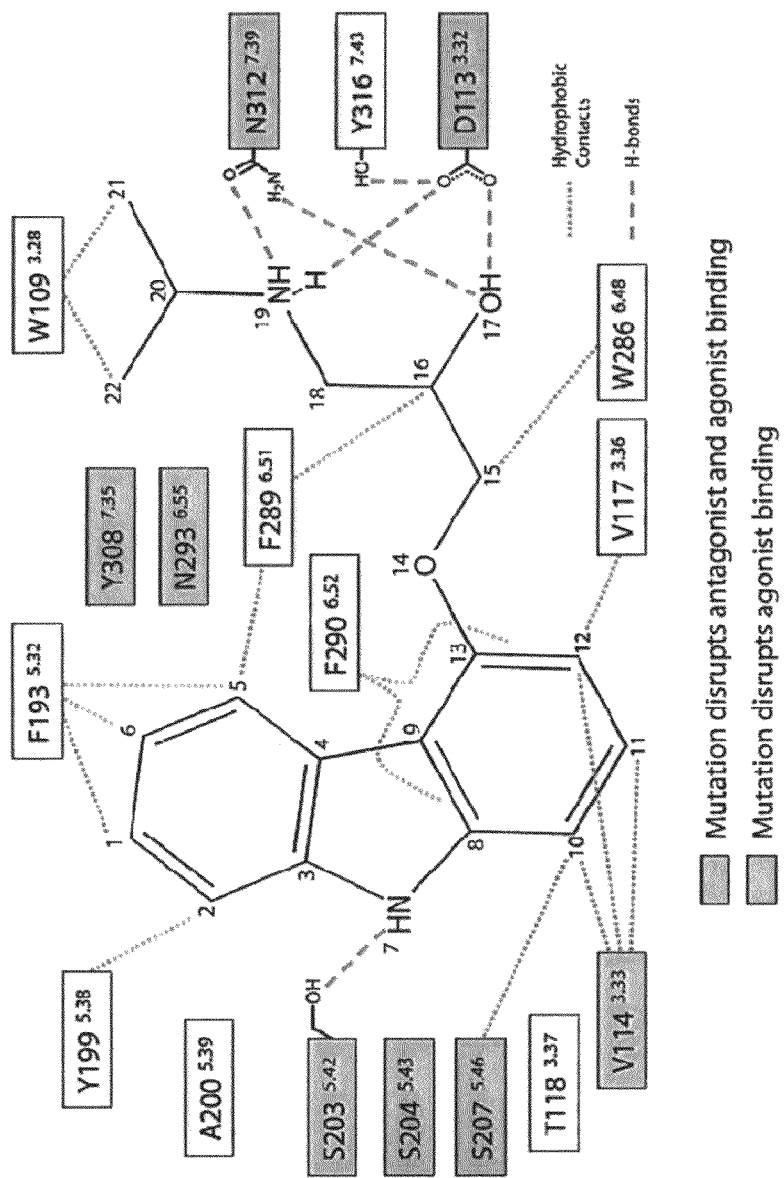
FIG. 6. Schematic representation of the interactions between $\beta_2$AR-T4L and carazolol at the ligand binding pocket. Residues shown have at least one atom within 4 Å of the ligand in the 2.4 Å resolution crystal structure.
Figure 7:
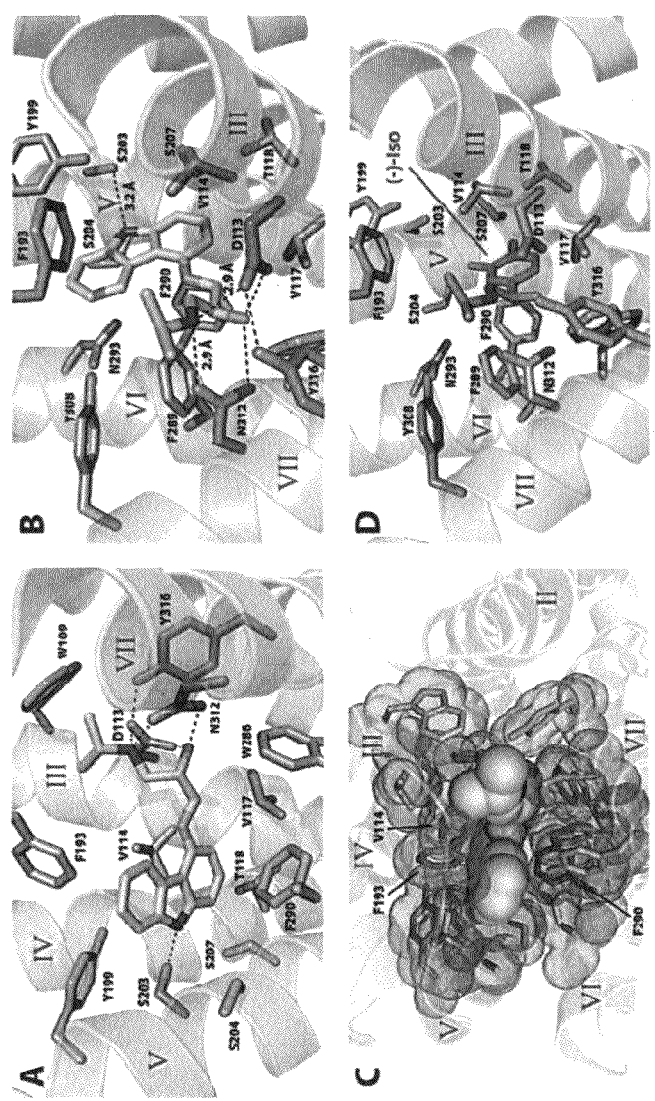
FIG. 7. The ligand binding pocket of $\beta_2$AR-T4L with carazolol bound. A. Residues within 4 Å of the ligand are shown as sticks, with the exception of A200, N293, F289, and Y308. Residues that form polar contacts with the ligand (distance cutoff 3.5 Å) are in green, other residues are gray (in all panels, oxygens are colored red and nitrogens are blue). B. Same as panel A, except that the ligand is oriented with its amine facing out of the page. W109 is not shown. C. Packing interactions between carazolol and all residues within 5 Å of the ligand. View is from the extracellular side of the membrane. Carazolol is shown as yellow spheres, receptor residues are shown as sticks within van der Waals dot surfaces. Val114$^{3.33}$, Phe193$^{5.32}$, and Phe290$^{6.52}$ are colored red, all other residues are gray. D. Model of (−)-isoproterenol (magenta sticks) in the ligand binding pocket observed in the crystal structure. A model of the agonist with optimal bond lengths and angles was obtained from the PRODRG server, and the dihedral angles were adjusted to the values observed in the homologous atoms of bound carazolol (16-22 in FIG. 6). The one remaining unaccounted dihedral in (−)-isoproterenol was adjusted in order to place the catechol ring in the same plane as the $C_{16}$—$C_{15}$—$O_{14}$ plane in carazolol. Residues known to specifically interact with agonists are shown as green sticks.
Figure 14:
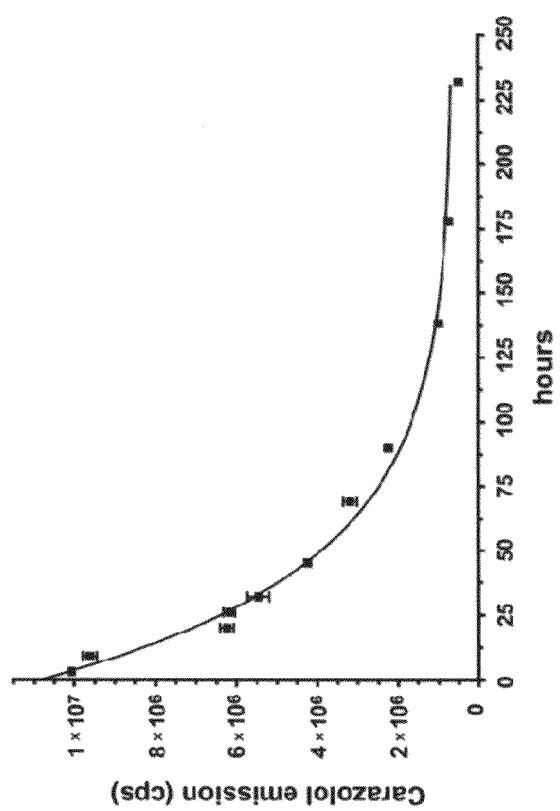
FIG. 14. Carazolol dissociation from $\beta_2$AR365. Dodecylmaltoside-solubilized carazolol-bound receptor (at 50 μM) was dialyzed in a large volume of buffer containing 300 micromolar alprenonol as a competing ligand, and aliquots were removed from the dialysis cassette at different time points. Remaining bound carazolol was measured (in a relative sense) by collecting fluorescence emission with excitation at 330 nm and emission from 335 to 400 nm. For each carazolol fluorescence measurement, data was normalized for the protein concentration in the dialysis cassette (measured with the Bio-Rad Protein DC kit). The Y-axis represents carazolol fluorescence emission Intensity (in cps) at 341 nm. The exponential decay of carazolol concentration in the receptor dialysis cassette was fit using Graphpad Prism software, giving a half-life of 30.4 hrs.

The β$_2$AR-T4L fusion protein was purified and crystallized in complex with the inverse agonist carazolol. Carazolol stabilizes the β$_2$AR against extremes of pH and temperature, perhaps related to its unusually high binding affinity ($K_d$<0.1 nM) and slow dissociation kinetics ($t_{1/2}$~30 h) (FIG. 14). The interactions between carazolol and β$_2$AR-T4L are depicted schematically in FIG. 6. The carbazole ring system is oriented roughly perpendicular to the plane of the membrane, and the alkylamine chain (atoms 15-22 in the model) is nearly parallel to the heterocycle (FIG. 7A-B). Carazolol was modeled into the electron density (3) as the (S)-(−) isomer due to the higher affinity of this enantiomer, despite the fact that a racemic mixture of the ligand was used in crystallization. Asp113$^{3.32}$, Tyr316$^{7.43}$, and Asn312$^{7.39}$ present a constellation of polar functional groups to the alkylamine and alcohol moieties of the ligand, with Asp113$^{3.32}$ and Asn312$^{7.39}$ sidechains forming close contacts (<3A) with O$_{17}$ and N$_{19}$ atoms of carazolol (FIGS. 6 and 7A-B). Asp113$^{3.32}$ was one of the first β$_2$AR residues shown to be important for ligand binding; notably the D113N mutation causes complete loss of detectable affinity for antagonists and a decrease in the potency of agonists towards cell-based G protein activation by over 4 orders of magnitude. Likewise, mutations of Asn312$^{7.39}$ perturb $\beta_2$AR binding to agonists and antagonists: changes to nonpolar amino acids (Ala or Phe) reduce affinities to undetectable levels, while retention of a polar functionality (Thr or Gln) gives partial affinity. On the opposite end of the ligand near helix V, N$_7$ of the carbazole heterocycle forms a hydrogen bond with the side chain hydroxyl of Ser203$^{5.42}$. Interestingly, mutations of Ser203$^{5.42}$ specifically decrease $\beta_2$AR affinity towards catecholamine agonists and aryloxyalkylamine ligands with nitrogen-containing heterocycles such as pindolol, and by implication carazolol. Thus, the polar interactions between carazolol and the receptor observed in the crystal structure agree with the known biochemical data. The contribution of Tyr316$^{7.43}$ to antagonist and agonist affinity remains to be tested; this residue is conserved as tyrosine in all sequenced adrenergic receptor genes.

FIG. 7C shows the tight packing between carazolol and surrounding amino acids that buries 790 Å$^2$ of surface area from solvent; specific contacts are depicted schematically in FIG. 6. Notable among the hydrophobic residues contacting carazolol are Val114$^{3.33}$, Phe290$^{6.52}$, and Phe193$^{5.32}$. The side chain of Val114$^{3.33}$ from helix III makes multiple contacts with the C$_8$-C$_{13}$ ring of the carbazole heterocycle, and Phe290$^{6.52}$ from helix VI forms an edge-to-face aromatic interaction with the same ring. As a result, these two amino acids form a hydrophobic "sandwich" with the portion of the aryl moiety that is common to many adrenergic antagonists. Mutation of Val14$^{3.33}$ to alanine was shown to decrease $\beta_2$AR affinity towards the antagonist alprenolol by an order of magnitude, as well as lowering affinity for the agonist epinephrine 300-fold. Phe193$^{5.32}$ is different from other carazolol contact residues in that it is located on the ECL2, in the path of hormone accessibility to the binding pocket. This amino acid contributes more buried surface area than any other residue to the interface between $\beta_2$AR-T4L and carazolol (see Table S3). Therefore, Phe193$^{5.32}$ is likely to contribute significantly to the energy of $\beta_2$AR-carazolol complex formation, and the position of this residue on the extracellular side of the binding site may allow it to act as a gate that contributes to the unusually slow dissociation of the ligand (FIG. 14).

Figure 15:
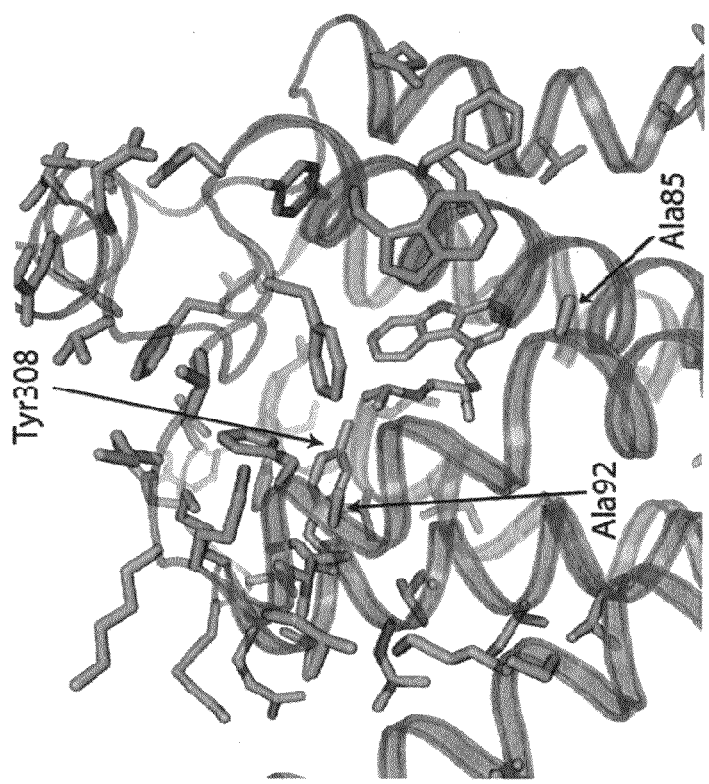
FIG. 15. After aligning the $\beta_1$ and $\beta_2$AR sequences, positions that have different amino acids between the two receptors were mapped onto the high-resolution structure of $\beta_2$AR-T4L (shown as red sticks). The carazolol ligand is shown as green sticks (with nitrogens in blue and oxygens in red). Highlighted residues Ala85$^{2.56}$, Ala92$^{2.63}$ and Tyr308$^{7.35}$ are homologous to amino acids Leu110$^{2.56}$, Thr117$^{2.63}$ and Phe359$^{7.35}$ of the $\beta_1$AR, which were shown to be primarily responsible for its selectivity over $\beta_2$AR for the compound RO363. In the $\beta_2$AR-T4L structure, only Tyr308$^{7.35}$ faces the ligand, while Ala85$^{2.56}$ lies at the interface between helices II and III. Of all the divergent amino acids, only Tyr308$^{7.35}$ is found within 4 Å of any atom of carazolol.

Analysis of the binding pocket provides insights into the structural basis for pharmacologic selectivity between the $\beta_2$AR and closely related adrenergic receptors such as the $\beta_1$AR. The affinities of these two receptors for certain ligands, such as ICI-118,551, betaxolol and RO363, differ by up to 100-fold. Curiously, all of the amino acids in the carazolol binding pocket are conserved between the $\beta_1$AR and $\beta_2$AR (see FIG. 15). The majority of the 94 amino acid differences between the $\beta_1$AR and $\beta_2$AR are found in the cytoplasmic and extracellular loops. While residues that differ in the transmembrane segments generally face the lipid bilayer, eight residues lie at the interface between helices and may influence helix packing. The structural basis for pharmacologic differences between $\beta_1$AR and $\beta_2$AR must, therefore, arise from amino acid differences in the entrance to the binding pocket or subtle differences in the packing of helices. Evidence for the latter comes from chimeric receptor studies in which successive exchange of helices between $\beta_1$AR and $\beta_2$ARs led to a gradual change in affinity for the $\beta_2$AR selective ICI-118, 551 and the $\beta_1$AR selective betaxolol.

As discussed above, $\beta_2$AR-T4L shows CAM-like properties with respect to agonist binding affinities, suggesting that the unliganded $\beta_2$AR-T4L may exist in a more active conformation than the wild type-$\beta_2$AR. Nevertheless, as shown in FIG. 4B, $\beta_2$AR-T4L can be stabilized in an inactive conformation by an inverse agonist. Since $\beta_2$AR-T4L was crystallized with bound carazolol, a partial inverse agonist, the structure most likely represents an inactive state. This is consistent with the similarity of the $\beta_2$AR-T4L and $\beta_2$AR-Fab5 carazolol-bound structures. To assess whether conformational changes are required to accommodate catecholamines, a model of isoproterenol was placed in the binding site such that common atoms (16-22 in FIG. 6) were superimposed onto the analogous carazolol coordinates in the crystal structure (FIG. 7D). Residues Ser204$^{5.43}$ and Ser207$^{5.46}$ are critical for catecholamine binding and activation of the $\beta_2$AR, with Ser204$^{5.43}$ hydrogen bonding to the meta-hydroxyl and Ser207$^{5.46}$ to the para-hydroxyl of the catechol ring, respectively. In our model, the catechol hydroxyls of isoproterenol face the appropriate serines on helix V, but the distances are too long for hydrogen bonding (6.8 Å from meta-hydroxyl oxygen to the sidechain oxygen of Ser204$^{5.43}$, 4.8 Å from the para-hydroxyl oxygen to the sidechain oxygen of Ser207$^{5.46}$). In addition, Asn293$^{6.55}$ and Tyr308$^{7.35}$, two residues expected to form selective interactions with agonists based on the literature, are too distant to form productive polar or hydrophobic contacts with the modeled isoproterenol molecule. These observations suggest that agonist binding requires changes in the binding site relative to the carazolol-bound structure, unless common structural components of agonists and inverse agonists bind in a significantly different manner.

EXAMPLE 6

Structural Insights into $\beta_2$AR Activation

Biophysical studies provide evidence that conformational changes associated with activation of the $\beta_2$AR are similar to those observed for rhodopsin. Yet the highly efficient process of light activation of rhodopsin through the cis-trans isomerization of covalently bound retinal is very different from activation of the $\beta_2$AR and other GPCRs by diffusible hormones and neurotransmitters. Despite representing a static picture of the inverse agonist-bound state, the crystal structure of $\beta_2$AR-T4L still shows how agonist binding is translated into structural changes in the cytoplasmic domains of receptor. Agonist binding occurs at the extracellular ends of helices III, IV, V and VII, and G protein activation is mediated by the cytoplasmic ends. While the structure is open at the extracellular face to form the ligand binding pocket, the helices are more closely packed in the intracellular half of the receptor. This close packing implies that isolated rigid-body movement of any of these helices is unlikely, and that conformational changes can only be accomplished by rearrangement of side chains forming the network of interactions between the helices. Biophysical studies show that structurally different agonists stabilize distinct active states, suggesting that different ligands could stabilize different combinations of side chain rearrangements.

Analysis of mutations that affect $\beta_2$AR function provides insights into structural rearrangements that are likely to occur during receptor activation. FIG. 8A illustrates the location of amino acids for which mutations lead to elevated basal, agonist-independent activity (constitutively active mutations, CAMs), as well as amino acids for which mutations impair agonist activation (uncoupling mutations, UCMs). Residues for which CAMs have been described are likely to be involved in interactions that maintain the receptor in the inactive conformation. These amino acids are centrally located on helices III and VI. In contrast, positions in which UCMs have been observed are likely to form intramolecular interactions that stabilize the active state. A cluster of UCMs are found at the cytoplasmic end of helix VII. Neither CAMs nor UCMs are directly involved in agonist binding. Although the CAMs and UCMs are not directly connected in sequence, it is evident from the structure that they are linked through packing interactions, such that movements in one will likely affect the packing of others. For example, FIG. 8A (right panel) shows all amino acids with atoms within 4 Å of the two centrally located CAMs, Leu124$^{3.43}$ and Leu272$^{6.34}$. Several amino acids that pack against these CAMs also interact with one or more UCMs. Trp286$^{6.48}$ lies at the base of the binding pocket. It has been proposed that agonist binding leads to a change in the rotameric state of Trp286$^{6.48}$ with subsequent changes in the angle of the helical kink formed by Pro288$^{6.50}$. It is likely that an agonist-induced change in the rotameric state of Trp286$^{6.48}$ will be linked to changes in sidechains of CAMs and UCMs through packing interactions and propagated to the cytoplasmic ends of the helices and the associated intracellular loops that interact with G proteins and other signaling molecules.

In the structures of both rhodopsin and the $\beta_2$AR, a cluster of water molecules lies near the most highly conserved class A GPCR residues (FIG. 8B). It has been proposed that these water molecules may play a role in the structural changes involved in receptor activation. FIG. 8C shows the network of potential hydrogen bonding interactions that link Trp286$^{6.48}$ with conserved amino acids extending to the cytoplasmic ends of helices. UCMs have been identified for three amino acids linked by this network -N322$^{7.49}$, P323$^{7.50}$, and Y326$^{7.53}$. This relatively loose-packed, water filled region is likely to be important in allowing conformational transitions, as there will be fewer steric restraints to sidechain repacking. Future structures of the agonist-bound state of the $\beta_2$AR will help to clarify the precise rearrangements that accompany activation of the receptor.

What is claimed is:

1. A method for crystallizing a GPCR, comprising:
   a) isolating a GPCR fusion protein comprising, from N-terminus to C-terminus:
      i. a first portion of a G-protein coupled receptor (GPCR), wherein said first portion comprises TM1, TM2, TM3, TM4 and TM5 regions of said GPCR;
      ii. a domain comprising the amino acid sequence of a lysozyme; and
      iii. a second portion of said GPCR, wherein said second portion comprises TM6 and TM7 regions of said GPCR, to produce an isolated GPCR fusion protein; and
   b) crystallizing said isolated GPCR fusion protein, thereby producing said crystal.

2. The method of claim 1, wherein said crystallizing is done in a lipid environment.

3. The method of claim 1, wherein said crystallizing is done by lipid cubic phase crystallization.

4. The method of claim 1, wherein said crystallizing is done by bicelle crystallization.

5. The method of claim 1, wherein said method comprises combining said isolated GPCR fusion protein with a ligand prior to said crystallizing.

6. The method of claim 1, wherein said domain comprises an amino acid sequence having at least 80% identity to the amino acid sequence of a wild-type lysozyme.

7. The method of claim 1, wherein said domain comprises an amino acid sequence having at least 95% identity to a wild-type lysozyme.

8. The method of claim 1, wherein said domain comprises an amino acid sequence that is at least 95% identical to the amino acid sequence of T4 lysozyme.

9. The method of claim 1, wherein said first and second portions of said GPCR comprise the amino acid sequence of a naturally occurring GPCR.

10. The method of claim 1, wherein said first and second portions of said GPCR comprise the amino acid sequence of a non-naturally occurring GPCR.

11. The method of claim 1, wherein the amino acid sequence of said first and second portions of said GPCR are least 80% identical to amino acid sequences of a wild type GPCR.

12. The method of claim 1, wherein said a GPCR is selected from the group consisting of: a receptor for a biogenic amine, a dopamine receptor, a seratonin receptor, an adrenergic receptor, aβ2-adrenergic receptor, a melanocortin receptor subtype 4, a ghrelin receptor, a metabotropic glutamate receptor and a chemokine receptor.

13. The method of claim 1, wherein said domain is in the range of from 100 to 200 amino acids in length.

14. A method for producing a crystal comprising:
   a) isolating a polypeptide comprising, from N-terminus to C-terminus:
      i. a first portion of a G-protein coupled receptor (GPCR), wherein said first portion comprises the amino acid sequence that is N-terminal to the IC3 loop of said GPCR;
      ii. a domain comprising the amino acid sequence of a lysozyme; and
      iii. a second portion of said GPCR, wherein said second portion comprises the amino acid sequence that is C-terminal to the IC3 loop of said GPCR, to produce an isolated polypeptide; and
   b) crystallizing said isolated polypeptide, thereby producing said crystal.

15. The method of claim 14, wherein said domain spaces the C-terminal end of the first portion of said GPCR and the N-terminal end of the second portion of said GPCR so that the closest alpha carbon atoms at said C-terminal end and said N-terminal end are spaced by a distance of in the range of 6 Å to 16 Å.

16. The method of claim 14, wherein the amino acid sequence of said first and second portions of said GPCR are least 80% identical to amino acid sequences of a wild type GPCR.

17. The method of claim 14, wherein said domain comprises an amino acid sequence having at least 80% identity to the amino acid sequence of a wild-type lysozyme.

18. A method for producing a crystal comprising:
   a) isolating a G-protein coupled receptor (GPCR) comprising an IC3 loop containing a substitution that comprises the amino acid sequence of a lysozyme to produce an isolated GPCR; and
   b) crystallizing said isolated GPCR, thereby producing said crystal.

19. The method of claim 18, wherein said crystallizing is done by lipid cubidic phase crystallization.

20. The method of claim 18, wherein said crystallizing is done by bicelle crystallization.

* * * * *

SEQUENCE LISTING

```
<160> NUMBER OF SEQ ID NOS: 40

<210> SEQ ID NO 1
<211> LENGTH: 501
<212> TYPE: PRT
<213> ORGANISM: Artificial Sequence
<220> FEATURE:
<223> OTHER INFORMATION: synthetic polypeptide

<400> SEQUENCE: 1

Asp Tyr Lys Asp Asp Asp Ala Met Gly Gln Pro Gly Asn Gly Ser
1               5                   10                  15

Ala Phe Leu Leu Ala Pro Asn Arg Ser His Ala Pro Asp His Asp Val
            20                  25                  30

Thr Gln Gln Arg Asp Glu Val Trp Val Val Gly Met Gly Ile Val Met
        35                  40                  45

Ser Leu Ile Val Leu Ala Ile Val Phe Gly Asn Val Leu Val Ile Thr
    50                  55                  60

Ala Ile Ala Lys Phe Glu Arg Leu Gln Thr Val Thr Asn Tyr Phe Ile
65                  70                  75                  80

Thr Ser Leu Ala Cys Ala Asp Leu Val Met Gly Leu Ala Val Val Pro
                85                  90                  95

Phe Gly Ala Ala His Ile Leu Met Lys Met Trp Thr Phe Gly Asn Phe
            100                 105                 110

Trp Cys Glu Phe Trp Thr Ser Ile Asp Val Leu Cys Val Thr Ala Ser
        115                 120                 125

Ile Glu Thr Leu Cys Val Ile Ala Val Asp Arg Tyr Phe Ala Ile Thr
    130                 135                 140

Ser Pro Phe Lys Tyr Gln Ser Leu Leu Thr Lys Asn Lys Ala Arg Val
145                 150                 155                 160

Ile Ile Leu Met Val Trp Ile Val Ser Gly Leu Thr Ser Phe Leu Pro
                165                 170                 175

Ile Gln Met His Trp Tyr Arg Ala Thr His Gln Glu Ala Ile Asn Cys
            180                 185                 190

Tyr Ala Glu Glu Thr Cys Cys Asp Phe Phe Thr Asn Gln Ala Tyr Ala
        195                 200                 205

Ile Ala Ser Ser Ile Val Ser Phe Tyr Val Pro Leu Val Ile Met Val
    210                 215                 220

Phe Val Tyr Ser Arg Val Phe Gln Glu Ala Lys Arg Gln Leu Asn Ile
```

```
                        225                 230                 235                 240
        Phe Glu Met Leu Arg Ile Asp Glu Gly Leu Arg Leu Lys Ile Tyr Lys
                        245                 250                 255
        Asp Thr Glu Gly Tyr Tyr Thr Ile Gly Ile Gly His Leu Leu Thr Lys
                        260                 265                 270
        Ser Pro Ser Leu Asn Ala Ala Lys Ser Glu Leu Asp Lys Ala Ile Gly
                        275                 280                 285
        Arg Asn Thr Asn Gly Val Ile Thr Lys Asp Glu Ala Glu Lys Leu Phe
                        290                 295                 300
        Asn Gln Asp Val Asp Ala Ala Val Arg Gly Ile Leu Arg Asn Ala Lys
        305                 310                 315                 320
        Leu Lys Pro Val Tyr Asp Ser Leu Asp Ala Val Arg Arg Ala Ala Leu
                        325                 330                 335
        Ile Asn Met Val Phe Gln Met Gly Glu Thr Gly Val Ala Gly Phe Thr
                        340                 345                 350
        Asn Ser Leu Arg Met Leu Gln Gln Lys Arg Trp Asp Glu Ala Ala Val
                        355                 360                 365
        Asn Leu Ala Lys Ser Arg Trp Tyr Asn Gln Thr Pro Asn Arg Ala Lys
                        370                 375                 380
        Arg Val Ile Thr Thr Phe Arg Thr Gly Thr Trp Asp Ala Tyr Lys Phe
        385                 390                 395                 400
        Cys Leu Lys Glu His Lys Ala Leu Lys Thr Leu Gly Ile Ile Met Gly
                        405                 410                 415
        Thr Phe Thr Leu Cys Trp Leu Pro Phe Phe Ile Val Asn Ile Val His
                        420                 425                 430
        Val Ile Gln Asp Asn Leu Ile Arg Lys Glu Val Tyr Ile Leu Leu Asn
                        435                 440                 445
        Trp Ile Gly Tyr Val Asn Ser Gly Phe Asn Pro Leu Ile Tyr Cys Arg
                        450                 455                 460
        Ser Pro Asp Phe Arg Ile Ala Phe Gln Glu Leu Leu Cys Leu Arg Arg
        465                 470                 475                 480
        Ser Ser Leu Lys Ala Tyr Gly Asn Gly Tyr Ser Ser Asn Gly Asn Thr
                        485                 490                 495
        Gly Glu Gln Ser Gly
                        500

<210> SEQ ID NO 2
<211> LENGTH: 1551
<212> TYPE: DNA
<213> ORGANISM: Artificial Sequence
<220> FEATURE:
<223> OTHER INFORMATION: synthetic oligonucleotide

<400> SEQUENCE: 2
atgaagacga tcatcgccct gagctacatc ttctgcctgg tgttcgccga ctacaaggac     60
gatgatgacg ccatgggggca acccgggaac ggcagcgcct tcttgctggc acccaataga    120
agccatgcgc cggaccacga cgtcacgcag caaagggacg aggtgtgggt ggtgggcatg    180
ggcatcgtca tgtctctcat cgtcctggcc atcgtgtttg gcaatgtgct ggtcatcaca    240
gccattgcca agttcgagcg tctgcagacg gtcaccaact acttcatcac ttcactggcc    300
tgtgctgatc tggtcatggg cctggcagtg gtgcccttgg ggccgccca tattcttatg    360 aaaatgtgga cttttggcaa cttctggtgc gagttttgga cttccattga tgtgctgtgc    420
gtcacggcca gcattgagac cctgtgcgtg atcgcagtgg atcgctactt gccattact    480 tcaccttca gtaccagag cctgctgacc aagaataagg cccgggtgat cattctgatg    540
```

```
gtgtggattg tgtcaggcct tacctccttc ttgcccattc agatgcactg gtaccgggcc    600
acccaccagg aagccatcaa ctgctatgcc gaggagacct gctgtgactt cttcacgaac    660
caagcctatg ccattgcctc ttccatcgtg tccttctacg ttcccctggt gatcatggtc    720
ttcgtctact ccagggtctt tcaggaggcc aaaaggcagc tcaacatctt cgagatgctg    780
cgcatcgacg aaggcctgcg tctcaagatt tacaaggaca ccgaaggtta ttacacgatt    840
ggcatcggcc acctcctgac aaagagccca tcactcaacg ctgccaagtc tgaactggac    900
aaagccattg tcgcaacac caacggtgtc attacaaagg acgaggcgga gaaactcttc    960
aaccaagatg tagatgcggc tgtccgtggc atcctgcgta atgccaagtt gaagcccgtg   1020
tatgactccc ttgatgctgt tcgccgtgca gccttgatca acatggtttt ccaaatgggt   1080
gagaccggag tggctggttt tacgaactcc ctgcgcatgc tccagcagaa gcgctgggac   1140
gaggccgcag tgaatttggc taaatctcgc tggtacaatc agacacctaa ccgtgccaag   1200
cgtgtcatca ctaccttccg tactggaact tgggacgctt acaagttctg cttgaaggag   1260
cacaaagccc tcaagacgtt aggcatcatc atgggcactt tcaccctctg ctggctgccc   1320
ttcttcatcg ttaacattgt gcatgtgatc caggataacc tcatccgtaa ggaagtttac   1380
atcctcctaa attggatagg ctatgtcaat tctggtttca atccccttat ctactgccgg   1440
agcccagatt tcaggattgc cttccaggag cttctgtgcc tgcgcaggtc ttctttgaag   1500
gcctatggga atggctactc cagcaacggc aacacagggg agcagagtgg a            1551

<210> SEQ ID NO 3
<211> LENGTH: 527
<212> TYPE: PRT
<213> ORGANISM: Artificial Sequence
<220> FEATURE:
<223> OTHER INFORMATION: synthetic polypeptide

<400> SEQUENCE: 3

Asp Tyr Lys Asp Asp Asp Asp Ala Gly Ala Gly Ala Leu Ala Leu Gly
 1               5                  10                  15

Ala Ser Glu Pro Cys Asn Leu Ser Ala Ala Pro Leu Pro Asp Gly
            20                  25                  30

Ala Ala Thr Ala Ala Arg Leu Leu Val Leu Ala Ser Pro Pro Ala Ser
        35                  40                  45

Leu Leu Pro Pro Ala Ser Glu Gly Ser Ala Pro Leu Ser Gln Gln Trp
    50                  55                  60

Thr Ala Gly Met Gly Leu Leu Val Ala Leu Val Leu Leu Ile Val
65                  70                  75                  80

Val Gly Asn Val Leu Val Ile Val Ala Ile Ala Lys Thr Pro Arg Leu
                85                  90                  95

Gln Thr Leu Thr Asn Leu Phe Ile Met Ser Leu Ala Ser Ala Asp Leu
            100                 105                 110

Val Met Gly Leu Leu Val Val Pro Phe Gly Ala Thr Ile Val Val Trp
        115                 120                 125

Gly Arg Trp Glu Tyr Gly Ser Phe Phe Cys Glu Leu Trp Thr Ser Val
    130                 135                 140

Asp Val Leu Cys Val Thr Ala Ser Ile Glu Thr Leu Cys Val Ile Ala
145                 150                 155                 160

Leu Asp Arg Tyr Leu Ala Ile Thr Ser Pro Phe Arg Tyr Gln Ser Leu
                165                 170                 175

Leu Thr Arg Ala Arg Ala Arg Ala Leu Val Cys Thr Val Trp Ala Ile
            180                 185                 190
```

```
Ser Ala Leu Val Ser Phe Leu Pro Ile Leu Met His Trp Trp Arg Ala
        195                 200                 205

Glu Ser Asp Glu Ala Arg Arg Cys Tyr Asn Asp Pro Lys Cys Cys Asp
        210                 215                 220

Phe Val Thr Asn Arg Ala Tyr Ala Ile Ala Ser Ser Val Val Ser Phe
225                 230                 235                 240

Tyr Val Pro Leu Cys Ile Met Ala Phe Val Tyr Leu Arg Val Phe Arg
                245                 250                 255

Glu Ala Gln Lys Gln Val Asn Ile Phe Glu Met Leu Arg Ile Asp Glu
                260                 265                 270

Gly Leu Arg Leu Lys Ile Tyr Lys Asp Thr Glu Gly Tyr Tyr Thr Ile
        275                 280                 285

Gly Ile Gly His Leu Leu Thr Lys Ser Pro Ser Leu Asn Ala Ala Lys
        290                 295                 300

Ser Glu Leu Asp Lys Ala Ile Gly Arg Asn Thr Asn Gly Val Ile Thr
305                 310                 315                 320

Lys Asp Glu Ala Glu Lys Leu Phe Asn Gln Asp Val Asp Ala Ala Val
                325                 330                 335

Arg Gly Ile Leu Arg Asn Ala Lys Leu Lys Pro Val Tyr Asp Ser Leu
                340                 345                 350

Asp Ala Val Arg Arg Ala Ala Leu Ile Asn Met Val Phe Gln Met Gly
        355                 360                 365

Glu Thr Gly Val Ala Gly Phe Thr Asn Ser Leu Arg Met Leu Gln Gln
        370                 375                 380

Lys Arg Trp Asp Glu Ala Ala Val Asn Leu Ala Lys Ser Arg Trp Tyr
385                 390                 395                 400

Asn Gln Thr Pro Asn Arg Ala Lys Arg Val Ile Thr Thr Phe Arg Thr
                405                 410                 415

Gly Thr Trp Asp Ala Tyr Leu Val Ala Leu Arg Glu Gln Lys Ala Leu
                420                 425                 430

Lys Thr Leu Gly Ile Ile Met Gly Val Phe Thr Leu Cys Trp Leu Pro
        435                 440                 445

Phe Phe Leu Ala Asn Val Val Lys Ala Phe His Arg Asp Leu Val Pro
        450                 455                 460

Asp Arg Leu Phe Val Phe Phe Asn Trp Leu Gly Tyr Ala Asn Ser Ala
465                 470                 475                 480

Phe Asn Pro Ile Ile Tyr Cys Arg Ser Pro Asp Phe Arg Lys Ala Phe
                485                 490                 495

Gln Arg Leu Leu Cys Cys Ala Arg Arg Ala Ala Cys Arg Arg Arg Ala
                500                 505                 510

Ala His Gly Asp Arg Pro Arg Ala Ser Gly Cys Leu Ala Arg Ala
        515                 520                 525

<210> SEQ ID NO 4
<211> LENGTH: 486
<212> TYPE: PRT
<213> ORGANISM: Artificial Sequence
<220> FEATURE:
<223> OTHER INFORMATION: synthetic polypeptide

<400> SEQUENCE: 4

Asp Tyr Lys Asp Asp Asp Asp Ala Met Glu Gly Ile Ser Ile Tyr Thr
1               5                   10                  15

Ser Asp Asn Tyr Thr Glu Glu Met Gly Ser Gly Asp Tyr Asp Ser Met
        20                  25                  30
```

-continued

```
Lys Glu Pro Cys Phe Arg Glu Glu Asn Ala Asn Phe Asn Lys Ile Phe
         35                  40                  45
Leu Pro Thr Ile Tyr Ser Ile Ile Phe Leu Thr Gly Ile Val Gly Asn
 50                      55                  60
Gly Leu Val Ile Leu Val Met Gly Tyr Gln Lys Lys Leu Arg Ser Met
 65                  70                  75                  80
Thr Asp Lys Tyr Arg Leu His Leu Ser Val Ala Asp Leu Leu Phe Val
                     85                  90                  95
Ile Thr Leu Pro Phe Trp Ala Val Asp Ala Val Ala Asn Trp Tyr Phe
                100                 105                 110
Gly Asn Phe Leu Cys Lys Ala Val His Val Ile Tyr Thr Val Asn Leu
                115                 120                 125
Tyr Ser Ser Val Leu Ile Leu Ala Phe Ile Ser Leu Asp Arg Tyr Leu
130                 135                 140
Ala Ile Val His Ala Thr Asn Ser Gln Arg Pro Arg Lys Leu Leu Ala
145                 150                 155                 160
Glu Lys Val Val Tyr Val Gly Val Trp Ile Pro Ala Leu Leu Leu Thr
                    165                 170                 175
Ile Pro Asp Phe Ile Phe Ala Asn Val Ser Glu Ala Asp Asp Arg Tyr
                180                 185                 190
Ile Cys Asp Arg Phe Tyr Pro Asn Asp Leu Trp Val Val Val Phe Gln
                195                 200                 205
Phe Gln His Ile Met Val Gly Leu Ile Leu Pro Gly Ile Val Ile Leu
210                 215                 220
Ser Cys Tyr Cys Ile Ile Ser Lys Leu Asn Ile Phe Glu Met Leu
225                 230                 235                 240
Arg Ile Asp Glu Gly Leu Arg Leu Lys Ile Tyr Lys Asp Thr Glu Gly
                    245                 250                 255
Tyr Tyr Thr Ile Gly Ile Gly His Leu Leu Thr Lys Ser Pro Ser Leu
                260                 265                 270
Asn Ala Ala Lys Ser Glu Leu Asp Lys Ala Ile Gly Arg Asn Thr Asn
                275                 280                 285
Gly Val Ile Thr Lys Asp Glu Ala Glu Lys Leu Phe Asn Gln Asp Val
290                 295                 300
Asp Ala Ala Val Arg Gly Ile Leu Arg Asn Ala Lys Leu Lys Pro Val
305                 310                 315                 320
Tyr Asp Ser Leu Asp Ala Val Arg Arg Ala Ala Leu Ile Asn Met Val
                    325                 330                 335
Phe Gln Met Gly Glu Thr Gly Val Ala Gly Phe Thr Asn Ser Leu Arg
                340                 345                 350
Met Leu Gln Gln Lys Arg Trp Asp Glu Ala Ala Val Asn Leu Ala Lys
                355                 360                 365
Ser Arg Trp Tyr Asn Gln Thr Pro Asn Arg Ala Lys Arg Val Ile Thr
370                 375                 380
Thr Phe Arg Thr Gly Thr Trp Asp Ala Tyr Ser His Ser Lys Gly His
385                 390                 395                 400
Gln Lys Arg Lys Ala Leu Lys Thr Thr Val Ile Leu Ile Leu Ala Phe
                    405                 410                 415
Phe Ala Cys Trp Leu Pro Tyr Tyr Ile Gly Ile Ser Ile Asp Ser Phe
                420                 425                 430
Ile Leu Leu Glu Ile Ile Lys Gln Gly Cys Glu Phe Glu Asn Thr Val
                435                 440                 445
His Lys Trp Ile Ser Ile Thr Glu Ala Leu Ala Phe Phe His Cys Cys
                450                 455                 460
```

```
Leu Asn Pro Ile Leu Tyr Ala Phe Leu Gly Ala Lys Phe Lys Thr Ser
465                 470                 475                 480

Ala Gln His Ala Leu Thr
                485

<210> SEQ ID NO 5
<211> LENGTH: 587
<212> TYPE: PRT
<213> ORGANISM: Artificial Sequence
<220> FEATURE:
<223> OTHER INFORMATION: synthetic polypeptide

<400> SEQUENCE: 5

Asp Tyr Lys Asp Asp Asp Ala Met Val Phe Leu Ser Gly Asn Ala Ser
1               5                   10                  15

Asp Ser Ser Asn Cys Thr Gln Pro Pro Ala Pro Val Asn Ile Ser Lys
                20                  25                  30

Ala Ile Leu Leu Gly Val Ile Leu Gly Gly Leu Ile Leu Phe Gly Val
            35                  40                  45

Leu Gly Asn Ile Leu Val Ile Leu Ser Val Ala Cys His Arg His Leu
50                  55                  60

His Ser Val Thr His Tyr Tyr Ile Val Asn Leu Ala Val Ala Asp Leu
65                  70                  75                  80

Leu Leu Thr Ser Thr Val Leu Pro Phe Ser Ala Ile Phe Glu Val Leu
                85                  90                  95

Gly Tyr Trp Ala Phe Gly Arg Val Phe Cys Asn Ile Trp Ala Ala Val
            100                 105                 110

Asp Val Leu Cys Cys Thr Ala Ser Ile Met Gly Leu Cys Ile Ile Ser
        115                 120                 125

Ile Asp Arg Tyr Ile Gly Val Ser Tyr Pro Leu Arg Tyr Pro Thr Ile
130                 135                 140

Val Thr Gln Arg Arg Gly Leu Met Ala Leu Leu Cys Val Trp Ala Leu
145                 150                 155                 160

Ser Leu Val Ile Ser Ile Gly Pro Leu Phe Gly Trp Arg Gln Pro Ala
                165                 170                 175

Pro Glu Asp Glu Thr Ile Cys Gln Ile Asn Glu Glu Pro Gly Tyr Val
            180                 185                 190

Leu Phe Ser Ala Leu Gly Ser Phe Tyr Leu Pro Leu Ala Ile Ile Leu
        195                 200                 205

Val Met Tyr Cys Arg Val Tyr Val Val Ala Lys Arg Glu Ser Asn Ile
210                 215                 220

Phe Glu Met Leu Arg Ile Asp Glu Gly Leu Arg Leu Lys Ile Tyr Lys
225                 230                 235                 240

Asp Thr Glu Gly Tyr Tyr Thr Ile Gly Ile Gly His Leu Leu Thr Lys
                245                 250                 255

Ser Pro Ser Leu Asn Ala Ala Lys Ser Glu Leu Asp Lys Ala Ile Gly
            260                 265                 270

Arg Asn Thr Asn Gly Val Ile Thr Lys Asp Glu Ala Glu Lys Leu Phe
        275                 280                 285

Asn Gln Asp Val Asp Ala Ala Val Arg Gly Ile Leu Arg Asn Ala Lys
    290                 295                 300

Leu Lys Pro Val Tyr Asp Ser Leu Asp Ala Val Arg Arg Ala Ala Leu
305                 310                 315                 320

Ile Asn Met Val Phe Gln Met Gly Glu Thr Gly Val Ala Gly Phe Thr
                325                 330                 335
```

-continued

```
Asn Ser Leu Arg Met Leu Gln Gln Lys Arg Trp Asp Glu Ala Ala Val
            340                 345                 350
Asn Leu Ala Lys Ser Arg Trp Tyr Asn Gln Thr Pro Asn Arg Ala Lys
        355                 360                 365
Arg Val Ile Thr Thr Phe Arg Thr Gly Thr Trp Asp Ala Tyr Leu Lys
    370                 375                 380
Phe Ser Arg Glu Lys Lys Ala Ala Lys Thr Leu Gly Ile Val Val Gly
385                 390                 395                 400
Cys Phe Val Leu Cys Trp Leu Pro Phe Phe Leu Val Met Pro Ile Gly
                405                 410                 415
Ser Phe Phe Pro Asp Phe Lys Pro Ser Glu Thr Val Phe Lys Ile Val
            420                 425                 430
Phe Trp Leu Gly Tyr Leu Asn Ser Cys Ile Asn Pro Ile Ile Tyr Pro
        435                 440                 445
Cys Ser Ser Gln Glu Phe Lys Lys Ala Phe Gln Asn Val Leu Arg Ile
    450                 455                 460
Gln Cys Leu Cys Arg Lys Gln Ser Ser Lys His Ala Leu Gly Tyr Thr
465                 470                 475                 480
Leu His Pro Pro Ser Gln Ala Val Glu Gly Gln His Lys Asp Met Val
                485                 490                 495
Arg Ile Pro Val Gly Ser Arg Glu Thr Phe Tyr Arg Ile Ser Lys Thr
            500                 505                 510
Asp Gly Val Cys Glu Trp Lys Phe Phe Ser Ser Met Pro Arg Gly Ser
        515                 520                 525
Ala Arg Ile Thr Val Ser Lys Asp Gln Ser Ser Cys Thr Thr Ala Arg
    530                 535                 540
Val Arg Ser Lys Ser Phe Leu Gln Val Cys Cys Cys Val Gly Pro Ser
545                 550                 555                 560
Thr Pro Ser Leu Asp Lys Asn His Gln Val Pro Thr Ile Lys Val His
                565                 570                 575
Thr Ile Ser Leu Ser Glu Asn Gly Glu Val
            580                 585

<210> SEQ ID NO 6
<211> LENGTH: 481
<212> TYPE: PRT
<213> ORGANISM: Artificial Sequence
<220> FEATURE:
<223> OTHER INFORMATION: synthetic polypeptide

<400> SEQUENCE: 6

Asp Tyr Lys Asp Asp Asp Ala Met Gly Ser Leu Gln Pro Asp Ala Gly
1               5                   10                  15
Asn Ala Ser Trp Asn Gly Thr Glu Ala Pro Gly Gly Gly Ala Arg Ala
            20                  25                  30
Thr Pro Tyr Ser Leu Gln Val Thr Leu Thr Leu Val Cys Leu Ala Gly
        35                  40                  45
Leu Leu Met Leu Leu Thr Val Phe Gly Asn Val Leu Ile Ile Ala
    50                  55                  60
Val Phe Thr Ser Arg Ala Leu Lys Ala Pro Gln Asn Leu Phe Leu Val
65                  70                  75                  80
Ser Leu Ala Ser Ala Asp Ile Leu Val Ala Thr Leu Val Ile Pro Phe
                85                  90                  95
Ser Leu Ala Asn Glu Val Met Gly Tyr Trp Tyr Phe Gly Lys Ala Trp
            100                 105                 110
Cys Glu Ile Tyr Leu Ala Leu Asp Val Leu Phe Cys Thr Ser Ser Ile
```

```
            115                 120                 125
Val His Leu Cys Ala Ile Ser Leu Asp Arg Tyr Trp Ser Ile Thr Gln
130                 135                 140

Ala Ile Glu Tyr Asn Leu Lys Arg Thr Pro Arg Ile Lys Ala Ile
145                 150                 155                 160

Ile Ile Thr Val Trp Val Ile Ser Ala Val Ile Ser Phe Pro Pro Leu
                165                 170                 175

Ile Ser Ile Glu Lys Lys Gly Gly Gly Gly Pro Gln Pro Ala Glu
            180                 185                 190

Pro Arg Cys Glu Ile Asn Asp Gln Lys Trp Tyr Val Ile Ser Ser Cys
                195                 200                 205

Ile Gly Ser Phe Phe Ala Pro Cys Leu Ile Met Ile Leu Val Tyr Val
            210                 215                 220

Arg Ile Tyr Gln Ile Ala Lys Arg Arg Thr Asn Ile Phe Glu Met Leu
225                 230                 235                 240

Arg Ile Asp Glu Gly Leu Arg Leu Lys Ile Tyr Lys Asp Thr Glu Gly
                245                 250                 255

Tyr Tyr Thr Ile Gly Ile Gly His Leu Leu Thr Lys Ser Pro Ser Leu
            260                 265                 270

Asn Ala Ala Lys Ser Glu Leu Asp Lys Ala Ile Gly Arg Asn Thr Asn
                275                 280                 285

Gly Val Ile Thr Lys Asp Glu Ala Glu Lys Leu Phe Asn Gln Asp Val
            290                 295                 300

Asp Ala Ala Val Arg Gly Ile Leu Arg Asn Ala Lys Leu Lys Pro Val
305                 310                 315                 320

Tyr Asp Ser Leu Asp Ala Val Arg Arg Ala Ala Leu Ile Asn Met Val
                325                 330                 335

Phe Gln Met Gly Glu Thr Gly Val Ala Gly Phe Thr Asn Ser Leu Arg
            340                 345                 350

Met Leu Gln Gln Lys Arg Trp Asp Glu Ala Ala Val Asn Leu Ala Lys
                355                 360                 365

Ser Arg Trp Tyr Asn Gln Thr Pro Asn Arg Ala Lys Arg Val Ile Thr
370                 375                 380

Thr Phe Arg Thr Gly Thr Trp Asp Ala Tyr Gly Arg Gln Asn Arg Glu
385                 390                 395                 400

Lys Arg Phe Thr Phe Val Leu Ala Val Val Ile Gly Val Phe Val Val
                405                 410                 415

Cys Trp Phe Pro Phe Phe Phe Thr Tyr Thr Leu Thr Ala Val Gly Cys
                420                 425                 430

Ser Val Pro Arg Thr Leu Phe Lys Phe Phe Phe Trp Phe Gly Tyr Cys
            435                 440                 445

Asn Ser Ser Leu Asn Pro Val Ile Tyr Thr Ile Phe Asn His Asp Phe
450                 455                 460

Arg Arg Ala Phe Lys Lys Ile Leu Cys Arg Gly Asp Arg Lys Arg Ile
465                 470                 475                 480

Val
```

<210> SEQ ID NO 7
<211> LENGTH: 577
<212> TYPE: PRT
<213> ORGANISM: Artificial Sequence
<220> FEATURE:
<223> OTHER INFORMATION: synthetic polypeptide

<400> SEQUENCE: 7

-continued

```
Asp Tyr Lys Asp Asp Asp Ala Met Arg Thr Leu Asn Thr Ser Ala Met
  1               5                  10                  15

Asp Gly Thr Gly Leu Val Val Glu Arg Asp Phe Ser Val Arg Ile Leu
             20                  25                  30

Thr Ala Cys Phe Leu Ser Leu Leu Ile Leu Ser Thr Leu Leu Gly Asn
         35                  40                  45

Thr Leu Val Cys Ala Ala Val Ile Arg Phe Arg His Leu Arg Ser Lys
     50                  55                  60

Val Thr Asn Phe Phe Val Ile Ser Leu Ala Val Ser Asp Leu Leu Val
 65                  70                  75                  80

Ala Val Leu Val Met Pro Trp Lys Ala Val Ala Glu Ile Ala Gly Phe
                 85                  90                  95

Trp Pro Phe Gly Ser Phe Cys Asn Ile Trp Val Ala Phe Asp Ile Met
            100                 105                 110

Cys Ser Thr Ala Ser Ile Leu Asn Leu Cys Val Ile Ser Val Asp Arg
            115                 120                 125

Tyr Trp Ala Ile Ser Ser Pro Phe Arg Tyr Glu Arg Lys Met Thr Pro
        130                 135                 140

Lys Ala Ala Phe Ile Leu Ile Ser Val Ala Trp Thr Leu Ser Val Leu
145                 150                 155                 160

Ile Ser Phe Ile Pro Val Gln Leu Ser Trp His Lys Ala Lys Pro Thr
                165                 170                 175

Ser Pro Ser Asp Gly Asn Ala Thr Ser Leu Ala Glu Thr Ile Asp Asn
            180                 185                 190

Cys Asp Ser Ser Leu Ser Arg Thr Tyr Ala Ile Ser Ser Ser Val Ile
        195                 200                 205

Ser Phe Tyr Ile Pro Val Ala Ile Met Ile Val Thr Tyr Thr Arg Ile
    210                 215                 220

Tyr Arg Ile Ala Gln Lys Gln Ile Asn Ile Phe Glu Met Leu Arg Ile
225                 230                 235                 240

Asp Glu Gly Leu Arg Leu Lys Ile Tyr Lys Asp Thr Glu Gly Tyr Tyr
                245                 250                 255

Thr Ile Gly Ile Gly His Leu Leu Thr Lys Ser Pro Ser Leu Asn Ala
            260                 265                 270

Ala Lys Ser Glu Leu Asp Lys Ala Ile Gly Arg Asn Thr Asn Gly Val
        275                 280                 285

Ile Thr Lys Asp Glu Ala Glu Lys Leu Phe Asn Gln Asp Val Asp Ala
    290                 295                 300

Ala Val Arg Gly Ile Leu Arg Asn Ala Lys Leu Lys Pro Val Tyr Asp
305                 310                 315                 320

Ser Leu Asp Ala Val Arg Arg Ala Ala Leu Ile Asn Met Val Phe Gln
                325                 330                 335

Met Gly Glu Thr Gly Val Ala Gly Phe Thr Asn Ser Leu Arg Met Leu
            340                 345                 350

Gln Gln Lys Arg Trp Asp Glu Ala Ala Val Asn Leu Ala Lys Ser Arg
        355                 360                 365

Trp Tyr Asn Gln Thr Pro Asn Arg Ala Lys Arg Val Ile Thr Thr Phe
    370                 375                 380

Arg Thr Gly Thr Trp Asp Ala Tyr Met Ser Phe Lys Arg Glu Thr Lys
385                 390                 395                 400

Val Leu Lys Thr Leu Ser Val Ile Met Gly Val Phe Val Cys Cys Trp
                405                 410                 415

Leu Pro Phe Phe Ile Leu Asn Cys Ile Leu Pro Phe Cys Gly Ser Gly
            420                 425                 430
```

Glu Thr Gln Pro Phe Cys Ile Asp Ser Asn Thr Phe Asp Val Phe Val
        435                 440                 445

Trp Phe Gly Trp Ala Asn Ser Ser Leu Asn Pro Ile Ile Tyr Ala Phe
    450                 455                 460

Asn Ala Asp Phe Arg Lys Ala Phe Ser Thr Leu Leu Gly Cys Tyr Arg
465                 470                 475                 480

Leu Cys Pro Ala Thr Asn Asn Ala Ile Glu Thr Val Ser Ile Asn Asn
                485                 490                 495

Asn Gly Ala Ala Met Phe Ser Ser His His Glu Pro Arg Gly Ser Ile
            500                 505                 510

Ser Lys Glu Cys Asn Leu Val Tyr Leu Ile Pro His Ala Val Gly Ser
        515                 520                 525

Ser Glu Asp Leu Lys Lys Glu Ala Ala Gly Ile Ala Arg Pro Leu
    530                 535                 540

Glu Lys Leu Ser Pro Ala Leu Ser Val Ile Leu Asp Tyr Asp Thr Asp
545                 550                 555                 560

Val Ser Leu Glu Lys Ile Gln Pro Ile Thr Gln Asn Gly Gln His Pro
                565                 570                 575

Thr

<210> SEQ ID NO 8
<211> LENGTH: 468
<212> TYPE: PRT
<213> ORGANISM: Artificial Sequence
<220> FEATURE:
<223> OTHER INFORMATION: synthetic polypeptide

<400> SEQUENCE: 8

Asp Tyr Lys Asp Asp Ala Met Asp Pro Leu Asn Leu Ser Trp Tyr
1               5                   10                  15

Asp Asp Asp Leu Glu Arg Gln Asn Trp Ser Arg Pro Phe Asn Gly Ser
                20                  25                  30

Asp Gly Lys Ala Asp Arg Pro His Tyr Asn Tyr Tyr Ala Thr Leu Leu
            35                  40                  45

Thr Leu Leu Ile Ala Val Ile Val Phe Gly Asn Val Leu Val Cys Met
    50                  55                  60

Ala Val Ser Arg Glu Lys Ala Leu Gln Thr Thr Thr Asn Tyr Leu Ile
65                  70                  75                  80

Val Ser Leu Ala Val Ala Asp Leu Leu Val Ala Thr Leu Val Met Pro
                85                  90                  95

Trp Val Val Tyr Leu Glu Val Val Gly Glu Trp Lys Phe Ser Arg Ile
                100                 105                 110

His Cys Asp Ile Phe Val Thr Leu Asp Val Met Met Cys Thr Ala Ser
            115                 120                 125

Ile Leu Asn Leu Cys Ala Ile Ser Ile Asp Arg Tyr Thr Ala Val Ala
        130                 135                 140

Met Pro Met Leu Tyr Asn Thr Arg Tyr Ser Ser Lys Arg Arg Val Thr
145                 150                 155                 160

Val Met Ile Ser Ile Val Trp Val Leu Ser Phe Thr Ile Ser Cys Pro
                165                 170                 175

Leu Leu Phe Gly Leu Asn Ala Asp Gln Asn Glu Cys Ile Ile Ala
            180                 185                 190

Asn Pro Ala Phe Val Val Tyr Ser Ser Ile Val Ser Phe Tyr Val Pro
        195                 200                 205

Phe Ile Val Thr Leu Leu Val Tyr Ile Lys Ile Tyr Ile Val Leu Arg

-continued

Arg Arg Arg Asn Ile Phe Glu Met Leu Arg Ile Asp Glu Gly Leu Arg
225                 230                 235                 240

Leu Lys Ile Tyr Lys Asp Thr Glu Gly Tyr Tyr Thr Ile Gly Ile Gly
                245                 250                 255

His Leu Leu Thr Lys Ser Pro Ser Leu Asn Ala Ala Lys Ser Glu Leu
            260                 265                 270

Asp Lys Ala Ile Gly Arg Asn Thr Asn Gly Val Ile Thr Lys Asp Glu
        275                 280                 285

Ala Glu Lys Leu Phe Asn Gln Asp Val Asp Ala Ala Val Arg Gly Ile
    290                 295                 300

Leu Arg Asn Ala Lys Leu Lys Pro Val Tyr Asp Ser Leu Asp Ala Val
305                 310                 315                 320

Arg Arg Ala Ala Leu Ile Asn Met Val Phe Gln Met Gly Glu Thr Gly
                325                 330                 335

Val Ala Gly Phe Thr Asn Ser Leu Arg Met Leu Gln Gln Lys Arg Trp
                340                 345                 350

Asp Glu Ala Ala Val Asn Leu Ala Lys Ser Arg Trp Tyr Asn Gln Thr
            355                 360                 365

Pro Asn Arg Ala Lys Arg Val Ile Thr Thr Phe Arg Thr Gly Thr Trp
        370                 375                 380

Asp Ala Tyr Leu Ser Gln Gln Lys Glu Lys Lys Ala Thr Gln Met Leu
385                 390                 395                 400

Ala Ile Val Leu Gly Val Phe Ile Ile Cys Trp Leu Pro Phe Phe Ile
                405                 410                 415

Thr His Ile Leu Asn Ile His Cys Asp Cys Asn Ile Pro Pro Val Leu
                420                 425                 430

Tyr Ser Ala Phe Thr Trp Leu Gly Tyr Val Asn Ser Ala Val Asn Pro
            435                 440                 445

Ile Ile Tyr Thr Thr Phe Asn Ile Glu Phe Arg Lys Ala Phe Leu Lys
        450                 455                 460

Ile Leu His Cys
465

<210> SEQ ID NO 9
<211> LENGTH: 539
<212> TYPE: PRT
<213> ORGANISM: Artificial Sequence
<220> FEATURE:
<223> OTHER INFORMATION: synthetic polypeptide

<400> SEQUENCE: 9

Asp Tyr Lys Asp Asp Asp Ala Met Thr Leu His Asn Asn Ser Thr Thr
1               5                   10                  15

Ser Pro Leu Phe Pro Asn Ile Ser Ser Ser Trp Ile His Ser Pro Ser
                20                  25                  30

Asp Ala Gly Leu Pro Pro Gly Thr Val Thr His Phe Gly Ser Tyr Asn
            35                  40                  45

Val Ser Arg Ala Ala Gly Asn Phe Ser Ser Pro Asp Gly Thr Thr Asp
        50                  55                  60

Asp Pro Leu Gly Gly His Thr Val Trp Gln Val Val Phe Ile Ala Phe
65                  70                  75                  80

Leu Thr Gly Ile Leu Ala Leu Val Thr Ile Ile Gly Asn Ile Leu Val
                85                  90                  95

Ile Val Ser Phe Lys Val Asn Lys Gln Leu Lys Thr Val Asn Asn Tyr
                100                 105                 110

-continued

```
Phe Leu Leu Ser Leu Ala Cys Ala Asp Leu Ile Ile Gly Val Ile Ser
            115                 120                 125
Met Asn Leu Phe Thr Thr Tyr Ile Ile Met Asn Arg Trp Ala Leu Gly
    130                 135                 140
Asn Leu Ala Cys Asp Leu Trp Leu Ala Ile Asp Tyr Val Ala Ser Asn
145                 150                 155                 160
Ala Ser Val Met Asn Leu Leu Val Ile Ser Phe Asp Arg Tyr Phe Ser
                165                 170                 175
Ile Thr Arg Pro Leu Thr Tyr Arg Ala Lys Arg Thr Thr Lys Arg Ala
            180                 185                 190
Gly Val Met Ile Gly Leu Ala Trp Val Ile Ser Phe Val Leu Trp Ala
        195                 200                 205
Pro Ala Ile Leu Phe Trp Gln Tyr Phe Val Gly Lys Arg Thr Val Pro
    210                 215                 220
Pro Gly Glu Cys Phe Ile Gln Phe Leu Ser Glu Pro Thr Ile Thr Phe
225                 230                 235                 240
Gly Thr Ala Ile Ala Ala Phe Tyr Met Pro Val Thr Ile Met Thr Ile
                245                 250                 255
Leu Tyr Trp Arg Ile Tyr Lys Glu Thr Glu Lys Arg Thr Asn Ile Phe
            260                 265                 270
Glu Met Leu Arg Ile Asp Glu Gly Leu Arg Leu Lys Ile Tyr Lys Asp
        275                 280                 285
Thr Glu Gly Tyr Tyr Thr Ile Gly Ile Gly His Leu Leu Thr Lys Ser
    290                 295                 300
Pro Ser Leu Asn Ala Ala Lys Ser Glu Leu Asp Lys Ala Ile Gly Arg
305                 310                 315                 320
Asn Thr Asn Gly Val Ile Thr Lys Asp Glu Ala Glu Lys Leu Phe Asn
                325                 330                 335
Gln Asp Val Asp Ala Ala Val Arg Gly Ile Leu Arg Asn Ala Lys Leu
            340                 345                 350
Lys Pro Val Tyr Asp Ser Leu Asp Ala Val Arg Arg Ala Ala Leu Ile
        355                 360                 365
Asn Met Val Phe Gln Met Gly Glu Thr Gly Val Ala Gly Phe Thr Asn
    370                 375                 380
Ser Leu Arg Met Leu Gln Gln Lys Arg Trp Asp Glu Ala Ala Val Asn
385                 390                 395                 400
Leu Ala Lys Ser Arg Trp Tyr Asn Gln Thr Pro Asn Arg Ala Lys Arg
                405                 410                 415
Val Ile Thr Thr Phe Arg Thr Gly Thr Trp Asp Ala Tyr Met Ser Leu
            420                 425                 430
Val Lys Glu Lys Lys Ala Ala Gln Thr Leu Ser Ala Ile Leu Leu Ala
        435                 440                 445
Phe Ile Ile Thr Trp Thr Pro Tyr Asn Ile Met Val Leu Val Asn Thr
    450                 455                 460
Phe Cys Asp Ser Cys Ile Pro Lys Thr Phe Trp Asn Leu Gly Tyr Trp
465                 470                 475                 480
Leu Cys Tyr Ile Asn Ser Thr Val Asn Pro Val Cys Tyr Ala Leu Cys
                485                 490                 495
Asn Lys Thr Phe Arg Thr Thr Phe Lys Met Leu Leu Leu Cys Gln Cys
            500                 505                 510
Asp Lys Lys Lys Arg Arg Lys Gln Gln Tyr Gln Gln Arg Gln Ser Val
        515                 520                 525
Ile Phe His Lys Arg Ala Pro Glu Gln Ala Leu
```

```
                                    530                535

<210> SEQ ID NO 10
<211> LENGTH: 481
<212> TYPE: PRT
<213> ORGANISM: Artificial Sequence
<220> FEATURE:
<223> OTHER INFORMATION: synthetic polypeptide

<400> SEQUENCE: 10

Asp Tyr Lys Asp Asp Ala Met Pro Pro Ser Ile Ser Ala Phe Gln
 1               5                  10                  15

Ala Ala Tyr Ile Gly Ile Glu Val Leu Ile Ala Leu Val Ser Val Pro
                20                  25                  30

Gly Asn Val Leu Val Ile Trp Ala Val Lys Val Asn Gln Ala Leu Arg
                35                  40                  45

Asp Ala Thr Phe Cys Phe Ile Val Ser Leu Ala Val Ala Asp Val Ala
            50                  55                  60

Val Gly Ala Leu Val Ile Pro Leu Ala Ile Leu Ile Asn Ile Gly Pro
 65                  70                  75                  80

Gln Thr Tyr Phe His Thr Cys Leu Met Val Ala Cys Pro Val Leu Ile
                85                  90                  95

Leu Thr Gln Ser Ser Ile Leu Ala Leu Leu Ala Ile Ala Val Asp Arg
                100                 105                 110

Tyr Leu Arg Val Lys Ile Pro Leu Arg Tyr Lys Met Val Val Thr Pro
                115                 120                 125

Arg Arg Ala Ala Val Ala Ile Ala Gly Cys Trp Ile Leu Ser Phe Val
                130                 135                 140

Val Gly Leu Thr Pro Met Phe Gly Trp Asn Asn Leu Ser Ala Val Glu
145                 150                 155                 160

Arg Ala Trp Ala Ala Asn Gly Ser Met Gly Glu Pro Val Ile Lys Cys
                165                 170                 175

Glu Phe Glu Lys Val Ile Ser Met Glu Tyr Met Val Tyr Phe Asn Phe
                180                 185                 190

Phe Val Trp Val Leu Pro Pro Leu Leu Leu Met Val Leu Ile Tyr Leu
            195                 200                 205

Glu Val Phe Tyr Leu Ile Arg Lys Gln Leu Asn Ile Phe Glu Met Leu
    210                 215                 220

Arg Ile Asp Glu Gly Leu Arg Leu Lys Ile Tyr Lys Asp Thr Glu Gly
225                 230                 235                 240

Tyr Tyr Thr Ile Gly Ile Gly His Leu Leu Thr Lys Ser Pro Ser Leu
                245                 250                 255

Asn Ala Ala Lys Ser Glu Leu Asp Lys Ala Ile Gly Arg Asn Thr Asn
                260                 265                 270

Gly Val Ile Thr Lys Asp Glu Ala Glu Lys Leu Phe Asn Gln Asp Val
                275                 280                 285

Asp Ala Ala Val Arg Gly Ile Leu Arg Asn Ala Lys Leu Lys Pro Val
            290                 295                 300

Tyr Asp Ser Leu Asp Ala Val Arg Arg Ala Ala Leu Ile Asn Met Val
305                 310                 315                 320

Phe Gln Met Gly Glu Thr Gly Val Ala Gly Phe Thr Asn Ser Leu Arg
                325                 330                 335

Met Leu Gln Gln Lys Arg Trp Asp Glu Ala Ala Val Asn Leu Ala Lys
                340                 345                 350

Ser Arg Trp Tyr Asn Gln Thr Pro Asn Arg Ala Lys Arg Val Ile Thr
                355                 360                 365
```

Thr Phe Arg Thr Gly Thr Trp Asp Ala Tyr Lys Tyr Tyr Gly Lys Glu
    370                 375                 380

Leu Lys Ile Ala Lys Ser Leu Ala Leu Ile Leu Phe Leu Phe Ala Leu
385                 390                 395                 400

Ser Trp Leu Pro Leu His Ile Leu Asn Cys Ile Thr Leu Phe Cys Pro
                405                 410                 415

Ser Cys His Lys Pro Ser Ile Leu Thr Tyr Ile Ala Ile Phe Leu Thr
            420                 425                 430

His Gly Asn Ser Ala Met Asn Pro Ile Val Tyr Ala Phe Arg Ile Gln
        435                 440                 445

Lys Phe Arg Val Thr Phe Leu Lys Ile Trp Asn Asp His Phe Arg Cys
450                 455                 460

Gln Pro Ala Pro Pro Ile Asp Glu Asp Leu Pro Glu Glu Arg Pro Asp
465                 470                 475                 480

Asp

<210> SEQ ID NO 11
<211> LENGTH: 471
<212> TYPE: PRT
<213> ORGANISM: Artificial Sequence
<220> FEATURE:
<223> OTHER INFORMATION: synthetic polypeptide

<400> SEQUENCE: 11

Tyr Tyr Lys Asp Asp Ala Met Ser Leu Pro Asn Ser Ser Cys Leu
  1               5                  10                  15

Leu Glu Asp Lys Met Cys Glu Gly Asn Lys Thr Thr Met Ala Ser Pro
                 20                  25                  30

Gln Leu Met Pro Leu Val Val Leu Ser Thr Ile Cys Leu Val Thr
             35                  40                  45

Val Gly Leu Asn Leu Leu Val Leu Tyr Ala Val Arg Ser Glu Arg Lys
 50                  55                  60

Leu His Thr Val Gly Asn Leu Tyr Ile Val Ser Leu Ser Val Ala Asp
 65                  70                  75                  80

Leu Ile Val Gly Ala Val Val Met Pro Met Asn Ile Leu Tyr Leu Leu
                 85                  90                  95

Met Ser Lys Trp Ser Leu Gly Arg Pro Leu Cys Leu Phe Trp Leu Ser
            100                 105                 110

Met Asp Tyr Val Ala Ser Thr Ala Ser Ile Phe Ser Val Phe Ile Leu
        115                 120                 125

Cys Ile Asp Arg Tyr Arg Ser Val Gln Gln Pro Leu Arg Tyr Leu Lys
    130                 135                 140

Tyr Arg Thr Lys Thr Arg Ala Ser Ala Thr Ile Leu Gly Ala Trp Phe
145                 150                 155                 160

Leu Ser Phe Leu Trp Val Ile Pro Ile Leu Gly Trp Asn His Phe Met
                165                 170                 175

Gln Gln Thr Ser Val Arg Arg Glu Asp Lys Cys Glu Thr Asp Phe Tyr
            180                 185                 190

Asp Val Thr Trp Phe Lys Val Met Thr Ala Ile Ile Asn Phe Tyr Leu
        195                 200                 205

Pro Thr Leu Leu Met Leu Trp Phe Tyr Ala Lys Ile Tyr Lys Ala Val
    210                 215                 220

Arg Gln His Cys Asn Ile Phe Glu Met Leu Arg Ile Asp Glu Gly Leu
225                 230                 235                 240

Arg Leu Lys Ile Tyr Lys Asp Thr Glu Gly Tyr Tyr Thr Ile Gly Ile

```
                      245                 250                 255
Gly His Leu Leu Thr Lys Ser Pro Ser Leu Asn Ala Ala Lys Ser Glu
                260                 265                 270

Leu Asp Lys Ala Ile Gly Arg Asn Thr Asn Gly Val Ile Thr Lys Asp
            275                 280                 285

Glu Ala Glu Lys Leu Phe Asn Gln Asp Val Asp Ala Ala Val Arg Gly
        290                 295                 300

Ile Leu Arg Asn Ala Lys Leu Lys Pro Val Tyr Asp Ser Leu Asp Ala
305                 310                 315                 320

Val Arg Arg Ala Ala Leu Ile Asn Met Val Phe Gln Met Gly Glu Thr
                325                 330                 335

Gly Val Ala Gly Phe Thr Asn Ser Leu Arg Met Leu Gln Gln Lys Arg
                340                 345                 350

Trp Asp Glu Ala Ala Val Asn Leu Ala Lys Ser Arg Trp Tyr Asn Gln
            355                 360                 365

Thr Pro Asn Arg Ala Lys Arg Val Ile Thr Thr Phe Arg Thr Gly Thr
        370                 375                 380

Trp Asp Ala Tyr Leu His Met Asn Arg Glu Arg Lys Ala Ala Lys Gln
385                 390                 395                 400

Leu Gly Phe Ile Met Ala Ala Phe Ile Leu Cys Trp Ile Pro Tyr Phe
                405                 410                 415

Ile Phe Phe Met Val Ile Ala Phe Cys Lys Asn Cys Cys Asn Glu His
                420                 425                 430

Leu His Met Phe Thr Ile Trp Leu Gly Tyr Ile Asn Ser Thr Leu Asn
            435                 440                 445

Pro Leu Ile Tyr Pro Leu Cys Asn Glu Asn Phe Lys Lys Thr Phe Lys
        450                 455                 460

Arg Ile Leu His Ile Arg Ser
465                 470

<210> SEQ ID NO 12
<211> LENGTH: 516
<212> TYPE: PRT
<213> ORGANISM: Artificial Sequence
<220> FEATURE:
<223> OTHER INFORMATION: synthetic polypeptide

<400> SEQUENCE: 12

Asp Tyr Lys Asp Asp Ala Met Ala Pro Asn Gly Thr Ala Ser Ser
 1               5                  10                  15

Phe Cys Leu Asp Ser Thr Ala Cys Lys Ile Thr Ile Thr Val Val Leu
                20                  25                  30

Ala Val Leu Ile Leu Ile Thr Val Ala Gly Asn Val Val Val Cys Leu
            35                  40                  45

Ala Val Gly Leu Asn Arg Arg Leu Arg Asn Leu Thr Asn Cys Phe Ile
        50                  55                  60

Val Ser Leu Ala Ile Thr Asp Leu Leu Leu Gly Leu Leu Val Leu Pro
65                  70                  75                  80

Phe Ser Ala Ile Tyr Gln Leu Ser Cys Lys Trp Ser Phe Gly Lys Val
                85                  90                  95

Phe Cys Asn Ile Tyr Thr Ser Leu Asp Val Met Leu Cys Thr Ala Ser
            100                 105                 110

Ile Leu Asn Leu Phe Met Ile Ser Leu Asp Arg Tyr Cys Ala Val Met
        115                 120                 125

Asp Pro Leu Arg Tyr Pro Val Leu Val Thr Pro Val Arg Val Ala Ile
    130                 135                 140
```

Ser Leu Val Leu Ile Trp Val Ile Ser Ile Thr Leu Ser Phe Leu Ser
145                 150                 155                 160

Ile His Leu Gly Trp Asn Ser Arg Asn Glu Thr Ser Lys Gly Asn His
            165                 170                 175

Thr Thr Ser Lys Cys Lys Val Gln Val Asn Glu Val Tyr Gly Leu Val
        180                 185                 190

Asp Gly Leu Val Thr Phe Tyr Leu Pro Leu Leu Ile Met Cys Ile Thr
    195                 200                 205

Tyr Tyr Arg Ile Phe Lys Val Ala Arg Asp Gln Ala Asn Ile Phe Glu
210                 215                 220

Met Leu Arg Ile Asp Glu Gly Leu Arg Leu Lys Ile Tyr Lys Asp Thr
225                 230                 235                 240

Glu Gly Tyr Tyr Thr Ile Gly Ile Gly His Leu Leu Thr Lys Ser Pro
                245                 250                 255

Ser Leu Asn Ala Ala Lys Ser Glu Leu Asp Lys Ala Ile Gly Arg Asn
            260                 265                 270

Thr Asn Gly Val Ile Thr Lys Asp Glu Ala Glu Lys Leu Phe Asn Gln
        275                 280                 285

Asp Val Asp Ala Ala Val Arg Gly Ile Leu Arg Asn Ala Lys Leu Lys
    290                 295                 300

Pro Val Tyr Asp Ser Leu Asp Ala Val Arg Arg Ala Ala Leu Ile Asn
305                 310                 315                 320

Met Val Phe Gln Met Gly Glu Thr Gly Val Ala Gly Phe Thr Asn Ser
                325                 330                 335

Leu Arg Met Leu Gln Gln Lys Arg Trp Asp Glu Ala Ala Val Asn Leu
            340                 345                 350

Ala Lys Ser Arg Trp Tyr Asn Gln Thr Pro Asn Arg Ala Lys Arg Val
        355                 360                 365

Ile Thr Thr Phe Arg Thr Gly Thr Trp Asp Ala Tyr Ala Ala Thr Ile
    370                 375                 380

Arg Glu His Lys Ala Thr Val Thr Leu Ala Ala Val Met Gly Ala Phe
385                 390                 395                 400

Ile Ile Cys Trp Phe Pro Tyr Phe Thr Ala Phe Val Tyr Arg Gly Leu
                405                 410                 415

Arg Gly Asp Asp Ala Ile Asn Glu Val Leu Glu Ala Ile Val Leu Trp
            420                 425                 430

Leu Gly Tyr Ala Asn Ser Ala Leu Asn Pro Ile Leu Tyr Ala Ala Leu
        435                 440                 445

Asn Arg Asp Phe Arg Thr Gly Tyr Gln Gln Leu Phe Cys Cys Arg Leu
    450                 455                 460

Ala Asn Arg Asn Ser His Lys Thr Ser Leu Arg Ser Asn Ala Ser Gln
465                 470                 475                 480

Leu Ser Arg Thr Gln Ser Arg Glu Pro Arg Gln Gln Glu Glu Lys Pro
                485                 490                 495

Leu Lys Leu Gln Val Trp Ser Gly Thr Glu Val Thr Ala Pro Gln Gly
            500                 505                 510

Ala Thr Asp Arg
        515

<210> SEQ ID NO 13
<211> LENGTH: 481
<212> TYPE: PRT
<213> ORGANISM: Artificial Sequence
<220> FEATURE:
<223> OTHER INFORMATION: synthetic polypeptide

<400> SEQUENCE: 13

```
Asp Tyr Lys Asp Asp Ala Met Asp Val Leu Ser Pro Gly Gln Gly
 1               5                  10                  15

Asn Asn Thr Thr Ser Pro Pro Ala Pro Phe Glu Thr Gly Gly Asn Thr
            20                  25                  30

Thr Gly Ile Ser Asp Val Thr Val Ser Tyr Gln Val Ile Thr Ser Leu
        35                  40                  45

Leu Leu Gly Thr Leu Ile Phe Cys Ala Val Leu Gly Asn Ala Cys Val
    50                  55                  60

Val Ala Ala Ile Ala Leu Glu Arg Ser Leu Gln Asn Val Ala Asn Tyr
65                  70                  75                  80

Leu Ile Gly Ser Leu Ala Val Thr Asp Leu Met Val Ser Val Leu Val
                85                  90                  95

Leu Pro Met Ala Ala Leu Tyr Gln Val Leu Asn Lys Trp Thr Leu Gly
                100                 105                 110

Gln Val Thr Cys Asp Leu Phe Ile Ala Leu Asp Val Leu Cys Cys Thr
            115                 120                 125

Ser Ser Ile Leu His Leu Cys Ala Ile Ala Leu Asp Arg Tyr Trp Ala
130                 135                 140

Ile Thr Asp Pro Ile Asp Tyr Val Asn Lys Arg Thr Pro Arg Arg Ala
145                 150                 155                 160

Ala Ala Leu Ile Ser Leu Thr Trp Leu Ile Gly Phe Leu Ile Ser Ile
                165                 170                 175

Pro Pro Met Leu Gly Trp Arg Thr Pro Glu Asp Arg Ser Asp Pro Asp
                180                 185                 190

Ala Cys Thr Ile Ser Lys Asp His Gly Tyr Thr Ile Tyr Ser Thr Phe
            195                 200                 205

Gly Ala Phe Tyr Ile Pro Leu Leu Leu Met Leu Val Leu Tyr Gly Arg
        210                 215                 220

Ile Phe Arg Ala Ala Arg Phe Arg Ile Asn Ile Phe Glu Met Leu Arg
225                 230                 235                 240

Ile Asp Glu Gly Leu Arg Leu Lys Ile Tyr Lys Asp Thr Glu Gly Tyr
                245                 250                 255

Tyr Thr Ile Gly Ile Gly His Leu Leu Thr Lys Ser Pro Ser Leu Asn
            260                 265                 270

Ala Ala Lys Ser Glu Leu Asp Lys Ala Ile Gly Arg Asn Thr Asn Gly
        275                 280                 285

Val Ile Thr Lys Asp Glu Ala Glu Lys Leu Phe Asn Gln Asp Val Asp
    290                 295                 300

Ala Ala Val Arg Gly Ile Leu Arg Asn Ala Lys Leu Lys Pro Val Tyr
305                 310                 315                 320

Asp Ser Leu Asp Ala Val Arg Arg Ala Ala Leu Ile Asn Met Val Phe
                325                 330                 335

Gln Met Gly Glu Thr Gly Val Ala Gly Phe Thr Asn Ser Leu Arg Met
            340                 345                 350

Leu Gln Gln Lys Arg Trp Asp Glu Ala Val Asn Leu Ala Lys Ser
        355                 360                 365

Arg Trp Tyr Asn Gln Thr Pro Asn Arg Ala Lys Arg Val Ile Thr Thr
        370                 375                 380

Phe Arg Thr Gly Thr Trp Asp Ala Tyr Met Ala Leu Ala Arg Glu Arg
385                 390                 395                 400

Lys Thr Val Lys Thr Leu Gly Ile Ile Met Gly Thr Phe Ile Leu Cys
                405                 410                 415
```

```
Trp Leu Pro Phe Phe Ile Val Ala Leu Val Leu Pro Phe Cys Glu Ser
            420                 425                 430

Ser Cys His Met Pro Thr Leu Leu Gly Ala Ile Ile Asn Trp Leu Gly
        435                 440                 445

Tyr Ser Asn Ser Leu Leu Asn Pro Val Ile Tyr Ala Tyr Phe Asn Lys
    450                 455                 460

Asp Phe Gln Asn Ala Phe Lys Lys Ile Ile Lys Cys Lys Phe Cys Arg
465                 470                 475                 480

Gln

<210> SEQ ID NO 14
<211> LENGTH: 482
<212> TYPE: PRT
<213> ORGANISM: Artificial Sequence
<220> FEATURE:
<223> OTHER INFORMATION: synthetic polypeptide

<400> SEQUENCE: 14

Tyr Tyr Lys Asp Asp Ala Met Ser Pro Leu Asn Gln Ser Ala Glu
1               5                   10                  15

Gly Leu Pro Gln Glu Ala Ser Asn Arg Ser Leu Asn Ala Thr Glu Thr
            20                  25                  30

Ser Glu Ala Trp Asp Pro Arg Thr Leu Gln Ala Leu Lys Ile Ser Leu
        35                  40                  45

Ala Val Val Leu Ser Val Ile Thr Leu Ala Thr Val Leu Ser Asn Ala
    50                  55                  60

Phe Val Leu Thr Thr Ile Leu Leu Thr Arg Lys Leu His Thr Pro Ala
65                  70                  75                  80

Asn Tyr Leu Ile Gly Ser Leu Ala Thr Thr Asp Leu Leu Val Ser Ile
                85                  90                  95

Leu Val Met Pro Ile Ser Ile Ala Tyr Thr Ile Thr His Thr Trp Asn
            100                 105                 110

Phe Gly Gln Ile Leu Cys Asp Ile Trp Leu Ser Ser Asp Ile Thr Cys
        115                 120                 125

Cys Thr Ala Ser Ile Leu His Leu Cys Val Ile Ala Leu Asp Arg Tyr
    130                 135                 140

Trp Ala Ile Thr Asp Ala Leu Glu Tyr Ser Lys Arg Arg Thr Ala Gly
145                 150                 155                 160

His Ala Ala Thr Met Ile Ala Ile Val Trp Ala Ile Ser Ile Cys Ile
                165                 170                 175

Ser Ile Pro Pro Leu Phe Trp Arg Gln Ala Lys Ala Gln Glu Glu Met
            180                 185                 190

Ser Asp Cys Leu Val Asn Thr Ser Gln Ile Ser Tyr Thr Ile Tyr Ser
        195                 200                 205

Thr Cys Gly Ala Phe Tyr Ile Pro Ser Val Leu Leu Ile Ile Leu Tyr
    210                 215                 220

Gly Arg Ile Tyr Arg Ala Ala Arg Asn Arg Ile Asn Ile Phe Glu Met
225                 230                 235                 240

Leu Arg Ile Asp Glu Gly Leu Arg Leu Lys Ile Tyr Lys Asp Thr Glu
                245                 250                 255

Gly Tyr Tyr Thr Ile Gly Ile Gly His Leu Leu Thr Lys Ser Pro Ser
            260                 265                 270

Leu Asn Ala Ala Lys Ser Glu Leu Asp Lys Ala Ile Gly Arg Asn Thr
        275                 280                 285

Asn Gly Val Ile Thr Lys Asp Glu Ala Glu Lys Leu Phe Asn Gln Asp
```

```
            290                 295                 300
Val Asp Ala Ala Val Arg Gly Ile Leu Arg Asn Ala Lys Leu Lys Pro
305                 310                 315                 320

Val Tyr Asp Ser Leu Asp Ala Val Arg Arg Ala Ala Leu Ile Asn Met
                325                 330                 335

Val Phe Gln Met Gly Glu Thr Gly Val Ala Gly Phe Thr Asn Ser Leu
                340                 345                 350

Arg Met Leu Gln Gln Lys Arg Trp Asp Glu Ala Ala Val Asn Leu Ala
                355                 360                 365

Lys Ser Arg Trp Tyr Asn Gln Thr Pro Asn Arg Ala Lys Arg Val Ile
370                 375                 380

Thr Thr Phe Arg Thr Gly Thr Trp Asp Ala Tyr Ile Ser Ala Ala Arg
385                 390                 395                 400

Glu Arg Lys Ala Thr Lys Ile Leu Gly Ile Ile Leu Gly Ala Phe Ile
                405                 410                 415

Ile Cys Trp Leu Pro Phe Phe Val Val Ser Leu Val Leu Pro Ile Cys
                420                 425                 430

Arg Asp Ser Cys Trp Ile His Pro Ala Leu Phe Asp Phe Phe Thr Trp
                435                 440                 445

Leu Gly Tyr Leu Asn Ser Leu Ile Asn Pro Ile Ile Tyr Thr Val Phe
                450                 455                 460

Asn Glu Glu Phe Arg Gln Ala Phe Gln Lys Ile Val Pro Phe Arg Lys
465                 470                 475                 480

Ala Ser

<210> SEQ ID NO 15
<211> LENGTH: 591
<212> TYPE: PRT
<213> ORGANISM: Artificial Sequence
<220> FEATURE:
<223> OTHER INFORMATION: synthetic polypeptide

<400> SEQUENCE: 15

Asp Tyr Lys Asp Asp Ala Met Asp Ile Leu Cys Glu Glu Asn Thr
 1               5                  10                  15

Ser Leu Ser Ser Thr Thr Asn Ser Leu Met Gln Leu Asn Asp Asp Thr
                20                  25                  30

Arg Leu Tyr Ser Asn Asp Phe Asn Ser Gly Glu Ala Asn Thr Ser Asp
                35                  40                  45

Ala Phe Asn Trp Thr Val Asp Ser Glu Asn Arg Thr Asn Leu Ser Cys
50                  55                  60

Glu Gly Cys Leu Ser Pro Ser Cys Leu Ser Leu Leu His Leu Gln Glu
65                  70                  75                  80

Lys Asn Trp Ser Ala Leu Leu Thr Ala Val Val Ile Ile Leu Thr Ile
                85                  90                  95

Ala Gly Asn Ile Leu Val Ile Met Ala Val Ser Leu Glu Lys Lys Leu
                100                 105                 110

Gln Asn Ala Thr Asn Tyr Phe Leu Met Ser Leu Ala Ile Ala Asp Met
                115                 120                 125

Leu Leu Gly Phe Leu Val Met Pro Val Ser Met Leu Thr Ile Leu Tyr
                130                 135                 140

Gly Tyr Arg Trp Pro Leu Pro Ser Lys Leu Cys Ala Val Trp Ile Tyr
145                 150                 155                 160

Leu Asp Val Leu Phe Ser Thr Ala Ser Ile Met His Leu Cys Ala Ile
                165                 170                 175
```

-continued

```
Ser Leu Asp Arg Tyr Val Ala Ile Gln Asn Pro Ile His His Ser Arg
            180                 185                 190

Phe Asn Ser Arg Thr Lys Ala Phe Leu Lys Ile Ile Ala Val Trp Thr
        195                 200                 205

Ile Ser Val Gly Ile Ser Met Pro Ile Pro Val Phe Gly Leu Gln Asp
    210                 215                 220

Asp Ser Lys Val Phe Lys Glu Gly Ser Cys Leu Leu Ala Asp Asp Asn
225                 230                 235                 240

Phe Val Leu Ile Gly Ser Phe Val Ser Phe Ile Pro Leu Thr Ile
            245                 250                 255

Met Val Ile Thr Tyr Phe Leu Thr Ile Lys Ser Leu Gln Lys Glu Ala
            260                 265                 270

Asn Ile Phe Glu Met Leu Arg Ile Asp Glu Gly Leu Arg Leu Lys Ile
        275                 280                 285

Tyr Lys Asp Thr Glu Gly Tyr Tyr Thr Ile Gly Ile Gly His Leu Leu
    290                 295                 300

Thr Lys Ser Pro Ser Leu Asn Ala Ala Lys Ser Glu Leu Asp Lys Ala
305                 310                 315                 320

Ile Gly Arg Asn Thr Asn Gly Val Ile Thr Lys Asp Glu Ala Glu Lys
            325                 330                 335

Leu Phe Asn Gln Asp Val Asp Ala Ala Val Arg Gly Ile Leu Arg Asn
            340                 345                 350

Ala Lys Leu Lys Pro Val Tyr Asp Ser Leu Asp Ala Val Arg Arg Ala
        355                 360                 365

Ala Leu Ile Asn Met Val Phe Gln Met Gly Thr Gly Val Ala Gly
    370                 375                 380

Phe Thr Asn Ser Leu Arg Met Leu Gln Gln Lys Arg Trp Asp Glu Ala
385                 390                 395                 400

Ala Val Asn Leu Ala Lys Ser Arg Trp Tyr Asn Gln Thr Pro Asn Arg
            405                 410                 415

Ala Lys Arg Val Ile Thr Thr Phe Arg Thr Gly Thr Trp Asp Ala Tyr
            420                 425                 430

Gln Ser Ile Ser Asn Glu Gln Lys Ala Cys Lys Val Leu Gly Ile Val
        435                 440                 445

Phe Phe Leu Phe Val Val Met Trp Cys Pro Phe Phe Ile Thr Asn Ile
    450                 455                 460

Met Ala Val Ile Cys Lys Glu Ser Cys Asn Glu Asp Val Ile Gly Ala
465                 470                 475                 480

Leu Leu Asn Val Phe Val Trp Ile Gly Tyr Leu Ser Ser Ala Val Asn
            485                 490                 495

Pro Leu Val Tyr Thr Leu Phe Asn Lys Thr Tyr Arg Ser Ala Phe Ser
            500                 505                 510

Arg Tyr Ile Gln Cys Gln Tyr Lys Glu Asn Lys Lys Pro Leu Gln Leu
        515                 520                 525

Ile Leu Val Asn Thr Ile Pro Ala Leu Ala Tyr Lys Ser Ser Gln Leu
    530                 535                 540

Gln Met Gly Gln Lys Lys Asn Ser Lys Gln Asp Ala Lys Thr Thr Asp
545                 550                 555                 560

Asn Asp Cys Ser Met Val Ala Leu Gly Lys Gln His Ser Glu Glu Ala
            565                 570                 575

Ser Lys Asp Asn Ser Asp Gly Val Asn Glu Lys Val Ser Cys Val
            580                 585                 590
```

<210> SEQ ID NO 16

```
<211> LENGTH: 538
<212> TYPE: PRT
<213> ORGANISM: Artificial Sequence
<220> FEATURE:
<223> OTHER INFORMATION: synthetic polypeptide

<400> SEQUENCE: 16
```

| | | | | | | | | | | | | | | | |
|---|---|---|---|---|---|---|---|---|---|---|---|---|---|---|---|
|Asp|Tyr|Lys|Asp|Asp|Asp|Ala|Met|Ala|Asp|Ser|Cys|Arg|Asn|Leu|Thr|
|1| | |5| | | | |10| | | | |15| | |
|Tyr|Val|Arg|Gly|Ser|Val|Gly|Pro|Ala|Thr|Ser|Thr|Leu|Met|Phe|Val|
| | | |20| | | | |25| | | | |30| | |
|Ala|Gly|Val|Val|Gly|Asn|Gly|Leu|Ala|Leu|Gly|Ile|Leu|Ser|Ala|Arg|
| | | |35| | | | |40| | | | |45| | |
|Arg|Pro|Ala|Arg|Pro|Ser|Ala|Phe|Ala|Val|Leu|Val|Thr|Gly|Leu|Ala|
| |50| | | | |55| | | | |60| | | | |
|Ala|Thr|Asp|Leu|Leu|Gly|Thr|Ser|Phe|Leu|Ser|Pro|Ala|Val|Phe|Val|
|65| | | | |70| | | | |75| | | | |80|
|Ala|Tyr|Ala|Arg|Asn|Ser|Ser|Leu|Leu|Gly|Leu|Ala|Arg|Gly|Gly|Pro|
| | | | |85| | | | |90| | | | |95| |
|Ala|Leu|Cys|Asp|Ala|Phe|Ala|Phe|Ala|Met|Thr|Phe|Phe|Gly|Leu|Ala|
| | | |100| | | | |105| | | | |110| | |
|Ser|Met|Leu|Ile|Leu|Phe|Ala|Met|Ala|Val|Glu|Arg|Cys|Leu|Ala|Leu|
| | | |115| | | | |120| | | | |125| | |
|Ser|His|Pro|Tyr|Leu|Tyr|Ala|Gln|Leu|Asp|Gly|Pro|Arg|Cys|Ala|Arg|
| | | |130| | | | |135| | | | |140| | |
|Leu|Ala|Leu|Pro|Ala|Ile|Tyr|Ala|Phe|Cys|Val|Leu|Phe|Cys|Ala|Leu|
|145| | | | |150| | | | |155| | | | |160|
|Pro|Leu|Leu|Gly|Leu|Gly|Gln|His|Gln|Gln|Tyr|Cys|Pro|Gly|Ser|Trp|
| | | | |165| | | | |170| | | | |175| |
|Cys|Phe|Leu|Arg|Met|Arg|Trp|Ala|Gln|Pro|Gly|Gly|Ala|Ala|Phe|Ser|
| | | |180| | | | |185| | | | |190| | |
|Leu|Ala|Tyr|Ala|Gly|Leu|Val|Ala|Leu|Val|Ala|Ala|Ile|Phe|Leu|
| | | |195| | | | |200| | | | |205| | |
|Cys|Asn|Gly|Ser|Val|Thr|Leu|Ser|Leu|Cys|Arg|Met|Asn|Ile|Phe|Glu|
| | | |210| | | | |215| | | | |220| | |
|Met|Leu|Arg|Ile|Asp|Glu|Gly|Leu|Arg|Leu|Lys|Ile|Tyr|Lys|Asp|Thr|
|225| | | | |230| | | | |235| | | | |240|
|Glu|Gly|Tyr|Tyr|Thr|Ile|Gly|Ile|Gly|His|Leu|Leu|Thr|Lys|Ser|Pro|
| | | | |245| | | | |250| | | | |255| |
|Ser|Leu|Asn|Ala|Ala|Lys|Ser|Glu|Leu|Asp|Lys|Ala|Ile|Gly|Arg|Asn|
| | | |260| | | | |265| | | | |270| | |
|Thr|Asn|Gly|Val|Ile|Thr|Lys|Asp|Glu|Ala|Glu|Lys|Leu|Phe|Asn|Gln|
| | |275| | | | |280| | | | |285| | | |
|Asp|Val|Asp|Ala|Ala|Val|Arg|Gly|Ile|Leu|Arg|Asn|Ala|Lys|Leu|Lys|
| |290| | | | |295| | | | |300| | | | |
|Pro|Val|Tyr|Asp|Ser|Leu|Asp|Ala|Val|Arg|Arg|Ala|Ala|Leu|Ile|Asn|
|305| | | | |310| | | | |315| | | | |320|
|Met|Val|Phe|Gln|Met|Gly|Glu|Thr|Gly|Val|Ala|Gly|Phe|Thr|Asn|Ser|
| | | | |325| | | | |330| | | | |335| |
|Leu|Arg|Met|Leu|Gln|Gln|Lys|Arg|Trp|Asp|Glu|Ala|Ala|Val|Asn|Leu|
| | | |340| | | | |345| | | | |350| | |
|Ala|Lys|Ser|Arg|Trp|Tyr|Asn|Gln|Thr|Pro|Asn|Arg|Ala|Lys|Arg|Val|
| | |355| | | | |360| | | | |365| | | |
|Ile|Thr|Thr|Phe|Arg|Thr|Gly|Thr|Trp|Asp|Ala|Tyr|Arg|Thr|Gly|Glu|
| |370| | | | |375| | | | |380| | | | |

```
Asp Glu Val Asp His Leu Ile Leu Leu Ala Leu Met Thr Val Val Met
385                 390                 395                 400

Ala Val Cys Ser Leu Pro Leu Thr Ile Arg Cys Phe Thr Gln Ala Val
            405                 410                 415

Ala Pro Asp Ser Ser Glu Met Gly Asp Leu Leu Ala Phe Arg Phe
        420                 425                 430

Tyr Ala Phe Asn Pro Ile Leu Asp Pro Trp Val Phe Ile Leu Phe Arg
        435                 440                 445

Lys Ala Val Phe Gln Arg Leu Lys Leu Trp Val Cys Cys Leu Cys Leu
        450                 455                 460

Gly Pro Ala His Gly Asp Ser Gln Thr Pro Leu Ser Gln Leu Ala Ser
465                 470                 475                 480

Gly Arg Arg Asp Pro Arg Ala Pro Ser Ala Pro Val Gly Lys Glu Gly
            485                 490                 495

Ser Cys Val Pro Leu Ser Ala Trp Gly Glu Gly Gln Val Glu Pro Leu
            500                 505                 510

Pro Pro Thr Gln Gln Ser Ser Gly Ser Ala Val Gly Thr Ser Ser Lys
            515                 520                 525

Ala Glu Ala Ser Val Ala Cys Ser Leu Cys
530                 535
```

<210> SEQ ID NO 17
<211> LENGTH: 518
<212> TYPE: PRT
<213> ORGANISM: Artificial Sequence
<220> FEATURE:
<223> OTHER INFORMATION: synthetic polypeptide

<400> SEQUENCE: 17

```
Asp Tyr Lys Asp Asp Ala Met Ser Met Asn Asn Ser Lys Gln Leu
1               5                   10                  15

Val Ser Pro Ala Ala Leu Leu Ser Asn Thr Thr Cys Gln Thr Glu
            20                  25                  30

Asn Arg Leu Ser Val Phe Phe Ser Val Ile Phe Met Thr Val Gly Ile
            35                  40                  45

Leu Ser Asn Ser Leu Ala Ile Ala Ile Leu Met Lys Ala Tyr Gln Arg
50                  55                  60

Phe Arg Gln Lys Ser Lys Ala Ser Phe Leu Leu Leu Ala Ser Gly Leu
65                  70                  75                  80

Val Ile Thr Asp Phe Phe Gly His Leu Ile Asn Gly Ala Ile Ala Val
            85                  90                  95

Phe Val Tyr Ala Ser Asp Lys Glu Trp Ile Arg Phe Asp Gln Ser Asn
            100                 105                 110

Val Leu Cys Ser Ile Phe Gly Ile Cys Met Val Phe Ser Gly Leu Cys
            115                 120                 125

Pro Leu Leu Leu Gly Ser Val Met Ala Ile Glu Arg Cys Ile Gly Val
            130                 135                 140

Thr Lys Pro Ile Phe His Ser Thr Lys Ile Thr Ser Lys His Val Lys
145                 150                 155                 160

Met Met Leu Ser Gly Val Cys Leu Phe Ala Val Phe Ile Ala Leu Leu
            165                 170                 175

Pro Ile Leu Gly His Arg Asp Tyr Lys Ile Gln Ala Ser Arg Thr Trp
            180                 185                 190

Cys Phe Tyr Asn Thr Glu Asp Ile Lys Asp Trp Glu Asp Arg Phe Tyr
            195                 200                 205

Leu Leu Leu Phe Ser Phe Leu Gly Leu Leu Ala Leu Gly Val Ser Leu
```

```
            210                 215                 220
Leu Cys Asn Ala Ile Thr Gly Ile Thr Leu Leu Arg Val Asn Ile Phe
225                 230                 235                 240

Glu Met Leu Arg Ile Asp Glu Gly Leu Arg Leu Lys Ile Tyr Lys Asp
                245                 250                 255

Thr Glu Gly Tyr Tyr Thr Ile Gly Ile Gly His Leu Leu Thr Lys Ser
            260                 265                 270

Pro Ser Leu Asn Ala Ala Lys Ser Glu Leu Asp Lys Ala Ile Gly Arg
        275                 280                 285

Asn Thr Asn Gly Val Ile Thr Lys Asp Glu Ala Glu Lys Leu Phe Asn
290                 295                 300

Gln Asp Val Asp Ala Ala Val Arg Gly Ile Leu Arg Asn Ala Lys Leu
305                 310                 315                 320

Lys Pro Val Tyr Asp Ser Leu Asp Ala Val Arg Arg Ala Ala Leu Ile
                325                 330                 335

Asn Met Val Phe Gln Met Gly Glu Thr Gly Val Ala Gly Phe Thr Asn
            340                 345                 350

Ser Leu Arg Met Leu Gln Gln Lys Arg Trp Asp Glu Ala Ala Val Asn
        355                 360                 365

Leu Ala Lys Ser Arg Trp Tyr Asn Gln Thr Pro Asn Arg Ala Lys Arg
370                 375                 380

Val Ile Thr Thr Phe Arg Thr Gly Thr Trp Asp Ala Tyr Gln Gly Arg
385                 390                 395                 400

Ser His His Leu Glu Met Val Ile Gln Leu Leu Ala Ile Met Cys Val
                405                 410                 415

Ser Cys Ile Cys Trp Ser Pro Phe Leu Val Thr Met Ala Asn Ile Gly
            420                 425                 430

Ile Asn Gly Asn His Ser Leu Glu Thr Cys Glu Thr Thr Leu Phe Ala
        435                 440                 445

Leu Arg Met Ala Thr Trp Asn Gln Ile Leu Asp Pro Trp Val Tyr Ile
450                 455                 460

Leu Leu Arg Lys Ala Val Leu Lys Asn Leu Tyr Lys Leu Ala Ser Gln
465                 470                 475                 480

Cys Cys Gly Val His Val Ile Ser Leu His Ile Trp Glu Leu Ser Ser
                485                 490                 495

Ile Lys Asn Ser Leu Lys Val Ala Ile Ser Glu Ser Pro Val Ala
            500                 505                 510

Glu Lys Ser Ala Ser Thr
        515

<210> SEQ ID NO 18
<211> LENGTH: 515
<212> TYPE: PRT
<213> ORGANISM: Artificial Sequence
<220> FEATURE:
<223> OTHER INFORMATION: synthetic polypeptide

<400> SEQUENCE: 18

Asp Tyr Lys Asp Asp Asp Ala Met Ser Pro Cys Gly Pro Leu Asn Leu
1               5                   10                  15

Ser Leu Ala Gly Glu Ala Thr Thr Cys Ala Ala Pro Trp Val Pro Asn
                20                  25                  30

Thr Ser Ala Val Pro Pro Ser Gly Ala Ser Pro Ala Leu Pro Ile Phe
            35                  40                  45

Ser Met Thr Leu Gly Ala Val Ser Asn Leu Leu Ala Leu Ala Leu Leu
        50                  55                  60
```

-continued

```
Ala Gln Ala Ala Gly Arg Leu Arg Arg Arg Ser Ala Ala Thr Phe
 65                  70                  75                  80

Leu Leu Phe Val Ala Ser Leu Leu Ala Thr Asp Leu Ala Gly His Val
             85                  90                  95

Ile Pro Gly Ala Leu Val Leu Arg Leu Tyr Thr Ala Gly Arg Ala Pro
                100                 105                 110

Ala Gly Gly Ala Cys His Phe Leu Gly Gly Cys Met Val Phe Phe Gly
            115                 120                 125

Leu Cys Pro Leu Leu Leu Gly Cys Gly Met Ala Val Glu Arg Cys Val
130                 135                 140

Gly Val Thr Arg Pro Leu Leu His Ala Ala Arg Val Ser Val Ala Arg
145                 150                 155                 160

Ala Arg Leu Ala Leu Ala Ala Val Ala Ala Val Ala Leu Ala Val Ala
                165                 170                 175

Leu Leu Pro Leu Ala Arg Val Gly Arg Tyr Glu Leu Gln Tyr Pro Gly
            180                 185                 190

Thr Trp Cys Phe Ile Gly Leu Gly Pro Pro Gly Gly Trp Arg Gln Ala
        195                 200                 205

Leu Leu Ala Gly Leu Phe Ala Ser Leu Gly Leu Val Ala Leu Leu Ala
210                 215                 220

Ala Leu Val Cys Asn Thr Leu Ser Gly Leu Ala Leu Leu Arg Ala Asn
225                 230                 235                 240

Ile Phe Glu Met Leu Arg Ile Asp Glu Gly Leu Arg Leu Lys Ile Tyr
                245                 250                 255

Lys Asp Thr Glu Gly Tyr Tyr Thr Ile Gly Ile Gly His Leu Leu Thr
            260                 265                 270

Lys Ser Pro Ser Leu Asn Ala Ala Lys Ser Glu Leu Asp Lys Ala Ile
        275                 280                 285

Gly Arg Asn Thr Asn Gly Val Ile Thr Lys Asp Glu Ala Glu Lys Leu
    290                 295                 300

Phe Asn Gln Asp Val Asp Ala Ala Val Arg Gly Ile Leu Arg Asn Ala
305                 310                 315                 320

Lys Leu Lys Pro Val Tyr Asp Ser Leu Asp Ala Val Arg Arg Ala Ala
                325                 330                 335

Leu Ile Asn Met Val Phe Gln Met Gly Glu Thr Gly Val Ala Gly Phe
            340                 345                 350

Thr Asn Ser Leu Arg Met Leu Gln Gln Lys Arg Trp Asp Glu Ala Ala
        355                 360                 365

Val Asn Leu Ala Lys Ser Arg Trp Tyr Asn Gln Thr Pro Asn Arg Ala
    370                 375                 380

Lys Arg Val Ile Thr Thr Phe Arg Thr Gly Thr Trp Asp Ala Tyr Arg
385                 390                 395                 400

Ala Arg Ala His Asp Val Glu Met Val Gly Gln Leu Val Gly Ile Met
                405                 410                 415

Val Val Ser Cys Ile Cys Trp Ser Pro Met Leu Val Leu Val Ala Leu
            420                 425                 430

Ala Val Gly Gly Trp Ser Ser Thr Ser Leu Gln Arg Pro Leu Phe Leu
        435                 440                 445

Ala Val Arg Leu Ala Ser Trp Asn Gln Ile Leu Asp Pro Trp Val Tyr
    450                 455                 460

Ile Leu Leu Arg Gln Ala Val Leu Arg Gln Leu Leu Arg Leu Leu Pro
465                 470                 475                 480

Pro Arg Ala Gly Ala Lys Gly Gly Pro Ala Gly Leu Gly Leu Thr Pro
```

```
                        485                 490                 495
Ser Ala Trp Glu Ala Ser Ser Leu Arg Ser Ser Arg His Ser Gly Leu
                    500                 505                 510

Ser His Phe
    515

<210> SEQ ID NO 19
<211> LENGTH: 611
<212> TYPE: PRT
<213> ORGANISM: Artificial Sequence
<220> FEATURE:
<223> OTHER INFORMATION: synthetic polypeptide

<400> SEQUENCE: 19

Asp Tyr Lys Asp Asp Ala Met Lys Ser Ile Leu Asp Gly Leu Ala
  1               5                  10                  15

Asp Thr Thr Phe Arg Thr Ile Thr Thr Asp Leu Leu Tyr Val Gly Ser
                 20                  25                  30

Asn Asp Ile Gln Tyr Glu Asp Ile Lys Gly Asp Met Ala Ser Lys Leu
             35                  40                  45

Gly Tyr Phe Pro Gln Lys Phe Pro Leu Thr Ser Phe Arg Gly Ser Pro
 50                  55                  60

Phe Gln Glu Lys Met Thr Ala Gly Asp Asn Pro Gln Leu Val Pro Ala
 65                  70                  75                  80

Asp Gln Val Asn Ile Thr Glu Phe Tyr Asn Lys Ser Leu Ser Ser Phe
                 85                  90                  95

Lys Glu Asn Glu Glu Asn Ile Gln Cys Gly Glu Asn Phe Met Asp Ile
                100                 105                 110

Glu Cys Phe Met Val Leu Asn Pro Ser Gln Gln Leu Ala Ile Ala Val
            115                 120                 125

Leu Ser Leu Thr Leu Gly Thr Phe Thr Val Leu Glu Asn Leu Leu Val
130                 135                 140

Leu Cys Val Ile Leu His Ser Arg Ser Leu Arg Cys Arg Pro Ser Tyr
145                 150                 155                 160

His Phe Ile Gly Ser Leu Ala Val Ala Asp Leu Leu Gly Ser Val Ile
                165                 170                 175

Phe Val Tyr Ser Phe Ile Asp Phe His Val Phe His Arg Lys Asp Ser
            180                 185                 190

Arg Asn Val Phe Leu Phe Lys Leu Gly Gly Val Thr Ala Ser Phe Thr
        195                 200                 205

Ala Ser Val Gly Ser Leu Phe Leu Thr Ala Ile Asp Arg Tyr Ile Ser
    210                 215                 220

Ile His Arg Pro Leu Ala Tyr Lys Arg Ile Val Thr Arg Pro Lys Ala
225                 230                 235                 240

Val Val Ala Phe Cys Leu Met Trp Thr Ile Ala Ile Val Ile Ala Val
                245                 250                 255

Leu Pro Leu Leu Gly Trp Asn Cys Glu Lys Leu Gln Ser Val Cys Ser
            260                 265                 270

Asp Ile Phe Pro His Ile Asp Glu Thr Tyr Leu Met Phe Trp Ile Gly
        275                 280                 285

Val Thr Ser Val Leu Leu Leu Phe Ile Val Tyr Ala Tyr Met Tyr Ile
    290                 295                 300

Leu Trp Lys Ala His Ser His Asn Ile Phe Glu Met Leu Arg Ile Asp
305                 310                 315                 320

Glu Gly Leu Arg Leu Lys Ile Tyr Lys Asp Thr Glu Gly Tyr Tyr Thr
                325                 330                 335
```

Ile Gly Ile Gly His Leu Leu Thr Lys Ser Pro Ser Leu Asn Ala Ala
            340                 345                 350

Lys Ser Glu Leu Asp Lys Ala Ile Gly Arg Asn Thr Asn Gly Val Ile
        355                 360                 365

Thr Lys Asp Glu Ala Glu Lys Leu Phe Asn Gln Asp Val Asp Ala Ala
370                 375                 380

Val Arg Gly Ile Leu Arg Asn Ala Lys Leu Lys Pro Val Tyr Asp Ser
385                 390                 395                 400

Leu Asp Ala Val Arg Arg Ala Ala Leu Ile Asn Met Val Phe Gln Met
                405                 410                 415

Gly Glu Thr Gly Val Ala Gly Phe Thr Asn Ser Leu Arg Met Leu Gln
            420                 425                 430

Gln Lys Arg Trp Asp Glu Ala Ala Val Asn Leu Ala Lys Ser Arg Trp
        435                 440                 445

Tyr Asn Gln Thr Pro Asn Arg Ala Lys Arg Val Ile Thr Thr Phe Arg
450                 455                 460

Thr Gly Thr Trp Asp Ala Tyr Asp Gln Ala Arg Met Asp Ile Arg Leu
465                 470                 475                 480

Ala Lys Thr Leu Val Leu Ile Leu Val Val Leu Ile Ile Cys Trp Gly
                485                 490                 495

Pro Leu Leu Ala Ile Met Val Tyr Asp Val Phe Gly Lys Met Asn Lys
            500                 505                 510

Leu Ile Lys Thr Val Phe Ala Phe Cys Ser Met Leu Cys Leu Leu Asn
        515                 520                 525

Ser Thr Val Asn Pro Ile Ile Tyr Ala Leu Arg Ser Lys Asp Leu Arg
530                 535                 540

His Ala Phe Arg Ser Met Phe Pro Ser Cys Glu Gly Thr Ala Gln Pro
545                 550                 555                 560

Leu Asp Asn Ser Met Gly Asp Ser Asp Cys Leu His Lys His Ala Asn
                565                 570                 575

Asn Ala Ala Ser Val His Arg Ala Ala Glu Ser Cys Ile Lys Ser Thr
            580                 585                 590

Val Lys Ile Ala Lys Val Thr Met Ser Val Ser Thr Asp Thr Ser Ala
        595                 600                 605

Glu Ala Leu
    610

<210> SEQ ID NO 20
<211> LENGTH: 565
<212> TYPE: PRT
<213> ORGANISM: Artificial Sequence
<220> FEATURE:
<223> OTHER INFORMATION: synthetic polypeptide

<400> SEQUENCE: 20

Asp Tyr Lys Asp Asp Ala Asp Asn Pro Glu Arg Tyr Ser Thr Asn
1               5                   10                  15

Leu Ser Asn His Val Asp Asp Phe Thr Thr Phe Arg Gly Thr Glu Leu
            20                  25                  30

Ser Phe Leu Val Thr Thr His Gln Pro Thr Asn Leu Val Leu Pro Ser
        35                  40                  45

Asn Gly Ser Met His Asn Tyr Cys Pro Gln Gln Thr Lys Ile Thr Ser
    50                  55                  60

Ala Phe Lys Tyr Ile Asn Thr Val Ile Ser Cys Thr Ile Phe Ile Val
65                  70                  75                  80

```
Gly Met Val Gly Asn Ala Thr Leu Leu Arg Ile Ile Tyr Gln Asn Lys
                 85                  90                  95

Cys Met Arg Asn Gly Pro Asn Ala Leu Ile Ala Ser Leu Ala Leu Gly
            100                 105                 110

Asp Leu Ile Tyr Val Val Ile Asp Leu Pro Ile Asn Val Phe Lys Leu
            115                 120                 125

Leu Ala Gly Arg Trp Pro Phe Asp His Asn Asp Phe Gly Val Phe Leu
        130                 135                 140

Cys Lys Leu Phe Pro Phe Leu Gln Lys Ser Ser Val Gly Ile Thr Val
145                 150                 155                 160

Leu Asn Leu Cys Ala Leu Ser Val Asp Arg Tyr Arg Ala Val Ala Ser
                165                 170                 175

Trp Ser Arg Val Gln Gly Ile Gly Ile Pro Leu Val Thr Ala Ile Glu
            180                 185                 190

Ile Val Ser Ile Trp Ile Leu Ser Phe Ile Leu Ala Ile Pro Glu Ala
            195                 200                 205

Ile Gly Phe Val Met Val Pro Phe Glu Tyr Arg Gly Glu Gln His Lys
        210                 215                 220

Thr Cys Met Leu Asn Ala Thr Ser Lys Phe Met Glu Phe Tyr Gln Asp
225                 230                 235                 240

Val Lys Asp Trp Trp Leu Phe Gly Phe Tyr Phe Cys Met Pro Leu Val
                245                 250                 255

Cys Thr Ala Ile Phe Tyr Thr Leu Met Thr Cys Glu Met Leu Asn Arg
            260                 265                 270

Arg Asn Ile Phe Glu Met Leu Arg Ile Asp Glu Gly Leu Arg Leu Lys
        275                 280                 285

Ile Tyr Lys Asp Thr Glu Gly Tyr Tyr Thr Ile Gly Ile Gly His Leu
        290                 295                 300

Leu Thr Lys Ser Pro Ser Leu Asn Ala Ala Lys Ser Glu Leu Asp Lys
305                 310                 315                 320

Ala Ile Gly Arg Asn Thr Asn Gly Val Ile Thr Lys Asp Glu Ala Glu
                325                 330                 335

Lys Leu Phe Asn Gln Asp Val Asp Ala Ala Val Arg Gly Ile Leu Arg
            340                 345                 350

Asn Ala Lys Leu Lys Pro Val Tyr Asp Ser Leu Asp Ala Val Arg Arg
        355                 360                 365

Ala Ala Leu Ile Asn Met Val Phe Gln Met Gly Glu Thr Gly Val Ala
        370                 375                 380

Gly Phe Thr Asn Ser Leu Arg Met Leu Gln Gln Lys Arg Trp Asp Glu
385                 390                 395                 400

Ala Ala Val Asn Leu Ala Lys Ser Arg Trp Tyr Asn Gln Thr Pro Asn
                405                 410                 415

Arg Ala Lys Arg Val Ile Thr Thr Phe Arg Thr Gly Thr Trp Asp Ala
            420                 425                 430

Tyr Glu His Leu Lys Gln Arg Arg Glu Val Ala Lys Thr Val Phe Cys
        435                 440                 445

Leu Val Val Ile Phe Ala Leu Cys Trp Phe Pro Leu His Leu Ser Arg
        450                 455                 460

Ile Leu Lys Lys Thr Val Tyr Asn Glu Met Asp Lys Asn Arg Cys Glu
465                 470                 475                 480

Leu Leu Ser Phe Leu Leu Leu Met Asp Tyr Ile Gly Ile Asn Leu Ala
                485                 490                 495

Thr Met Asn Ser Cys Ile Asn Pro Ile Ala Leu Tyr Phe Val Ser Lys
            500                 505                 510
```

Lys Phe Lys Asn Cys Phe Gln Ser Cys Leu Cys Cys Cys Tyr Gln
            515                 520                 525

Ser Lys Ser Leu Met Thr Ser Val Pro Met Asn Gly Thr Ser Ile Gln
            530                 535                 540

Trp Lys Asn His Asp Gln Asn Asn His Asn Thr Asp Arg Ser Ser His
545                 550                 555                 560

Lys Asp Ser Met Asn
            565

<210> SEQ ID NO 21
<211> LENGTH: 431
<212> TYPE: PRT
<213> ORGANISM: Artificial Sequence
<220> FEATURE:
<223> OTHER INFORMATION: synthetic polypeptide

<400> SEQUENCE: 21

Phe Tyr Lys Asp Asp Ala Met Ala Asn Ser Ala Ser Pro Glu Gln
  1               5                  10                  15

Asn Gln Asn His Cys Ser Ala Ile Asn Asn Ser Ile Pro Leu Met Gln
                 20                  25                  30

Gly Asn Leu Pro Thr Leu Thr Leu Ser Gly Lys Ile Arg Val Thr Val
             35                  40                  45

Thr Phe Phe Leu Phe Leu Leu Ser Ala Thr Phe Asn Ala Ser Phe Leu
         50                  55                  60

Leu Lys Leu Gln Lys Trp Thr Gln Lys Glu Lys Gly Lys Lys Leu
 65                  70                  75                  80

Ser Arg Met Lys Leu Leu Leu Lys His Leu Thr Leu Ala Asn Leu Leu
                 85                  90                  95

Glu Thr Leu Ile Val Met Pro Leu Asp Gly Met Trp Asn Ile Thr Val
                100                 105                 110

Gln Trp Tyr Ala Gly Glu Leu Leu Cys Lys Val Leu Ser Tyr Leu Lys
            115                 120                 125

Leu Phe Ser Met Tyr Ala Pro Ala Phe Met Met Val Val Ile Ser Leu
        130                 135                 140

Asp Arg Ser Leu Ala Ile Thr Arg Pro Leu Ala Leu Lys Ser Asn Ser
145                 150                 155                 160

Lys Val Gly Gln Ser Met Val Gly Leu Ala Trp Ile Leu Ser Ser Val
                165                 170                 175

Phe Ala Gly Pro Gln Leu Tyr Ile Phe Arg Met Ile His Leu Ala Asp
            180                 185                 190

Ser Ser Gly Gln Thr Lys Val Asn Ile Phe Glu Met Leu Arg Ile Asp
        195                 200                 205

Glu Gly Leu Arg Leu Lys Ile Tyr Lys Asp Thr Glu Gly Tyr Tyr Thr
    210                 215                 220

Ile Gly Ile Gly His Leu Leu Thr Lys Ser Pro Ser Leu Asn Ala Ala
225                 230                 235                 240

Lys Ser Glu Leu Asp Lys Ala Ile Gly Arg Asn Thr Asn Gly Val Ile
                245                 250                 255

Thr Lys Asp Glu Ala Glu Lys Leu Phe Asn Gln Asp Val Asp Ala Ala
            260                 265                 270

Val Arg Gly Ile Leu Arg Asn Ala Lys Leu Lys Pro Val Tyr Asp Ser
        275                 280                 285

Leu Asp Ala Val Arg Arg Ala Ala Leu Ile Asn Met Val Phe Gln Met
    290                 295                 300

Gly Glu Thr Gly Val Ala Gly Phe Thr Asn Ser Leu Arg Met Leu Gln
305                 310                 315                 320

Gln Lys Arg Trp Asp Glu Ala Ala Val Asn Leu Ala Lys Ser Arg Trp
            325                 330                 335

Tyr Asn Gln Thr Pro Asn Arg Ala Lys Arg Val Ile Thr Thr Phe Arg
        340                 345                 350

Thr Gly Thr Trp Asp Ala Tyr Asn Ile Pro Arg Ala Arg Leu Lys Thr
    355                 360                 365

Leu Lys Met Thr Val Ala Phe Ala Thr Ser Phe Thr Val Cys Trp Thr
370                 375                 380

Pro Tyr Tyr Val Leu Gly Ile Trp Tyr Trp Phe Asp Pro Glu Met Leu
385                 390                 395                 400

Asn Arg Leu Ser Asp Pro Val Asn His Phe Phe Phe Leu Phe Ala Phe
            405                 410                 415

Leu Asn Pro Cys Phe Asp Pro Leu Ile Tyr Gly Tyr Phe Ser Leu
        420                 425                 430

<210> SEQ ID NO 22
<211> LENGTH: 523
<212> TYPE: PRT
<213> ORGANISM: Artificial Sequence
<220> FEATURE:
<223> OTHER INFORMATION: synthetic polypeptide

<400> SEQUENCE: 22

Asp Tyr Lys Asp Asp Ala Met Glu Gly Ala Leu Ala Ala Asn Trp
1               5                   10                  15

Ser Ala Glu Ala Ala Asn Ala Ser Ala Ala Pro Gly Ala Glu Gly
            20                  25                  30

Asn Arg Thr Ala Gly Pro Pro Arg Arg Asn Glu Ala Leu Ala Arg Val
    35                  40                  45

Glu Val Ala Val Leu Cys Leu Ile Leu Leu Ala Leu Ser Gly Asn
50                  55                  60

Ala Cys Val Leu Leu Ala Leu Arg Thr Thr Arg Gln Lys His Ser Arg
65                  70                  75                  80

Leu Phe Phe Phe Met Lys His Leu Ser Ile Ala Asp Leu Val Val Ala
                85                  90                  95

Val Phe Gln Val Leu Pro Gln Leu Leu Trp Asp Ile Thr Phe Arg Phe
            100                 105                 110

Tyr Gly Pro Asp Leu Leu Cys Arg Leu Val Lys Tyr Leu Gln Val Val
        115                 120                 125

Gly Met Phe Ala Ser Thr Tyr Leu Leu Leu Leu Met Ser Leu Asp Arg
    130                 135                 140

Cys Leu Ala Ile Cys Gln Pro Leu Arg Ser Leu Arg Arg Arg Thr Asp
145                 150                 155                 160

Arg Leu Ala Val Leu Ala Thr Trp Leu Gly Cys Leu Val Ala Ser Ala
                165                 170                 175

Pro Gln Val His Ile Phe Ser Leu Arg Glu Val Ala Asp Gly Val Phe
            180                 185                 190

Asp Cys Trp Ala Val Phe Ile Gln Pro Trp Gly Pro Lys Ala Tyr Ile
        195                 200                 205

Thr Trp Ile Thr Leu Ala Val Tyr Ile Val Pro Val Ile Val Leu Ala
    210                 215                 220

Ala Cys Tyr Gly Leu Ile Ser Phe Lys Ile Trp Gln Asn Leu Asn Ile
225                 230                 235                 240

Phe Glu Met Leu Arg Ile Asp Glu Gly Leu Arg Leu Lys Ile Tyr Lys

```
                    245                 250                 255
Asp Thr Glu Gly Tyr Tyr Thr Ile Gly Ile Gly His Leu Leu Thr Lys
                260                 265                 270

Ser Pro Ser Leu Asn Ala Ala Lys Ser Glu Leu Asp Lys Ala Ile Gly
            275                 280                 285

Arg Asn Thr Asn Gly Val Ile Thr Lys Asp Glu Ala Glu Lys Leu Phe
        290                 295                 300

Asn Gln Asp Val Asp Ala Ala Val Arg Gly Ile Leu Arg Asn Ala Lys
305                 310                 315                 320

Leu Lys Pro Val Tyr Asp Ser Leu Asp Ala Val Arg Arg Ala Ala Leu
                325                 330                 335

Ile Asn Met Val Phe Gln Met Gly Glu Thr Gly Val Ala Gly Phe Thr
            340                 345                 350

Asn Ser Leu Arg Met Leu Gln Gln Lys Arg Trp Asp Glu Ala Ala Val
        355                 360                 365

Asn Leu Ala Lys Ser Arg Trp Tyr Asn Gln Thr Pro Asn Arg Ala Lys
    370                 375                 380

Arg Val Ile Thr Thr Phe Arg Thr Gly Thr Trp Asp Ala Tyr Leu Ile
385                 390                 395                 400

Ser Lys Ala Lys Ile Arg Thr Val Lys Met Thr Phe Ile Ile Val Leu
                405                 410                 415

Ala Phe Ile Val Cys Trp Thr Pro Phe Phe Val Gln Met Trp Ser
            420                 425                 430

Val Trp Asp Ala Asn Ala Pro Lys Glu Ala Ser Ala Phe Ile Ile Val
        435                 440                 445

Met Leu Leu Ala Ser Leu Asn Ser Cys Cys Asn Pro Trp Ile Tyr Met
    450                 455                 460

Leu Phe Thr Gly His Leu Phe His Glu Leu Val Gln Arg Phe Leu Cys
465                 470                 475                 480

Cys Ser Ala Ser Tyr Leu Lys Gly Arg Arg Leu Gly Glu Thr Ser Ala
                485                 490                 495

Ser Lys Lys Ser Asn Ser Ser Ser Phe Val Leu Ser His Arg Ser Ser
            500                 505                 510

Ser Gln Arg Ser Cys Ser Gln Pro Ser Thr Ala
        515                 520

<210> SEQ ID NO 23
<211> LENGTH: 488
<212> TYPE: PRT
<213> ORGANISM: Artificial Sequence
<220> FEATURE:
<223> OTHER INFORMATION: synthetic polypeptide

<400> SEQUENCE: 23

Asp Tyr Lys Asp Asp Ala Met Val Asn Ser Thr His Arg Gly Met
1               5                   10                  15

His Thr Ser Leu His Leu Trp Asn Arg Ser Ser Tyr Arg Leu His Ser
                20                  25                  30

Asn Ala Ser Glu Ser Leu Gly Lys Gly Tyr Ser Asp Gly Gly Cys Tyr
            35                  40                  45

Glu Gln Leu Phe Val Ser Pro Glu Val Phe Val Thr Leu Gly Val Ile
        50                  55                  60

Ser Leu Leu Glu Asn Ile Leu Val Ile Val Ala Ile Ala Lys Asn Lys
65                  70                  75                  80

Asn Leu His Ser Pro Met Tyr Phe Phe Ile Cys Ser Leu Ala Val Ala
                85                  90                  95
```

```
Asp Met Leu Val Ser Val Ser Asn Gly Ser Glu Thr Ile Val Ile Thr
            100                 105                 110

Leu Leu Asn Ser Thr Asp Thr Asp Ala Gln Ser Phe Thr Val Asn Ile
            115                 120                 125

Asp Asn Val Ile Asp Ser Val Ile Cys Ser Ser Leu Leu Ala Ser Ile
        130                 135                 140

Cys Ser Leu Leu Ser Ile Ala Val Asp Arg Tyr Phe Thr Ile Phe Tyr
145                 150                 155                 160

Ala Leu Gln Tyr His Asn Ile Met Thr Val Lys Arg Val Gly Ile Ile
                165                 170                 175

Ile Ser Cys Ile Trp Ala Ala Cys Thr Val Ser Gly Ile Leu Phe Ile
            180                 185                 190

Ile Tyr Ser Asp Ser Ser Ala Val Ile Ile Cys Leu Ile Thr Met Phe
            195                 200                 205

Phe Thr Met Leu Ala Leu Met Ala Ser Leu Tyr Val His Met Phe Leu
210                 215                 220

Met Ala Arg Leu His Ile Asn Ile Phe Glu Met Leu Arg Ile Asp Glu
225                 230                 235                 240

Gly Leu Arg Leu Lys Ile Tyr Lys Asp Thr Glu Gly Tyr Tyr Thr Ile
                245                 250                 255

Gly Ile Gly His Leu Leu Thr Lys Ser Pro Ser Leu Asn Ala Ala Lys
            260                 265                 270

Ser Glu Leu Asp Lys Ala Ile Gly Arg Asn Thr Asn Gly Val Ile Thr
            275                 280                 285

Lys Asp Glu Ala Glu Lys Leu Phe Asn Gln Asp Val Asp Ala Ala Val
        290                 295                 300

Arg Gly Ile Leu Arg Asn Ala Lys Leu Lys Pro Val Tyr Asp Ser Leu
305                 310                 315                 320

Asp Ala Val Arg Arg Ala Ala Leu Ile Asn Met Val Phe Gln Met Gly
                325                 330                 335

Glu Thr Gly Val Ala Gly Phe Thr Asn Ser Leu Arg Met Leu Gln Gln
            340                 345                 350

Lys Arg Trp Asp Glu Ala Ala Val Asn Leu Ala Lys Ser Arg Trp Tyr
            355                 360                 365

Asn Gln Thr Pro Asn Arg Ala Lys Arg Val Ile Thr Thr Phe Arg Thr
        370                 375                 380

Gly Thr Trp Asp Ala Tyr Ile Arg Gln Gly Ala Asn Met Lys Gly Ala
385                 390                 395                 400

Ile Thr Leu Thr Ile Leu Ile Gly Val Phe Val Val Cys Trp Ala Pro
                405                 410                 415

Phe Phe Leu His Leu Ile Phe Tyr Ile Ser Cys Pro Gln Asn Pro Tyr
            420                 425                 430

Cys Val Cys Phe Met Ser His Phe Asn Leu Tyr Leu Ile Leu Ile Met
            435                 440                 445

Cys Asn Ser Ile Ile Asp Pro Leu Ile Tyr Ala Leu Arg Ser Gln Glu
        450                 455                 460

Leu Arg Lys Thr Phe Lys Glu Ile Ile Cys Cys Tyr Pro Leu Gly Gly
465                 470                 475                 480

Leu Cys Asp Leu Ser Ser Arg Tyr
                485

<210> SEQ ID NO 24
<211> LENGTH: 541
<212> TYPE: PRT
```

<213> ORGANISM: Artificial Sequence
<220> FEATURE:
<223> OTHER INFORMATION: synthetic polypeptide

<400> SEQUENCE: 24

```
Asp Tyr Lys Asp Asp Ala Met Asn Ser Thr Leu Phe Ser Gln Val
 1               5                  10                  15

Glu Asn His Ser Val His Ser Asn Phe Ser Glu Lys Asn Ala Gln Leu
            20                  25                  30

Leu Ala Phe Glu Asn Asp Asp Cys His Leu Pro Leu Ala Met Ile Phe
        35                  40                  45

Thr Leu Ala Leu Ala Tyr Gly Ala Val Ile Ile Leu Gly Val Ser Gly
    50                  55                  60

Asn Leu Ala Leu Ile Ile Ile Ile Leu Lys Gln Lys Glu Met Arg Asn
65                  70                  75                  80

Val Thr Asn Ile Leu Ile Val Asn Leu Ser Phe Ser Asp Leu Leu Val
                85                  90                  95

Ala Ile Met Cys Leu Pro Phe Thr Phe Val Tyr Thr Leu Met Asp His
            100                 105                 110

Trp Val Phe Gly Glu Ala Met Cys Lys Leu Asn Pro Phe Val Gln Cys
        115                 120                 125

Val Ser Ile Thr Val Ser Ile Phe Ser Leu Val Leu Ile Ala Val Glu
    130                 135                 140

Arg His Gln Leu Ile Ile Asn Pro Arg Gly Trp Arg Pro Asn Asn Arg
145                 150                 155                 160

His Ala Tyr Val Gly Ile Ala Val Ile Trp Val Leu Ala Val Ala Ser
                165                 170                 175

Ser Leu Pro Phe Leu Ile Tyr Gln Val Met Thr Asp Glu Pro Phe Gln
            180                 185                 190

Asn Val Thr Leu Asp Ala Tyr Lys Asp Lys Tyr Val Cys Phe Asp Gln
        195                 200                 205

Phe Pro Ser Asp Ser His Arg Leu Ser Tyr Thr Thr Leu Leu Leu Val
    210                 215                 220

Leu Gln Tyr Phe Gly Pro Leu Cys Phe Ile Phe Ile Cys Tyr Phe Lys
225                 230                 235                 240

Ile Tyr Ile Arg Leu Lys Arg Arg Asn Asn Ile Phe Glu Met Leu Arg
                245                 250                 255

Ile Asp Glu Gly Leu Arg Leu Lys Ile Tyr Lys Asp Thr Glu Gly Tyr
            260                 265                 270

Tyr Thr Ile Gly Ile Gly His Leu Leu Thr Lys Ser Pro Ser Leu Asn
        275                 280                 285

Ala Ala Lys Ser Glu Leu Asp Lys Ala Ile Gly Arg Asn Thr Asn Gly
    290                 295                 300

Val Ile Thr Lys Asp Glu Ala Glu Lys Leu Phe Asn Gln Asp Val Asp
305                 310                 315                 320

Ala Ala Val Arg Gly Ile Leu Arg Asn Ala Lys Leu Lys Pro Val Tyr
                325                 330                 335

Asp Ser Leu Asp Ala Val Arg Arg Ala Ala Leu Ile Asn Met Val Phe
            340                 345                 350

Gln Met Gly Glu Thr Gly Val Ala Gly Phe Thr Asn Ser Leu Arg Met
        355                 360                 365

Leu Gln Gln Lys Arg Trp Asp Glu Ala Ala Val Asn Leu Ala Lys Ser
    370                 375                 380

Arg Trp Tyr Asn Gln Thr Pro Asn Arg Ala Lys Arg Val Ile Thr Thr
385                 390                 395                 400
```

```
Phe Arg Thr Gly Thr Trp Asp Ala Tyr Tyr Arg Ser Glu Thr Lys
            405                 410                 415

Arg Ile Asn Ile Met Leu Leu Ser Ile Val Val Ala Phe Ala Val Cys
            420                 425                 430

Trp Leu Pro Leu Thr Ile Phe Asn Thr Val Phe Asp Trp Asn His Gln
            435                 440                 445

Ile Ile Ala Thr Cys Asn His Asn Leu Leu Phe Leu Leu Cys His Leu
450                 455                 460

Thr Ala Met Ile Ser Thr Cys Val Asn Pro Ile Phe Tyr Gly Phe Leu
465                 470                 475                 480

Asn Lys Asn Phe Gln Arg Asp Leu Gln Phe Phe Phe Asn Phe Cys Asp
            485                 490                 495

Phe Arg Ser Arg Asp Asp Tyr Glu Thr Ile Ala Met Ser Thr Met
            500                 505                 510

His Thr Asp Val Ser Lys Thr Ser Leu Lys Gln Ala Ser Pro Val Ala
            515                 520                 525

Phe Lys Lys Ile Asn Asn Asn Asp Asn Glu Lys Ile
530                 535                 540

<210> SEQ ID NO 25
<211> LENGTH: 561
<212> TYPE: PRT
<213> ORGANISM: Artificial Sequence
<220> FEATURE:
<223> OTHER INFORMATION: synthetic polypeptide

<400> SEQUENCE: 25

Asp Tyr Lys Asp Asp Ala Met Asp Ser Ser Ala Ala Pro Thr Asn
1               5                   10                  15

Ala Ser Asn Cys Thr Asp Ala Leu Ala Tyr Ser Ser Cys Ser Pro Ala
                20                  25                  30

Pro Ser Pro Gly Ser Trp Val Asn Leu Ser His Leu Asp Gly Asn Leu
            35                  40                  45

Ser Asp Pro Cys Gly Pro Asn Arg Thr Asp Leu Gly Gly Arg Asp Ser
50                  55                  60

Leu Cys Pro Pro Thr Gly Ser Pro Ser Met Ile Thr Ala Ile Thr Ile
65                  70                  75                  80

Met Ala Leu Tyr Ser Ile Val Cys Val Val Gly Leu Phe Gly Asn Phe
                85                  90                  95

Leu Val Met Tyr Val Ile Val Arg Tyr Thr Lys Met Lys Thr Ala Thr
            100                 105                 110

Asn Ile Tyr Ile Phe Asn Leu Ala Leu Ala Asp Ala Leu Ala Thr Ser
            115                 120                 125

Thr Leu Pro Phe Gln Ser Val Asn Tyr Leu Met Gly Thr Trp Pro Phe
130                 135                 140

Gly Thr Ile Leu Cys Lys Ile Val Ile Ser Ile Asp Tyr Tyr Asn Met
145                 150                 155                 160

Phe Thr Ser Ile Phe Thr Leu Cys Thr Met Ser Val Asp Arg Tyr Ile
                165                 170                 175

Ala Val Cys His Pro Val Lys Ala Leu Asp Phe Arg Thr Pro Arg Asn
            180                 185                 190

Ala Lys Ile Ile Asn Val Cys Asn Trp Ile Leu Ser Ser Ala Ile Gly
            195                 200                 205

Leu Pro Val Met Phe Met Ala Thr Thr Lys Tyr Arg Gln Gly Ser Ile
210                 215                 220
```

Asp Cys Thr Leu Thr Phe Ser His Pro Thr Trp Tyr Trp Glu Asn Leu
225                 230                 235                 240

Leu Lys Ile Cys Val Phe Ile Phe Ala Phe Ile Met Pro Val Leu Ile
            245                 250                 255

Ile Thr Val Cys Tyr Gly Leu Met Ile Leu Arg Leu Lys Ser Val Arg
        260                 265                 270

Asn Ile Phe Glu Met Leu Arg Ile Asp Glu Gly Leu Arg Leu Lys Ile
    275                 280                 285

Tyr Lys Asp Thr Glu Gly Tyr Tyr Thr Ile Gly Ile Gly His Leu Leu
290                 295                 300

Thr Lys Ser Pro Ser Leu Asn Ala Ala Lys Ser Glu Leu Asp Lys Ala
305                 310                 315                 320

Ile Gly Arg Asn Thr Asn Gly Val Ile Thr Lys Asp Glu Ala Glu Lys
            325                 330                 335

Leu Phe Asn Gln Asp Val Asp Ala Ala Val Arg Gly Ile Leu Arg Asn
        340                 345                 350

Ala Lys Leu Lys Pro Val Tyr Asp Ser Leu Asp Ala Val Arg Arg Ala
    355                 360                 365

Ala Leu Ile Asn Met Val Phe Gln Met Gly Glu Thr Gly Val Ala Gly
370                 375                 380

Phe Thr Asn Ser Leu Arg Met Leu Gln Gln Lys Arg Trp Asp Glu Ala
385                 390                 395                 400

Ala Val Asn Leu Ala Lys Ser Arg Trp Tyr Asn Gln Thr Pro Asn Arg
            405                 410                 415

Ala Lys Arg Val Ile Thr Thr Phe Arg Thr Gly Thr Trp Asp Ala Tyr
        420                 425                 430

Glu Lys Asp Arg Asn Leu Arg Arg Ile Thr Arg Met Val Leu Val Val
    435                 440                 445

Val Ala Val Phe Ile Val Cys Trp Thr Pro Ile His Ile Tyr Val Ile
450                 455                 460

Ile Lys Ala Leu Val Thr Ile Pro Glu Thr Thr Phe Gln Thr Val Ser
465                 470                 475                 480

Trp His Phe Cys Ile Ala Leu Gly Tyr Thr Asn Ser Cys Leu Asn Pro
            485                 490                 495

Val Leu Tyr Ala Phe Leu Asp Glu Asn Phe Lys Arg Cys Phe Arg Glu
        500                 505                 510

Phe Cys Ile Pro Thr Ser Ser Asn Ile Glu Gln Gln Asn Ser Thr Arg
    515                 520                 525

Ile Arg Gln Asn Thr Arg Asp His Pro Ser Thr Ala Asn Thr Val Asp
530                 535                 540

Arg Thr Asn His Gln Leu Glu Asn Leu Glu Ala Glu Thr Ala Pro Leu
545                 550                 555                 560

Pro

<210> SEQ ID NO 26
<211> LENGTH: 542
<212> TYPE: PRT
<213> ORGANISM: Artificial Sequence
<220> FEATURE:
<223> OTHER INFORMATION: synthetic polypeptide

<400> SEQUENCE: 26

Asp Tyr Lys Asp Asp Ala Met Asp Ser Pro Ile Gln Ile Phe Arg
1               5                   10                  15

Gly Glu Pro Gly Pro Thr Cys Ala Pro Ser Ala Cys Leu Pro Pro Asn
            20                  25                  30

-continued

Ser Ser Ala Trp Phe Pro Gly Trp Ala Glu Pro Asp Ser Asn Gly Ser
         35                      40                      45

Ala Gly Ser Glu Asp Ala Gln Leu Glu Pro Ala His Ile Ser Pro Ala
 50                      55                      60

Ile Pro Val Ile Ile Thr Ala Val Tyr Ser Val Phe Val Val Gly
 65                      70                      75                      80

Leu Val Gly Asn Ser Leu Val Met Phe Val Ile Arg Tyr Thr Lys
                 85                      90                      95

Met Lys Thr Ala Thr Asn Ile Tyr Ile Phe Asn Leu Ala Leu Ala Asp
             100                     105                     110

Ala Leu Val Thr Thr Thr Met Pro Phe Gln Ser Thr Val Tyr Leu Met
             115                     120                     125

Asn Ser Trp Pro Phe Gly Asp Val Leu Cys Lys Ile Val Ile Ser Ile
 130                     135                     140

Asp Tyr Tyr Asn Met Phe Thr Ser Ile Phe Thr Leu Thr Met Met Ser
145                     150                     155                     160

Val Asp Arg Tyr Ile Ala Val Cys His Pro Val Lys Ala Leu Asp Phe
                165                     170                     175

Arg Thr Pro Leu Lys Ala Lys Ile Ile Asn Ile Cys Ile Trp Leu Leu
             180                     185                     190

Ser Ser Ser Val Gly Ile Ser Ala Ile Val Leu Gly Gly Thr Lys Val
             195                     200                     205

Arg Glu Asp Val Asp Val Ile Glu Cys Ser Leu Gln Phe Pro Asp Asp
         210                     215                     220

Asp Tyr Ser Trp Trp Asp Leu Phe Met Lys Ile Cys Val Phe Ile Phe
225                     230                     235                     240

Ala Phe Val Ile Pro Val Leu Ile Ile Val Cys Tyr Thr Leu Met
                245                     250                     255

Ile Leu Arg Leu Lys Ser Val Arg Leu Asn Ile Phe Glu Met Leu Arg
             260                     265                     270

Ile Asp Glu Gly Leu Arg Leu Lys Ile Tyr Lys Asp Thr Glu Gly Tyr
         275                     280                     285

Tyr Thr Ile Gly Ile Gly His Leu Leu Thr Lys Ser Pro Ser Leu Asn
 290                     295                     300

Ala Ala Lys Ser Glu Leu Asp Lys Ala Ile Gly Arg Asn Thr Asn Gly
305                     310                     315                     320

Val Ile Thr Lys Asp Glu Ala Glu Lys Leu Phe Asn Gln Asp Val Asp
                325                     330                     335

Ala Ala Val Arg Gly Ile Leu Arg Asn Ala Lys Leu Lys Pro Val Tyr
             340                     345                     350

Asp Ser Leu Asp Ala Val Arg Arg Ala Leu Ile Asn Met Val Phe
             355                     360                     365

Gln Met Gly Glu Thr Gly Val Ala Gly Phe Thr Asn Ser Leu Arg Met
         370                     375                     380

Leu Gln Gln Lys Arg Trp Asp Glu Ala Val Asn Leu Ala Lys Ser
385                     390                     395                     400

Arg Trp Tyr Asn Gln Thr Pro Asn Arg Ala Lys Arg Val Ile Thr Thr
                405                     410                     415

Phe Arg Thr Gly Thr Trp Asp Ala Tyr Glu Lys Asp Arg Asn Leu Arg
             420                     425                     430

Arg Ile Thr Arg Leu Val Leu Val Val Ala Val Phe Val Val Cys
             435                     440                     445

Trp Thr Pro Ile His Ile Phe Ile Leu Val Glu Ala Leu Gly Ser Thr

```
                          450                 455                 460
Ser His Ser Thr Ala Ala Leu Ser Ser Tyr Tyr Phe Cys Ile Ala Leu
465                 470                 475                 480

Gly Tyr Thr Asn Ser Ser Leu Asn Pro Ile Leu Tyr Ala Phe Leu Asp
                    485                 490                 495

Glu Asn Phe Lys Arg Cys Phe Arg Asp Phe Cys Phe Pro Leu Lys Met
                500                 505                 510

Arg Met Glu Arg Gln Ser Thr Ser Arg Val Arg Asn Thr Val Gln Asp
            515                 520                 525

Pro Ala Tyr Leu Arg Asp Ile Asp Gly Met Asn Lys Pro Val
        530                 535                 540

<210> SEQ ID NO 27
<211> LENGTH: 533
<212> TYPE: PRT
<213> ORGANISM: Artificial Sequence
<220> FEATURE:
<223> OTHER INFORMATION: synthetic polypeptide

<400> SEQUENCE: 27

Asp Tyr Lys Asp Asp Ala Met Glu Pro Ala Pro Ser Ala Gly Ala
1               5                   10                  15

Glu Leu Gln Pro Pro Leu Phe Ala Asn Ala Ser Asp Ala Tyr Pro Ser
                20                  25                  30

Ala Phe Pro Ser Ala Gly Ala Asn Ala Ser Gly Pro Pro Gly Ala Arg
                35                  40                  45

Ser Ala Ser Ser Leu Ala Leu Ala Ile Ala Ile Thr Ala Leu Tyr Ser
        50                  55                  60

Ala Val Cys Ala Val Gly Leu Leu Gly Asn Val Leu Val Met Phe Gly
65                  70                  75                  80

Ile Val Arg Tyr Thr Lys Met Lys Thr Ala Thr Asn Ile Tyr Ile Phe
                85                  90                  95

Asn Leu Ala Leu Ala Asp Ala Leu Ala Thr Ser Thr Leu Pro Phe Gln
                100                 105                 110

Ser Ala Lys Tyr Leu Met Glu Thr Trp Pro Phe Gly Glu Leu Leu Cys
            115                 120                 125

Lys Ala Val Leu Ser Ile Asp Tyr Tyr Asn Met Phe Thr Ser Ile Phe
130                 135                 140

Thr Leu Thr Met Met Ser Val Asp Arg Tyr Ile Ala Val Cys His Pro
145                 150                 155                 160

Val Lys Ala Leu Asp Phe Arg Thr Pro Ala Lys Ala Lys Leu Ile Asn
                165                 170                 175

Ile Cys Ile Trp Val Leu Ala Ser Gly Val Gly Val Pro Ile Met Val
                180                 185                 190

Met Ala Val Thr Arg Pro Arg Asp Gly Ala Val Val Cys Met Leu Gln
            195                 200                 205

Phe Pro Ser Pro Ser Trp Tyr Trp Asp Thr Val Thr Lys Ile Cys Val
210                 215                 220

Phe Leu Phe Ala Phe Val Val Pro Ile Leu Ile Ile Thr Val Cys Tyr
225                 230                 235                 240

Gly Leu Met Leu Leu Arg Leu Arg Ser Val Arg Asn Ile Phe Glu Met
                245                 250                 255

Leu Arg Ile Asp Glu Gly Leu Arg Leu Lys Ile Tyr Lys Asp Thr Glu
                260                 265                 270

Gly Tyr Tyr Thr Ile Gly Ile Gly His Leu Leu Thr Lys Ser Pro Ser
            275                 280                 285
```

```
Leu Asn Ala Ala Lys Ser Glu Leu Asp Lys Ala Ile Gly Arg Asn Thr
    290                 295                 300

Asn Gly Val Ile Thr Lys Asp Glu Ala Glu Lys Leu Phe Asn Gln Asp
305                 310                 315                 320

Val Asp Ala Ala Val Arg Gly Ile Leu Arg Asn Ala Lys Leu Lys Pro
                325                 330                 335

Val Tyr Asp Ser Leu Asp Ala Val Arg Arg Ala Ala Leu Ile Asn Met
                340                 345                 350

Val Phe Gln Met Gly Glu Thr Gly Val Ala Gly Phe Thr Asn Ser Leu
                355                 360                 365

Arg Met Leu Gln Gln Lys Arg Trp Asp Glu Ala Ala Val Asn Leu Ala
            370                 375                 380

Lys Ser Arg Trp Tyr Asn Gln Thr Pro Asn Arg Ala Lys Arg Val Ile
385                 390                 395                 400

Thr Thr Phe Arg Thr Gly Thr Trp Asp Ala Tyr Glu Lys Asp Arg Ser
                405                 410                 415

Leu Arg Arg Ile Thr Arg Met Val Leu Val Val Gly Ala Phe Val
                420                 425                 430

Val Cys Trp Ala Pro Ile His Ile Phe Val Ile Val Trp Thr Leu Val
            435                 440                 445

Asp Ile Asp Arg Arg Asp Pro Leu Val Val Ala Ala Leu His Leu Cys
    450                 455                 460

Ile Ala Leu Gly Tyr Ala Asn Ser Ser Leu Asn Pro Val Leu Tyr Ala
465                 470                 475                 480

Phe Leu Asp Glu Asn Phe Lys Arg Cys Phe Arg Gln Leu Cys Arg Lys
                485                 490                 495

Pro Cys Gly Arg Pro Asp Pro Ser Ser Phe Ser Arg Ala Arg Glu Ala
                500                 505                 510

Thr Ala Arg Glu Arg Val Thr Ala Cys Thr Pro Ser Asp Gly Pro Gly
            515                 520                 525

Gly Gly Ala Ala Ala
    530

<210> SEQ ID NO 28
<211> LENGTH: 530
<212> TYPE: PRT
<213> ORGANISM: Artificial Sequence
<220> FEATURE:
<223> OTHER INFORMATION: synthetic polypeptide

<400> SEQUENCE: 28

Asp Tyr Lys Asp Asp Asp Ala Met Asp Met Ala Asp Glu Pro Leu Asn
1               5                   10                  15

Gly Ser His Thr Trp Leu Ser Ile Pro Phe Asp Leu Asn Gly Ser Val
                20                  25                  30

Val Ser Thr Asn Thr Ser Asn Gln Thr Glu Pro Tyr Tyr Asp Leu Thr
            35                  40                  45

Ser Asn Ala Val Leu Thr Phe Ile Tyr Phe Val Val Cys Ile Ile Gly
        50                  55                  60

Leu Cys Gly Asn Thr Leu Val Ile Tyr Val Ile Leu Arg Tyr Ala Lys
65                  70                  75                  80

Met Lys Thr Ile Thr Asn Ile Tyr Ile Leu Asn Leu Ala Ile Ala Asp
                85                  90                  95

Glu Leu Phe Met Leu Gly Leu Pro Phe Leu Ala Met Gln Val Ala Leu
                100                 105                 110
```

-continued

```
Val His Trp Pro Phe Gly Lys Ala Ile Cys Arg Val Val Met Thr Val
    115                 120                 125

Asp Gly Ile Asn Gln Phe Thr Ser Ile Phe Cys Leu Thr Val Met Ser
130                 135                 140

Ile Asp Arg Tyr Leu Ala Val Val His Pro Ile Lys Ser Ala Lys Trp
145                 150                 155                 160

Arg Arg Pro Arg Thr Ala Lys Met Ile Thr Met Ala Val Trp Gly Val
                165                 170                 175

Ser Leu Leu Val Ile Leu Pro Ile Met Ile Tyr Ala Gly Leu Arg Ser
            180                 185                 190

Asn Gln Trp Gly Arg Ser Ser Cys Thr Ile Asn Trp Pro Gly Glu Ser
        195                 200                 205

Gly Ala Trp Tyr Thr Gly Phe Ile Ile Tyr Thr Phe Ile Leu Gly Phe
    210                 215                 220

Leu Val Pro Leu Thr Ile Ile Cys Leu Cys Tyr Leu Phe Ile Ile Ile
225                 230                 235                 240

Lys Val Lys Ser Ser Gly Asn Ile Phe Glu Met Leu Arg Ile Asp Glu
                245                 250                 255

Gly Leu Arg Leu Lys Ile Tyr Lys Asp Thr Glu Gly Tyr Tyr Thr Ile
            260                 265                 270

Gly Ile Gly His Leu Leu Thr Lys Ser Pro Ser Leu Asn Ala Ala Lys
        275                 280                 285

Ser Glu Leu Asp Lys Ala Ile Gly Arg Asn Thr Asn Gly Val Ile Thr
    290                 295                 300

Lys Asp Glu Ala Glu Lys Leu Phe Asn Gln Asp Val Asp Ala Ala Val
305                 310                 315                 320

Arg Gly Ile Leu Arg Asn Ala Lys Leu Lys Pro Val Tyr Asp Ser Leu
                325                 330                 335

Asp Ala Val Arg Arg Ala Ala Leu Ile Asn Met Val Phe Gln Met Gly
            340                 345                 350

Glu Thr Gly Val Ala Gly Phe Thr Asn Ser Leu Arg Met Leu Gln Gln
    355                 360                 365

Lys Arg Trp Asp Glu Ala Ala Val Asn Leu Ala Lys Ser Arg Trp Tyr
370                 375                 380

Asn Gln Thr Pro Asn Arg Ala Lys Arg Val Ile Thr Thr Phe Arg Thr
385                 390                 395                 400

Gly Thr Trp Asp Ala Tyr Lys Arg Lys Lys Ser Glu Lys Lys Val Thr
                405                 410                 415

Arg Met Val Ser Ile Val Val Ala Phe Ile Phe Cys Trp Leu Pro
            420                 425                 430

Phe Tyr Ile Phe Asn Val Ser Ser Val Ser Met Ala Ile Ser Pro Thr
    435                 440                 445

Pro Ala Leu Lys Gly Met Phe Asp Phe Val Val Val Leu Thr Tyr Ala
    450                 455                 460

Asn Ser Cys Ala Asn Pro Ile Leu Tyr Ala Phe Leu Ser Asp Asn Phe
465                 470                 475                 480

Lys Lys Ser Phe Gln Asn Val Leu Cys Leu Val Lys Val Ser Gly Thr
                485                 490                 495

Asp Asp Gly Glu Arg Ser Asp Ser Lys Gln Asp Lys Ser Arg Leu Asn
            500                 505                 510

Glu Thr Thr Glu Thr Gln Arg Thr Leu Leu Asn Gly Asp Leu Gln Thr
    515                 520                 525

Ser Ile
530
```

<210> SEQ ID NO 29
<211> LENGTH: 526
<212> TYPE: PRT
<213> ORGANISM: Artificial Sequence
<220> FEATURE:
<223> OTHER INFORMATION: synthetic polypeptide

<400> SEQUENCE: 29

```
Asp Tyr Lys Asp Asp Asp Ala Met Glu Pro Leu Phe Pro Ala Ser Thr
 1               5                  10                  15

Pro Ser Trp Asn Ala Ser Ser Pro Gly Ala Ala Ser Gly Gly Gly Asp
                20                  25                  30

Asn Arg Thr Leu Val Gly Pro Ala Pro Ser Ala Gly Ala Arg Ala Val
            35                  40                  45

Leu Val Pro Val Leu Tyr Leu Leu Val Cys Ala Ala Gly Leu Gly Gly
        50                  55                  60

Asn Thr Leu Val Ile Tyr Val Val Leu Arg Phe Ala Lys Met Lys Thr
65                  70                  75                  80

Val Thr Asn Ile Tyr Ile Leu Asn Leu Ala Val Ala Asp Val Leu Tyr
                85                  90                  95

Met Leu Gly Leu Pro Phe Leu Ala Thr Gln Asn Ala Ala Ser Phe Trp
            100                 105                 110

Pro Phe Gly Pro Val Leu Cys Arg Leu Val Met Thr Leu Asp Gly Val
        115                 120                 125

Asn Gln Phe Thr Ser Val Phe Cys Leu Thr Val Met Ser Val Asp Arg
130                 135                 140

Tyr Leu Ala Val Val His Pro Leu Ser Ser Ala Arg Trp Arg Arg Pro
145                 150                 155                 160

Arg Val Ala Lys Leu Ala Ser Ala Ala Ala Trp Val Leu Ser Leu Cys
                165                 170                 175

Met Ser Leu Pro Leu Leu Val Phe Ala Asp Val Gln Glu Gly Gly Thr
            180                 185                 190

Cys Asn Ala Ser Trp Pro Glu Pro Val Gly Leu Trp Gly Ala Val Phe
        195                 200                 205

Ile Ile Tyr Thr Ala Val Leu Gly Phe Phe Ala Pro Leu Leu Val Ile
    210                 215                 220

Cys Leu Cys Tyr Leu Leu Ile Val Val Lys Val Arg Ala Ala Gly Asn
225                 230                 235                 240

Ile Phe Glu Met Leu Arg Ile Asp Glu Gly Leu Arg Leu Lys Ile Tyr
                245                 250                 255

Lys Asp Thr Glu Gly Tyr Tyr Thr Ile Gly Ile Gly His Leu Leu Thr
            260                 265                 270

Lys Ser Pro Ser Leu Asn Ala Ala Lys Ser Glu Leu Asp Lys Ala Ile
        275                 280                 285

Gly Arg Asn Thr Asn Gly Val Ile Thr Lys Asp Glu Ala Glu Lys Leu
    290                 295                 300

Phe Asn Gln Asp Val Asp Ala Ala Val Arg Gly Ile Leu Arg Asn Ala
305                 310                 315                 320

Lys Leu Lys Pro Val Tyr Asp Ser Leu Asp Ala Val Arg Arg Ala Ala
                325                 330                 335

Leu Ile Asn Met Val Phe Gln Met Gly Glu Thr Gly Val Ala Gly Phe
            340                 345                 350

Thr Asn Ser Leu Arg Met Leu Gln Gln Lys Arg Trp Asp Glu Ala Ala
        355                 360                 365
```

```
Val Asn Leu Ala Lys Ser Arg Trp Tyr Asn Gln Thr Pro Asn Arg Ala
        370                 375                 380

Lys Arg Val Ile Thr Thr Phe Arg Thr Gly Thr Trp Asp Ala Tyr Val
385                 390                 395                 400

Arg Arg Arg Ser Glu Arg Lys Val Thr Arg Met Val Leu Val Val Val
                405                 410                 415

Leu Val Phe Ala Gly Cys Trp Leu Pro Phe Phe Thr Val Asn Ile Val
            420                 425                 430

Asn Leu Ala Val Ala Leu Pro Gln Glu Pro Ala Ser Ala Gly Leu Tyr
        435                 440                 445

Phe Phe Val Val Ile Leu Ser Tyr Ala Asn Ser Cys Ala Asn Pro Val
    450                 455                 460

Leu Tyr Gly Phe Leu Ser Asp Asn Phe Arg Gln Ser Phe Gln Lys Val
465                 470                 475                 480

Leu Cys Leu Arg Lys Gly Ser Gly Ala Lys Asp Ala Asp Ala Thr Glu
                485                 490                 495

Pro Arg Pro Asp Arg Ile Arg Gln Gln Glu Ala Thr Pro Pro Ala
            500                 505                 510

His Arg Ala Ala Ala Asn Gly Leu Met Gln Thr Ser Lys Leu
        515                 520                 525

<210> SEQ ID NO 30
<211> LENGTH: 523
<212> TYPE: PRT
<213> ORGANISM: Artificial Sequence
<220> FEATURE:
<223> OTHER INFORMATION: synthetic polypeptide

<400> SEQUENCE: 30

Asp Tyr Lys Asp Asp Ala Met Ile Leu Asn Ser Thr Glu Asp
1               5                   10                  15

Gly Ile Lys Arg Ile Gln Asp Asp Cys Pro Lys Ala Gly Arg His Asn
            20                  25                  30

Tyr Ile Phe Val Met Ile Pro Thr Leu Tyr Ser Ile Ile Phe Val Val
        35                  40                  45

Gly Ile Phe Gly Asn Ser Leu Val Val Ile Val Ile Tyr Phe Tyr Met
    50                  55                  60

Lys Leu Lys Thr Val Ala Ser Val Phe Leu Leu Asn Leu Ala Leu Ala
65                  70                  75                  80

Asp Leu Cys Phe Leu Leu Thr Leu Pro Leu Trp Ala Val Tyr Thr Ala
                85                  90                  95

Met Glu Tyr Arg Trp Pro Phe Gly Asn Tyr Leu Cys Lys Ile Ala Ser
            100                 105                 110

Ala Ser Val Ser Phe Asn Leu Tyr Ala Ser Val Phe Leu Leu Thr Cys
        115                 120                 125

Leu Ser Ile Asp Arg Tyr Leu Ala Ile Val His Pro Met Lys Ser Arg
    130                 135                 140

Leu Arg Arg Thr Met Leu Val Ala Lys Val Thr Cys Ile Ile Ile Trp
145                 150                 155                 160

Leu Leu Ala Gly Leu Ala Ser Leu Pro Ala Ile Ile His Arg Asn Val
                165                 170                 175

Phe Phe Ile Glu Asn Thr Asn Ile Thr Val Cys Ala Phe His Tyr Glu
            180                 185                 190

Ser Gln Asn Ser Thr Leu Pro Ile Gly Leu Gly Leu Thr Lys Asn Ile
        195                 200                 205

Leu Gly Phe Leu Phe Pro Phe Leu Ile Ile Leu Thr Ser Tyr Thr Leu
```

```
                210                 215                 220
Ile Trp Lys Ala Leu Lys Lys Ala Tyr Asn Ile Phe Glu Met Leu Arg
225                 230                 235                 240

Ile Asp Glu Gly Leu Arg Leu Lys Ile Tyr Lys Asp Thr Glu Gly Tyr
                245                 250                 255

Tyr Thr Ile Gly Ile Gly His Leu Leu Thr Lys Ser Pro Ser Leu Asn
                260                 265                 270

Ala Ala Lys Ser Glu Leu Asp Lys Ala Ile Gly Arg Asn Thr Asn Gly
                275                 280                 285

Val Ile Thr Lys Asp Glu Ala Glu Lys Leu Phe Asn Gln Asp Val Asp
290                 295                 300

Ala Ala Val Arg Gly Ile Leu Arg Asn Ala Lys Leu Lys Pro Val Tyr
305                 310                 315                 320

Asp Ser Leu Asp Ala Val Arg Arg Ala Ala Leu Ile Asn Met Val Phe
                325                 330                 335

Gln Met Gly Glu Thr Gly Val Ala Gly Phe Thr Asn Ser Leu Arg Met
                340                 345                 350

Leu Gln Gln Lys Arg Trp Asp Glu Ala Ala Val Asn Leu Ala Lys Ser
                355                 360                 365

Arg Trp Tyr Asn Gln Thr Pro Asn Arg Ala Lys Arg Val Ile Thr Thr
370                 375                 380

Phe Arg Thr Gly Thr Trp Asp Ala Tyr Lys Asn Lys Pro Arg Asn Asp
385                 390                 395                 400

Asp Ile Phe Lys Ile Ile Met Ala Ile Val Leu Phe Phe Phe Phe Ser
                405                 410                 415

Trp Ile Pro His Gln Ile Phe Thr Phe Leu Asp Val Leu Ile Gln Leu
                420                 425                 430

Gly Ile Ile Arg Asp Cys Arg Ile Ala Asp Ile Val Asp Thr Ala Met
                435                 440                 445

Pro Ile Thr Ile Cys Ile Ala Tyr Phe Asn Asn Cys Leu Asn Pro Leu
450                 455                 460

Phe Tyr Gly Phe Leu Gly Lys Lys Phe Lys Arg Tyr Phe Leu Gln Leu
465                 470                 475                 480

Leu Lys Tyr Ile Pro Pro Lys Ala Lys Ser His Ser Asn Leu Ser Thr
                485                 490                 495

Lys Met Ser Thr Leu Ser Tyr Arg Pro Ser Asp Asn Val Ser Ser Ser
                500                 505                 510

Thr Lys Lys Pro Ala Pro Cys Phe Glu Val Glu
                515                 520
```

<210> SEQ ID NO 31
<211> LENGTH: 519
<212> TYPE: PRT
<213> ORGANISM: Artificial Sequence
<220> FEATURE:
<223> OTHER INFORMATION: synthetic polypeptide

<400> SEQUENCE: 31

```
Asp Tyr Lys Asp Asp Asp Ala Met Asn Thr Thr Ser Ser Ala Ala Pro
1               5                   10                  15

Pro Ser Leu Gly Val Glu Phe Ile Ser Leu Leu Ala Ile Ile Leu Leu
                20                  25                  30

Ser Val Ala Leu Ala Val Gly Leu Pro Gly Asn Ser Phe Val Val Trp
            35                  40                  45

Ser Ile Leu Lys Arg Met Gln Lys Arg Ser Val Thr Ala Leu Met Val
        50                  55                  60
```

```
Leu Asn Leu Ala Leu Ala Asp Leu Ala Val Leu Leu Thr Ala Pro Phe
 65                  70                  75                  80

Phe Leu His Phe Leu Ala Gln Gly Thr Trp Ser Phe Gly Leu Ala Gly
             85                  90                  95

Cys Arg Leu Cys His Tyr Val Cys Gly Val Ser Met Tyr Ala Ser Val
            100                 105                 110

Leu Leu Ile Thr Ala Met Ser Leu Asp Arg Ser Leu Ala Val Ala Arg
        115                 120                 125

Pro Phe Val Ser Gln Lys Leu Arg Thr Lys Ala Met Ala Arg Arg Val
    130                 135                 140

Leu Ala Gly Ile Trp Val Leu Ser Phe Leu Leu Ala Thr Pro Val Leu
145                 150                 155                 160

Ala Tyr Arg Thr Val Val Pro Trp Lys Thr Asn Met Ser Leu Cys Phe
                165                 170                 175

Pro Arg Tyr Pro Ser Glu Gly His Arg Ala Phe His Leu Ile Phe Glu
            180                 185                 190

Ala Val Thr Gly Phe Leu Leu Pro Phe Leu Ala Val Val Ala Ser Tyr
        195                 200                 205

Ser Asp Ile Gly Arg Arg Leu Gln Ala Arg Arg Asn Ile Phe Glu Met
    210                 215                 220

Leu Arg Ile Asp Glu Gly Leu Arg Leu Lys Ile Tyr Lys Asp Thr Glu
225                 230                 235                 240

Gly Tyr Tyr Thr Ile Gly Ile Gly His Leu Leu Thr Lys Ser Pro Ser
                245                 250                 255

Leu Asn Ala Ala Lys Ser Glu Leu Asp Lys Ala Ile Gly Arg Asn Thr
            260                 265                 270

Asn Gly Val Ile Thr Lys Asp Glu Ala Glu Lys Leu Phe Asn Gln Asp
        275                 280                 285

Val Asp Ala Ala Val Arg Gly Ile Leu Arg Asn Ala Lys Leu Lys Pro
    290                 295                 300

Val Tyr Asp Ser Leu Asp Ala Val Arg Arg Ala Ala Leu Ile Asn Met
305                 310                 315                 320

Val Phe Gln Met Gly Glu Thr Gly Val Ala Gly Phe Thr Asn Ser Leu
                325                 330                 335

Arg Met Leu Gln Gln Lys Arg Trp Asp Glu Ala Val Asn Leu Ala
            340                 345                 350

Lys Ser Arg Trp Tyr Asn Gln Thr Pro Asn Arg Ala Lys Arg Val Ile
        355                 360                 365

Thr Thr Phe Arg Thr Gly Thr Trp Asp Ala Tyr Phe Arg Arg Ser Arg
    370                 375                 380

Arg Thr Gly Arg Leu Val Val Leu Ile Ile Leu Thr Phe Ala Ala Phe
385                 390                 395                 400

Trp Leu Pro Tyr His Val Val Asn Leu Ala Glu Ala Gly Arg Ala Leu
                405                 410                 415

Ala Gly Gln Ala Ala Gly Leu Gly Leu Val Gly Lys Arg Leu Ser Leu
            420                 425                 430

Ala Arg Asn Val Leu Ile Ala Leu Ala Phe Leu Ser Ser Ser Val Asn
        435                 440                 445

Pro Val Leu Tyr Ala Cys Ala Gly Gly Leu Leu Arg Ser Ala Gly
    450                 455                 460

Val Gly Phe Val Ala Lys Leu Leu Glu Gly Thr Gly Ser Glu Ala Ser
465                 470                 475                 480

Ser Thr Arg Arg Gly Gly Ser Leu Gly Gln Thr Ala Arg Ser Gly Pro
```

```
                         485                 490                 495
Ala Ala Leu Glu Pro Gly Pro Ser Glu Ser Leu Thr Ala Ser Ser Pro
                     500                 505                 510

Leu Lys Leu Asn Glu Leu Asn
            515

<210> SEQ ID NO 32
<211> LENGTH: 1047
<212> TYPE: PRT
<213> ORGANISM: Artificial Sequence
<220> FEATURE:
<223> OTHER INFORMATION: synthetic polypeptide

<400> SEQUENCE: 32

Asp Tyr Lys Asp Asp Ala Lys Pro Lys Gly His Pro His Met Asn
 1               5                  10                  15

Ser Ile Arg Ile Asp Gly Asp Ile Thr Leu Gly Gly Leu Phe Pro Val
                20                  25                  30

His Gly Arg Gly Ser Glu Gly Lys Pro Cys Gly Glu Leu Lys Lys Glu
            35                  40                  45

Lys Gly Ile His Arg Leu Glu Ala Met Leu Phe Ala Leu Asp Arg Ile
 50                  55                  60

Asn Asn Asp Pro Asp Leu Leu Pro Asn Ile Thr Leu Gly Ala Arg Ile
65                  70                  75                  80

Leu Asp Thr Cys Ser Arg Asp Thr His Ala Leu Glu Gln Ser Leu Thr
                85                  90                  95

Phe Val Gln Ala Leu Ile Glu Lys Asp Gly Thr Glu Val Arg Cys Gly
            100                 105                 110

Ser Gly Gly Pro Pro Ile Ile Thr Lys Pro Glu Arg Val Val Gly Val
        115                 120                 125

Ile Gly Ala Ser Gly Ser Ser Val Ser Ile Met Val Ala Asn Ile Leu
    130                 135                 140

Arg Leu Phe Lys Ile Pro Gln Ile Ser Tyr Ala Ser Thr Ala Pro Asp
145                 150                 155                 160

Leu Ser Asp Asn Ser Arg Tyr Asp Phe Phe Ser Arg Val Val Pro Ser
                165                 170                 175

Asp Thr Tyr Gln Ala Gln Ala Met Val Asp Ile Val Arg Ala Leu Lys
            180                 185                 190

Trp Asn Tyr Val Ser Thr Val Ala Ser Glu Gly Ser Tyr Gly Glu Ser
        195                 200                 205

Gly Val Glu Ala Phe Ile Gln Lys Ser Arg Glu Asp Gly Gly Val Cys
    210                 215                 220

Ile Ala Gln Ser Val Lys Ile Pro Arg Glu Pro Lys Ala Gly Glu Phe
225                 230                 235                 240

Asp Lys Ile Ile Arg Arg Leu Leu Glu Thr Ser Asn Ala Arg Ala Val
                245                 250                 255

Ile Ile Phe Ala Asn Glu Asp Asp Ile Arg Arg Val Leu Glu Ala Ala
            260                 265                 270

Arg Arg Ala Asn Gln Thr Gly His Phe Phe Trp Met Gly Ser Asp Ser
        275                 280                 285

Trp Gly Ser Lys Ile Ala Pro Val Leu His Leu Glu Glu Val Ala Glu
    290                 295                 300

Gly Ala Val Thr Ile Leu Pro Lys Arg Met Ser Val Arg Gly Phe Asp
305                 310                 315                 320

Arg Tyr Phe Ser Ser Arg Thr Leu Asp Asn Asn Arg Arg Asn Ile Trp
                325                 330                 335
```

-continued

```
Phe Ala Glu Phe Trp Glu Asp Asn Phe His Cys Lys Leu Ser Arg His
            340                 345                 350
Ala Leu Lys Lys Gly Ser His Val Lys Cys Thr Asn Arg Glu Arg
        355                 360                 365
Ile Gly Gln Asp Ser Ala Tyr Glu Gln Glu Gly Lys Val Gln Phe Val
370                 375                 380
Ile Asp Ala Val Tyr Ala Met Gly His Ala Leu His Ala Met His Arg
385                 390                 395                 400
Asp Leu Cys Pro Gly Arg Val Gly Leu Cys Pro Arg Met Asp Pro Val
                405                 410                 415
Asp Gly Thr Gln Leu Leu Lys Tyr Ile Arg Asn Val Asn Phe Ser Gly
            420                 425                 430
Ile Ala Gly Asn Pro Val Thr Phe Asn Glu Asn Gly Asp Ala Pro Gly
        435                 440                 445
Arg Tyr Asp Ile Tyr Gln Tyr Gln Leu Arg Asn Asp Ser Ala Glu Tyr
    450                 455                 460
Lys Val Ile Gly Ser Trp Thr Asp His Leu His Leu Arg Ile Glu Arg
465                 470                 475                 480
Met His Trp Pro Gly Ser Gly Gln Gln Leu Pro Arg Ser Ile Cys Ser
                485                 490                 495
Leu Pro Cys Gln Pro Gly Glu Arg Lys Lys Thr Val Lys Gly Met Pro
            500                 505                 510
Cys Cys Trp His Cys Glu Pro Cys Thr Gly Tyr Gln Tyr Gln Val Asp
        515                 520                 525
Arg Tyr Thr Cys Lys Thr Cys Pro Tyr Asp Met Arg Pro Thr Glu Asn
    530                 535                 540
Arg Thr Gly Cys Arg Pro Ile Pro Ile Ile Lys Leu Glu Trp Gly Ser
545                 550                 555                 560
Pro Trp Ala Val Leu Pro Leu Phe Leu Ala Val Val Gly Ile Ala Ala
                565                 570                 575
Thr Leu Phe Val Val Ile Thr Phe Val Arg Tyr Asn Asp Thr Pro Ile
            580                 585                 590
Val Lys Ala Ser Gly Arg Glu Leu Ser Tyr Val Leu Leu Ala Gly Ile
        595                 600                 605
Phe Leu Cys Tyr Ala Thr Thr Phe Leu Met Ile Ala Glu Pro Asp Leu
    610                 615                 620
Gly Thr Cys Ser Leu Arg Arg Ile Phe Leu Gly Leu Gly Met Ser Ile
625                 630                 635                 640
Ser Tyr Ala Ala Leu Leu Thr Lys Thr Asn Arg Ile Tyr Arg Ile Phe
                645                 650                 655
Glu Gln Gly Lys Arg Ser Val Ser Ala Pro Arg Phe Ile Ser Pro Ala
            660                 665                 670
Ser Gln Leu Ala Ile Thr Phe Ser Leu Ile Ser Leu Gln Leu Leu Gly
        675                 680                 685
Ile Cys Val Trp Phe Val Val Asp Pro Ser His Ser Val Val Asp Phe
    690                 695                 700
Gln Asp Gln Arg Thr Leu Asp Pro Arg Phe Ala Arg Gly Val Leu Lys
705                 710                 715                 720
Cys Asp Ile Ser Asp Leu Ser Leu Ile Cys Leu Leu Gly Tyr Ser Met
                725                 730                 735
Leu Leu Met Val Thr Cys Thr Val Tyr Ala Ile Lys Thr Arg Gly Val
            740                 745                 750
Pro Glu Asn Ile Phe Glu Met Leu Arg Ile Asp Glu Gly Leu Arg Leu
```

```
                    755                 760                 765
Lys Ile Tyr Lys Asp Thr Glu Gly Tyr Thr Ile Gly Ile Gly His
    770                 775                 780

Leu Leu Thr Lys Ser Pro Ser Leu Asn Ala Ala Lys Ser Glu Leu Asp
785                 790                 795                 800

Lys Ala Ile Gly Arg Asn Thr Asn Gly Val Ile Thr Lys Asp Glu Ala
                805                 810                 815

Glu Lys Leu Phe Asn Gln Asp Val Asp Ala Ala Val Arg Gly Ile Leu
            820                 825                 830

Arg Asn Ala Lys Leu Lys Pro Val Tyr Asp Ser Leu Asp Ala Val Arg
        835                 840                 845

Arg Ala Ala Leu Ile Asn Met Val Phe Gln Met Gly Glu Thr Gly Val
    850                 855                 860

Ala Gly Phe Thr Asn Ser Leu Arg Met Leu Gln Gln Lys Arg Trp Asp
865                 870                 875                 880

Glu Ala Ala Val Asn Leu Ala Lys Ser Arg Trp Tyr Asn Gln Thr Pro
                885                 890                 895

Asn Arg Ala Lys Arg Val Ile Thr Thr Phe Arg Thr Gly Thr Trp Asp
            900                 905                 910

Ala Tyr Thr Phe Asn Glu Ala Lys Pro Ile Gly Phe Thr Met Tyr Thr
        915                 920                 925

Thr Cys Ile Val Trp Leu Ala Phe Ile Pro Ile Phe Gly Thr Ser
    930                 935                 940

Gln Ser Ala Asp Lys Leu Tyr Ile Gln Thr Thr Thr Leu Thr Val Ser
945                 950                 955                 960

Val Ser Leu Ser Ala Ser Val Ser Leu Gly Met Leu Tyr Met Pro Lys
                965                 970                 975

Val Tyr Ile Ile Leu Phe His Pro Glu Gln Asn Val Pro Lys Arg Lys
            980                 985                 990

Arg Ser Leu Lys Ala Val Val Thr Ala Ala Thr Met Ser Asn Lys Phe
        995                 1000                1005

Thr Gln Lys Gly Asn Phe Arg Pro Asn Gly Glu Ala Lys Ser Glu Leu
    1010                1015                1020

Cys Glu Asn Leu Glu Ala Pro Ala Leu Ala Thr Lys Gln Thr Tyr Val
1025                1030                1035                1040

Thr Tyr Thr Asn His Ala Ile
                1045

<210> SEQ ID NO 33
<211> LENGTH: 58
<212> TYPE: PRT
<213> ORGANISM: Bos taurus

<400> SEQUENCE: 33

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55

<210> SEQ ID NO 34
<211> LENGTH: 76
<212> TYPE: PRT
```

<213> ORGANISM: Bos taurus

<400> SEQUENCE: 34

Met Lys Ser Pro Glu Glu Leu Lys Gly Ile Phe Glu Lys Tyr Ala Ala
1               5                   10                  15

Lys Glu Gly Asp Pro Asn Gln Leu Ser Lys Glu Leu Lys Leu Leu
            20                  25                  30

Leu Gln Thr Glu Phe Pro Ser Leu Leu Lys Gly Pro Ser Thr Leu Asp
        35                  40                  45

Glu Leu Phe Glu Glu Leu Asp Lys Asn Gly Asp Gly Glu Val Ser Phe
    50                  55                  60

Glu Glu Phe Gln Val Leu Val Lys Lys Ile Ser Gln
65                  70                  75

<210> SEQ ID NO 35
<211> LENGTH: 111
<212> TYPE: PRT
<213> ORGANISM: Artificial Sequence
<220> FEATURE:
<223> OTHER INFORMATION: synthetic polypeptide

<400> SEQUENCE: 35

Met Ala Gln Val Ile Asn Thr Phe Asp Gly Val Ala Asp Tyr Leu Gln
1               5                   10                  15

Thr Tyr His Lys Leu Pro Asp Asn Tyr Ile Thr Lys Ser Glu Ala Gln
            20                  25                  30

Ala Leu Gly Trp Val Ala Ser Lys Gly Asn Leu Ala Asp Val Ala Pro
        35                  40                  45

Gly Lys Ser Ile Gly Gly Asp Ile Phe Ser Asn Arg Glu Gly Lys Leu
    50                  55                  60

Pro Gly Lys Ser Gly Arg Thr Trp Arg Glu Ala Asp Ile Asn Tyr Thr
65                  70                  75                  80

Ser Gly Phe Arg Asn Ser Asp Arg Ile Leu Tyr Ser Ser Asp Trp Leu
                85                  90                  95

Ile Tyr Lys Thr Thr Asp His Tyr Gln Thr Phe Thr Lys Ile Arg
            100                 105                 110

<210> SEQ ID NO 36
<211> LENGTH: 190
<212> TYPE: PRT
<213> ORGANISM: Trichoderma reesei

<400> SEQUENCE: 36

Glu Thr Ile Gln Pro Gly Thr Gly Tyr Asn Asn Gly Tyr Phe Tyr Ser
1               5                   10                  15

Tyr Trp Asn Asp Gly His Gly Gly Val Thr Tyr Thr Asn Gly Pro Gly
            20                  25                  30

Gly Gln Phe Ser Val Asn Trp Ser Asn Ser Gly Asn Phe Val Gly Gly
        35                  40                  45

Lys Gly Trp Gln Pro Gly Thr Lys Asn Lys Val Ile Asn Phe Ser Gly
    50                  55                  60

Ser Tyr Asn Pro Asn Gly Asn Ser Tyr Leu Ser Val Tyr Gly Trp Ser
65                  70                  75                  80

Arg Asn Pro Leu Ile Glu Tyr Tyr Ile Val Glu Asn Phe Gly Thr Tyr
                85                  90                  95

Asn Pro Ser Thr Gly Ala Thr Lys Leu Gly Glu Val Thr Ser Asp Gly
            100                 105                 110

Ser Val Tyr Asp Ile Tyr Arg Thr Gln Arg Val Asn Gln Pro Ser Ile

```
            115                 120                 125
Ile Gly Thr Ala Thr Phe Tyr Gln Tyr Trp Ser Val Arg Arg Asn His
    130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 37
<211> LENGTH: 455
<212> TYPE: PRT
<213> ORGANISM: Pyrococcus furiosus

<400> SEQUENCE: 37

Met Pro Thr Trp Glu Glu Leu Tyr Lys Asn Ala Ile Glu Lys Ala Ile
1               5                   10                  15

Lys Ser Val Pro Lys Val Lys Gly Val Leu Leu Gly Tyr Asn Thr Asn
                20                  25                  30

Ile Asp Ala Ile Lys Tyr Leu Asp Ser Lys Asp Leu Glu Glu Arg Ile
            35                  40                  45

Ile Lys Ala Gly Lys Glu Val Ile Lys Tyr Ser Glu Glu Leu Pro
        50                  55                  60

Asp Lys Ile Asn Thr Val Ser Gln Leu Leu Gly Ser Ile Leu Trp Ser
65                  70                  75                  80

Ile Arg Arg Gly Lys Ala Ala Glu Leu Phe Val Glu Ser Cys Pro Val
                85                  90                  95

Arg Phe Tyr Met Lys Arg Trp Gly Trp Asn Glu Leu Arg Met Gly Gly
                100                 105                 110

Gln Ala Gly Ile Met Ala Asn Leu Leu Gly Gly Val Tyr Gly Val Pro
            115                 120                 125

Val Ile Val His Val Pro Gln Leu Ser Arg Leu Gln Ala Asn Leu Phe
130                 135                 140

Leu Asp Gly Pro Ile Tyr Val Pro Thr Leu Glu Asn Gly Glu Val Lys
145                 150                 155                 160

Leu Ile His Pro Lys Glu Phe Ser Gly Asp Glu Glu Asn Cys Ile His
                165                 170                 175

Tyr Ile Tyr Glu Phe Pro Arg Gly Phe Arg Val Phe Glu Phe Glu Ala
            180                 185                 190

Pro Arg Glu Asn Arg Phe Ile Gly Ser Ala Asp Asp Tyr Asn Thr Thr
        195                 200                 205

Leu Phe Ile Arg Glu Glu Phe Arg Glu Ser Phe Ser Glu Val Ile Lys
    210                 215                 220

Asn Val Gln Leu Ala Ile Leu Ser Gly Leu Gln Ala Leu Thr Lys Glu
225                 230                 235                 240

Asn Tyr Lys Glu Pro Phe Glu Ile Val Lys Ser Asn Leu Glu Val Leu
                245                 250                 255

Asn Glu Arg Glu Ile Pro Val His Leu Glu Phe Ala Phe Thr Pro Asp
            260                 265                 270

Glu Lys Val Arg Glu Ile Leu Asn Val Leu Gly Met Phe Tyr Ser
        275                 280                 285

Val Gly Leu Asn Glu Val Glu Leu Ala Ser Ile Met Glu Ile Leu Gly
    290                 295                 300

Glu Lys Lys Leu Ala Lys Glu Leu Leu Ala His Asp Pro Val Asp Pro
```

```
                305                 310                 315                 320
Ile Ala Val Thr Glu Ala Met Leu Lys Leu Ala Lys Lys Thr Gly Val
                    325                 330                 335

Lys Arg Ile His Phe His Thr Tyr Gly Tyr Tyr Leu Ala Leu Thr Glu
                    340                 345                 350

Tyr Lys Gly Glu His Val Arg Asp Ala Leu Leu Phe Ala Ala Leu Ala
                    355                 360                 365

Ala Ala Ala Lys Ala Met Lys Gly Asn Ile Thr Ser Leu Glu Glu Ile
                    370                 375                 380

Arg Glu Ala Thr Ser Val Pro Val Asn Glu Lys Ala Thr Gln Val Glu
385                 390                 395                 400

Glu Lys Leu Arg Ala Glu Tyr Gly Ile Lys Glu Gly Ile Gly Glu Val
                    405                 410                 415

Glu Gly Tyr Gln Ile Ala Phe Ile Pro Thr Lys Ile Val Ala Lys Pro
                    420                 425                 430

Lys Ser Thr Val Gly Ile Gly Asp Thr Ile Ser Ser Ser Ala Phe Ile
                    435                 440                 445

Gly Glu Phe Ser Phe Thr Leu
            450                 455

<210> SEQ ID NO 38
<211> LENGTH: 565
<212> TYPE: PRT
<213> ORGANISM: Artificial Sequence
<220> FEATURE:
<223> OTHER INFORMATION: synthetic polypeptide

<400> SEQUENCE: 38

Asp Tyr Lys Asp Asp Ala Arg Arg Pro Glu Ser Lys Ala Thr Asn
1               5                   10                  15

Ala Thr Leu Asp Pro Arg Ser Phe Leu Leu Arg Asn Pro Asn Asp Lys
                20                  25                  30

Tyr Glu Pro Phe Trp Glu Asp Glu Lys Asn Glu Ser Gly Leu Thr
            35                  40                  45

Glu Tyr Arg Leu Val Ser Ile Asn Lys Ser Ser Pro Leu Gln Lys Gln
    50                  55                  60

Leu Pro Ala Phe Ile Ser Glu Asp Ala Ser Gly Tyr Leu Thr Ser Ser
65                  70                  75                  80

Trp Leu Thr Leu Phe Val Pro Ser Val Tyr Thr Gly Val Phe Val Val
                    85                  90                  95

Ser Leu Pro Leu Asn Ile Met Ala Ile Val Val Phe Ile Leu Lys Met
                    100                 105                 110

Lys Val Lys Lys Pro Ala Val Val Tyr Met Leu His Leu Ala Thr Ala
                    115                 120                 125

Asp Val Leu Phe Val Ser Val Leu Pro Phe Lys Ile Ser Tyr Tyr Phe
                    130                 135                 140

Ser Gly Ser Asp Trp Gln Phe Gly Ser Glu Leu Cys Arg Phe Val Thr
145                 150                 155                 160

Ala Ala Phe Tyr Cys Asn Met Tyr Ala Ser Ile Leu Leu Met Thr Val
                    165                 170                 175

Ile Ser Ile Asp Arg Phe Leu Ala Val Val Tyr Pro Met Gln Ser Leu
                    180                 185                 190

Ser Trp Arg Thr Leu Gly Arg Ala Ser Phe Thr Cys Leu Ala Ile Trp
                    195                 200                 205

Ala Leu Ala Ile Ala Gly Val Val Pro Leu Leu Leu Lys Glu Gln Thr
    210                 215                 220
```

```
Ile Gln Val Pro Gly Leu Asn Ile Thr Thr Cys His Asp Val Leu Asn
225                 230                 235                 240

Glu Thr Leu Leu Glu Gly Tyr Tyr Ala Tyr Tyr Phe Ser Ala Phe Ser
                245                 250                 255

Ala Val Phe Phe Phe Val Pro Leu Ile Ile Ser Thr Val Cys Tyr Val
            260                 265                 270

Ser Ile Ile Arg Cys Leu Ser Ser Ala Asn Ile Phe Glu Met Leu
        275                 280                 285

Arg Ile Asp Glu Gly Leu Arg Leu Lys Ile Tyr Lys Asp Thr Glu Gly
    290                 295                 300

Tyr Tyr Thr Ile Gly Ile Gly His Leu Leu Thr Lys Ser Pro Ser Leu
305                 310                 315                 320

Asn Ala Ala Lys Ser Glu Leu Asp Lys Ala Ile Gly Arg Asn Thr Asn
                325                 330                 335

Gly Val Ile Thr Lys Asp Glu Ala Glu Lys Leu Phe Asn Gln Asp Val
            340                 345                 350

Asp Ala Ala Val Arg Gly Ile Leu Arg Asn Ala Lys Leu Lys Pro Val
        355                 360                 365

Tyr Asp Ser Leu Asp Ala Val Arg Arg Ala Ala Leu Ile Asn Met Val
    370                 375                 380

Phe Gln Met Gly Glu Thr Gly Val Ala Gly Phe Thr Asn Ser Leu Arg
385                 390                 395                 400

Met Leu Gln Gln Lys Arg Trp Asp Glu Ala Ala Val Asn Leu Ala Lys
                405                 410                 415

Ser Arg Trp Tyr Asn Gln Thr Pro Asn Arg Ala Lys Arg Val Ile Thr
            420                 425                 430

Thr Phe Arg Thr Gly Thr Trp Asp Ala Tyr Ala Asn Arg Ser Lys Lys
        435                 440                 445

Ser Arg Ala Leu Phe Leu Ser Ala Ala Val Phe Cys Ile Phe Ile Ile
    450                 455                 460

Cys Phe Gly Pro Thr Asn Val Leu Leu Ile Ala His Tyr Ser Phe Leu
465                 470                 475                 480

Ser His Thr Ser Thr Thr Glu Ala Ala Tyr Phe Ala Tyr Leu Leu Cys
                485                 490                 495

Val Cys Val Ser Ser Ile Ser Cys Cys Ile Asp Pro Leu Ile Tyr Tyr
            500                 505                 510

Tyr Ala Ser Ser Glu Cys Gln Arg Tyr Val Tyr Ser Ile Leu Cys Cys
        515                 520                 525

Lys Glu Ser Ser Asp Pro Ser Ser Tyr Asn Ser Ser Gly Gln Leu Met
    530                 535                 540

Ala Ser Lys Met Asp Thr Cys Ser Ser Asn Leu Asn Asn Ser Ile Tyr
545                 550                 555                 560

Lys Lys Leu Leu Thr
                565

<210> SEQ ID NO 39
<211> LENGTH: 224
<212> TYPE: PRT
<213> ORGANISM: Artificial Sequence
<220> FEATURE:
<223> OTHER INFORMATION: Synthetic polypeptide

<400> SEQUENCE: 39

Cys Cys Asp Phe Phe Thr Asn Gln Ala Tyr Ala Ile Ala Ser Ser Ile
  1               5                  10                  15
```

```
Val Ser Phe Val Val Pro Leu Val Ile Met Val Phe Val Tyr Ser Arg
            20                  25              30

Val Phe Gln Glu Ala Lys Arg Gln Leu Gln Lys Ile Asp Lys Ser Glu
        35                  40              45

Gly Arg Phe His Val Gln Asn Leu Ser Gln Val Glu Gln Asp Gly Arg
    50                  55              60

Thr Gly His Gly Leu Arg Arg Ser Ser Lys Phe Cys Leu Lys Glu His
65                      70              75                  80

Lys Ala Leu Lys Thr Leu Gly Ile Ile Met Gly Thr Phe Thr Leu Cys
                85                  90              95

Trp Leu Pro Phe Phe Ile Val Asn Ile Val His Val Ile Gln Asp Asn
                100             105             110

Leu Ile Arg Lys Glu Val Tyr Ile Leu Leu Asn Trp Ile Gly Tyr Val
            115             120             125

Asn Ser Gly Phe Asn Pro Leu Ile Tyr Cys Arg Ser Pro Asp Phe Arg
    130             135             140

Ile Ala Phe Gln Glu Leu Leu Cys Leu Arg Arg Ser Ser Leu Lys Ala
145             150             155             160

Tyr Gly Asn Gly Tyr Ser Ser Asn Gly Asn Thr Gly Glu Gln Ser Gly
                165             170             175

Tyr His Val Glu Gln Glu Lys Glu Asn Lys Leu Leu Cys Glu Asp Leu
            180             185             190

Pro Gly Thr Glu Asp Phe Val Gly His Gln Gly Thr Val Pro Ser Asp
        195             200             205

Asn Ile Asp Ser Gln Gly Arg Asn Cys Ser Thr Asn Asp Ser Leu Leu
    210             215             220

<210> SEQ ID NO 40
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 40

Thr Trp Asp Ala Tyr Lys Asn Leu
1               5
```